United States Patent
Bhuniya et al.

(10) Patent No.: US 8,299,115 B2
(45) Date of Patent: Oct. 30, 2012

(54) PYRROLE-2-CARBOXAMIDE DERIVATIVES AS GLUCOKINASE ACTIVATORS, THEIR PROCESS AND PHARMACEUTICAL APPLICATION

(76) Inventors: Debnath Bhuniya, Maharashtra (IN); S. Gobind Kapkoti, Maharashitra (IN); S. Jayakumar Warrier, Maharashtra (IN); Gagan Kukrejka, Maharashtra (IN); N. Jagadeesh Mavinahalli, Maharashtra (IN); P. Venkata Palle, Maharashtra (IN); A. Kasim Mookhtiar, Bangalore (IN)

( * ) Notice: Subject to any disclaimer, the term of this patent is extended or adjusted under 35 U.S.C. 154(b) by 231 days.

(21) Appl. No.: 12/600,577

(22) PCT Filed: Jun. 5, 2008

(86) PCT No.: PCT/IN2008/000354
§ 371 (c)(1), (2), (4) Date: May 14, 2010

(87) PCT Pub. No.: WO2008/149382
PCT Pub. Date: Dec. 11, 2008

(65) Prior Publication Data
US 2010/0292143 A1    Nov. 18, 2010

(30) Foreign Application Priority Data
Jun. 8, 2007 (IN) .......................... 1195/CHE/2007

(51) Int. Cl.
*A61K 31/4025* (2006.01)
*C07D 207/34* (2006.01)
(52) U.S. Cl. ...................................... 514/422; 548/518
(58) Field of Classification Search ................. 548/518; 514/422
See application file for complete search history.

(56) References Cited

U.S. PATENT DOCUMENTS

| | | | |
|---|---|---|---|
| 2007/0049573 A1 * | 3/2007 | Bauer et al. | 514/211.15 |
| 2008/0090816 A1 * | 4/2008 | Jones et al. | 514/228.2 |
| 2009/0137573 A1 * | 5/2009 | Oberboersch et al. | 514/227.8 |

FOREIGN PATENT DOCUMENTS

| | | | |
|---|---|---|---|
| EP | 1466902 | * | 10/2004 |
| WO | WO 2007/141039 | * | 12/2007 |

OTHER PUBLICATIONS

Bryn et al, Solid State Chemistry of Drugs, 2nd edition, 1999, SSCI, Inc. Chapter 10, Polymorphs, p. 232-247.*
Bundgaard, Design of Prodrugs, 1985, Elsevier, Chapter 1, p. 1-4.*
Souillac et al, Encyclopedia of Controlled Drug Delivery, 1999, John Wiley & Sons, p. 212-227.*
Rodriquez-Spong et al, General principles of pharmaceutical solid polymorphism: a supramolecular perspective, 2004, Advanced Drug Delivery Reviews, vol. 56, p. 241-274.*
Singh, Structural Characterization of Side-by-Side Binding for a Cross-Linked Lexitropsin Dimer Designed to Target G*C Base Pairs in the DNA Minor Groove, Magnetic Resonance in Chemistry, 1996, vol. 34, p. S55-S66.*
Mullican et al., "Novel Thiophene-, Pyrrole-, Furan-, and Benzenecarboxamidotetrazoles as Potential Antiallergy Agents," J. Med. Chem. 34:2186-2194 (1991).

* cited by examiner

*Primary Examiner* — Golam M M Shameem
*Assistant Examiner* — Karen Cheng
(74) *Attorney, Agent, or Firm* — K&L Gates LLP

(57) ABSTRACT

Pyrrole-2-carboxamide derivatives, their polymorphs, stereoisomers, prodrugs, solvates, pharmaceutically acceptable salts and formulations thereof, beneficial for prophylaxis, management, treatment, control of progression, or adjunct treatment of diseases and/or medical conditions where the activation of glucokinase would be beneficial, are disclosed. The disclosure also provides process of preparation of these pyrrole-2-carboxamides.

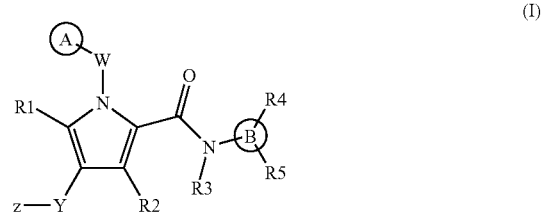

14 Claims, 1 Drawing Sheet

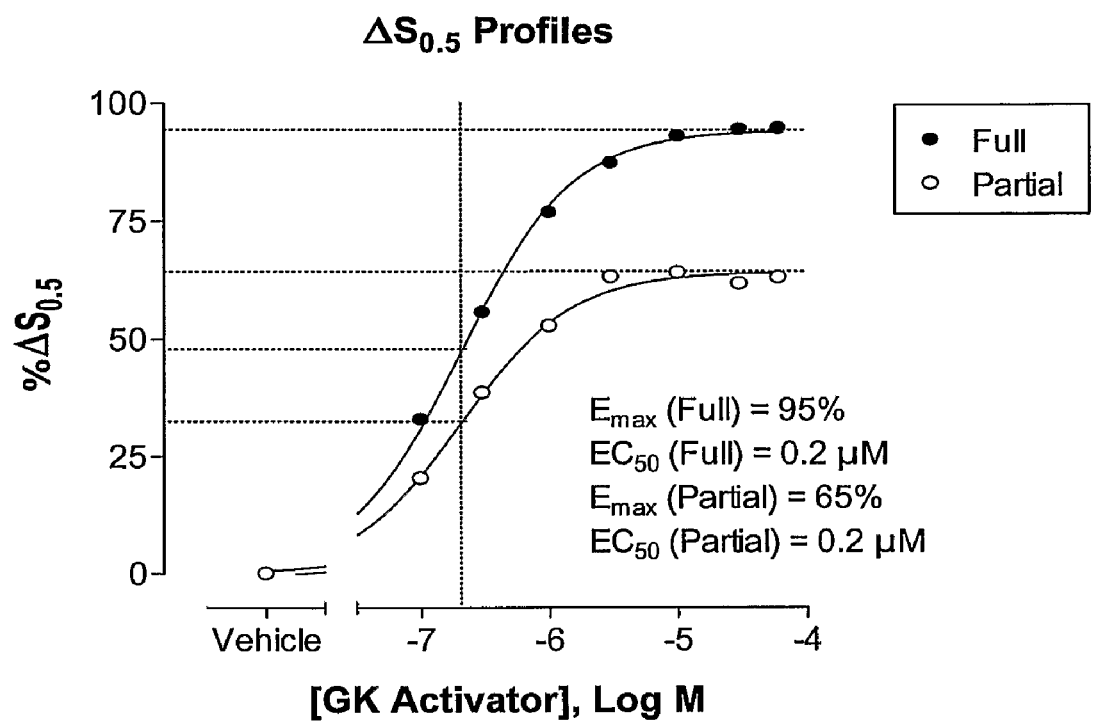

PYRROLE-2-CARBOXAMIDE DERIVATIVES AS GLUCOKINASE ACTIVATORS, THEIR PROCESS AND PHARMACEUTICAL APPLICATION

FIELD OF THE INVENTION

This disclosure relates to a series of novel pyrrole-2-carboxamide derivatives, their polymorphs, stereoisomers, prodrugs, solvates, pharmaceutically acceptable salts and formulations thereof. The disclosure also relates to the process for preparation of substituted pyrrole-2-carboxamide derivatives along with their glucokinase activating effects, which are beneficial for the prophylaxis, management, treatment, control of progression, or adjunct treatment of diseases and/or medical conditions where the activation of glucokinase would be beneficial, such as diabetes, dyslipidemia, metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

It also relates to compounds of formula (I) of the present disclosure with partial Glucokinase activities identified by the method described in our co-pending application 409/CHE/2007 useful for the treatment of hyperglycemia, diabetes, obesity, dyslipidemia, metabolic syndrome and like, in mammals and have minimum hypoglycemic potential.

It also relates to compounds with liver selective Glucokinase activation, useful for the treatment of hyperglycemia, diabetes, obesity, dyslipidemia, metabolic syndrome and like, in mammals and have minimum hypoglycemic potential.

BACKGROUND

Diabetes mellitus is a metabolic disorder characterized by recurrent or persistent hyperglycemia (high blood glucose) and other signs, as distinct from a single disease or condition. Glucose level abnormalities can result in serious long-term complications, which include cardiovascular disease, chronic renal failure, retinal damage, nerve damage (of several kinds), microvascular damage and obesity.

Type 1 diabetes, also known as Insulin Dependent Diabetes Mellitus (IDDM), is characterized by loss of the insulin-producing β-cells of the islets of Langerhans of the pancreas leading to a deficiency of insulin. Type-2 diabetes previously known as adult-onset diabetes, maturity-onset diabetes, or Non-Insulin Dependent Diabetes Mellitus (NIDDM)—is due to a combination of increased hepatic glucose output, defective insulin secretion, and insulin resistance or reduced insulin sensitivity (defective responsiveness of tissues to insulin).

Chronic elevation of blood glucose level leads to damage of blood vessels. In diabetes, the resultant problems are grouped under "microvascular disease" (due to damage of small blood vessels) and "macrovascular disease" (due to damage of the arteries). Examples of microvascular disease include diabetic retinopathy, neuropathy and nephropathy, while examples of macrovascular disease include coronary artery disease, stroke, peripheral vascular disease, and diabetic myonecrosis.

Diabetic retinopathy, characterized by the growth of weakened blood vessels in the retina as well as macular edema (swelling of the macula), can lead to severe vision loss or blindness. Retinal damage (from microangiopathy) makes it the most common cause, of blindness among non-elderly adults in the US. Diabetic neuropathy is characterized by compromised nerve function in the lower extremities. When combined with damaged blood vessels, diabetic neuropathy can lead to diabetic foot. Other forms of diabetic neuropathy may present as mononeuritis or autonomic neuropathy. Diabetic nephropathy is characterized by damage to the kidney, which can lead to chronic renal failure, eventually requiring dialysis. Diabetes mellitus is the most common cause of adult kidney failure worldwide. A high glycemic diet (i.e., a diet that consists of meals that give high postprandial blood sugar) is known to be one of the causative factors contributing to the development of obesity.

Glucokinase (GK), also known as hexokinase IV or D, is one of four glucose-phosphorylating enzymes called hexokinases that catalyze the first step of glycolysis, the conversion of glucose to glucose 6-phosphate (G6P), in vertebrate tissues. GK functions in a dual role, with distinct functions in the pancreas and liver; (a) as a molecular glucose sensor in the insulin-producing pancreatic β-cells, and (b) as the high-capacity enzymatic step initiating the storage of glucose in the form of glycogen in the liver and uptake of glucose during hyperglycemia. Therefore, GK plays a central role in glucose homeostasis, through the phosphorylation of glucose in the liver, and the modulation of insulin secretion in the pancreas (Postic, C. et al (1999) *J. Biol. Chem.* 274: 305-315). GK also functions as a sensor in other neuroendocrine cells of the gastrointestinal tract and in various brain cells including specific cells in the hypothalamus (Jetton, T. A. et al (1994) *J. Biol. Chem.* 269: 3641-3654).

The physiological concentration of glucose in human plasma is approximately 5.5 mM under fasting conditions, and increases to about 12 mM in the fed state. This concentration is dependent on and maintained by the activity of GK, which senses glucose and controls metabolic flux in key cell types. The glucose concentration, at which GK activity is at half of its maximal velocity or $V_{max}$ is defined as its $S_{0.5}$. The $S_{0.5}$ of GK for glucose lies in the middle of the physiological glucose concentration range at approximately 8 mM, allowing this enzyme to act as a molecular glucose sensor crucial for glucose homeostasis. The limited tissue distribution and unique kinetic properties of GK allow it to play a critical role in pancreatic β-cell insulin secretion and hepatic glucose utilization. GK differs from the other members of the mammalian hexokinase family in its unique sigmoidal kinetics with respect to glucose, a high $S_{0.5}$ that lies in the physiological glucose concentration range (the other three mammalian hexokinases have $S_{0.5}$ values less than 0.5 mM), the lack of product inhibition by G6P, and its tissue distribution in cell types that are thought to be responsive to changing plasma glucose levels.

Tissue-specific differences have been observed between the regulation of GK in the liver and the pancreas. In the liver, GK is allosterically inhibited by the glucokinase regulatory protein (GKRP), which results in its sequestration in the nucleus and subsequent protection from proteolytic degradation. This inhibition is reversed by high concentrations of glucose and by fructose 1-phosphate, and is potentiated by fructose 6-phosphate. In the pancreatic β-cells, GK expression is believed to be constitutive. GK is also known to be expressed in the hypothalamus, where it may exert effects on feeding behavior, and in the intestine K and L cells, where it may contribute to the secretion of enteroincretins such as glucagon-like peptide-1 (GLP-1), glucose dependent insulinotropic peptide (GIP) (Matschinsky F. M. et al (2006) *Diabetes* 55: 1-12; Theodorakis M. J. et al (2006) *Am. J. Physiol. Endocrinol. Metab.* 290: E550-E559). Given the role of GK as a molecular glucose sensor, it is not surprising that GK mutations have a profound influence on glucose homeostasis. About 2000 GK mutations that have been identified in humans result in impaired glucose-mediated insulin secretion and maturity-onset diabetes of the young type 2 (MODY-2). Some of these mutations result in decreased accumulation of hepatic glycogen, while others decrease GK activity by reducing the stability of the enzyme or by decreasing its $V_{max}$. Mutations that result in activation of GK are implicated in the onset of persistent hyperinsulinemic hypoglycemia of infancy (PHHI). Single point mutations (e.g. V62M, D158A, Y214A, V455M, and F456V) in regions distinct from the substrate binding site of the enzyme lead to modulation of GK activity (Glaser, B. et al (1998) *N. Engl. J. Med.* 338: 226-230; Gloyn, A. L. (2003) *Hum. Mutat.* 22: 353-362; Gloyn, A. L. et al (2003) *Diabetes* 52: 2433-2440). These observations highlight that GK activity can be regulated through allosteric modulation.

Homozygous knock out of GK in mice results in severe diabetes and death, while heterozygous disruption results in a milder diabetic phenotype, decreased hepatic glucose uptake and impaired insulin secretion in response to glucose. Conversely, over-expression of GK in fat-induced diabetic as well as non-diabetic mice results in improved glucose tolerance. Transgenic mice over-expressing GK in the liver show a modest (20%) increase in fasting GK activity, which correlates with lower fasting plasma glucose and insulin, and improved glucose tolerance (Hariharan, N. et al (1997) *Diabetes* 46: 11-16).

The enzymatic properties of GK can be described in terms of its velocity (i.e. its rate of converting glucose to G6P) and its $S_{0.5}$ for glucose (i.e. the apparent glucose concentration at which GK converts glucose to G6P at half of its maximal velocity). The $S_{0.5}$ of human GK for glucose is approximately 8 mM in enzyme based assay. GKAs induce increased conversion by GK of glucose to G6P by either decreasing the $S_{0.5}$ of GK for glucose, increasing its $V_{max}$, or by a combination of both, and can potentially lower blood glucose concentrations to hypoglycemic levels.

Several patent applications and publications describe the discovery of small-molecule glucokinase activators (GKAs) that allosterically modulate or activate the activity of GK (Kamata, K. et al (2004) *Structure* 12: 429-438; WO 2003/055482 A1; WO 2005/123132 A2; WO 2004/002481 A2; U.S. Pat. No. 6,486,184 B2; WO 2006/040528 A1; Fyfe, M. C. T. (2007) *Diabetologia*, 50: 1277-1287; McKerrecher, D. et al *Bioorg. Med. Chem. Lett.* 15 (2005) 2103-2106; Efanov, A. M. et al (2005) *Endocrinology* 146: 3696-3701; Printz, R. L. and Granner, D. K. (2005) *Endocrinology* 146: 3693-3695; Brocklehurst, K. J. et al (2004) *Diabetes*, 53: 535-541; Grimsby, J. et al (2003) *Science* 301: 370-373). These GKAs increase GK activity by decreasing its $S_{0.5}$ for glucose, and, in some cases, also increasing its $V_{max}$. However, for many of these compounds, hypoglycemia has been reported in animal studies which may be a consequence of excessive GK activation. For example, GK activators like Ro-28-1675 cause hypoglycemia in animal efficacy models (Kamata, K. et al (2004) *Structure* 12: 429-438). Similar hypoglycemic potential is seen in another GK activator, PSN-GK1, at higher dose (Fyfe, M. C. T. (2007) *Diabetologia*, 50: 1277-1287).

Rat liver glucokinase is inhibited by long chain acyl-CoA. Deinhibition of such inhibition may also result into glucokinase activation (Tippett P. S. et. al (1982) *J. Biol. Chem.* 25712839-12845, Tippett P. S. et. al (1982) *J. Biol. Chem.* 257, 12846-12852.

A concept of minimizing hypoglycemic potential by liver selective glucokinase activation has been mentioned in patent application no. WO 2005/123123 wherein, compounds described in WO 2004/002481 are identified as liver selective glucokinase activators which increase glucose utilization in the liver without inducing an increase in insulin secretion in response to glucose.

The present disclosure provides a novel class of compounds characterized as glucokinase activators or modulators, and their potential use as medicament for the prophylactic or therapeutic treatment of hyperglycemia, diabetes, obesity, dyslipidemia, metabolic syndrome and like.

SUMMARY

The present disclosure relates to a series of pyrrole-2-carboxamide derivatives of Formula (I), their polymorphs, stereoisomers, prodrugs, solvates or pharmaceutically acceptable salts and formulations thereof as Glucokinase Activators (GKA);

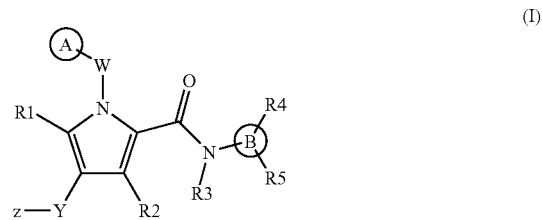

wherein
Ring A is a mono or a bicyclic ring independently selected from cycloalkyl, aryl, heteroaryl and partially/fully saturated rings thereof;
Ring A is optionally substituted with up to 4 substituents independently selected from alkyl, alkenyl, alkynyl, halogen, mono, di or perhaloalkyl, nitrile, nitro, oxo, —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_nC(O)NR^6R^7$—$(CR^8R^9)_nC(O)R^6$, cycloalkyl, cycloalkylalkyl, heterocyclyl, heterocycloalkyl, aryl, arylalkyl, heteroaryl, heteroarylalkyl, tetrazole, tetrazolylalkyl groups; further, the cycloalkyl, heterocycloalkyl, aryl, heteroaryl groups are optionally substituted with common substituents;
p=0-2; n=0-4;
$R^6$ and $R^7$ are independently selected from a group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, wherein each of alkyl, alkenyl, alkynyl, aryl, arylalkyl, heteroaryl, heteroarylalkyl, cycloalkyl, cycloalkylalkyl, heterocyclyl and heterocyclylalkyl is optionally substituted with common substituents;
$R^8$ and $R^9$ are independently selected from a group consisting of hydrogen, fluorine, chlorine, $OR^6$, straight and branched chain alkyl groups, aryl, arylalkyl, perfluoroalkyl and other common substituents; wherein the aryl group is optionally substituted with common substituents;
W and Y independently represent:
—$(X)_m(CR^8R^9)_n(X)_o$—,
wherein X is selected from C(O), O, $S(O)_p$ and $NR^6$,
$R^6$, $R^8$, $R^9$ are as described herein above,
m and o are independently either 0 or 1,
n is selected from numbers 0-4,
p is selected from numbers 0-2;

Z is other than hydrogen, and is selected from a group consisting of halogen, straight or branched chain alkyl, alkenyl, alkynyl, aryl, aralkyl, heteroaryl, heteroarylalkyl, heterocyclyl, heterocyclylalkyl, cycloalkyl, and cycloalkylalkyl, wherein each of alkyl, alkenyl, alkynyl, aryl, aralkyl, heteroaryl, heteroarylalkyl, heterocyclyl, heterocyclylalkyl, cycloalkyl, cycloalkylalkyl is optionally substituted with up to 4 substituents independently selected from halogen, nitrile, nitro, oxo, —$NR^6R^7$, —$OR^6$, —$S(O)_p$ $R^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_nC(O)NR^6R^7$, —$(CR^8R^9)_nS(O)_p$ $NR^6R^7$, —$(CR^8R^9)_nNC(O)R^6$, —$(CR^8R^9)_nR^6$, —$(CR^8R^9)_nNR^6R^7$, —$(CR^8R^9)_nC(O)R^6$, tetrazole, and tetrazolylalkyl;

wherein, p=0-2; n=0-4;

$R^6$, $R^7$, $R^8$ and $R^9$ are as described herein above;

$R^1$, $R^2$ are independently selected from hydrogen, alkyl, perfluoroalkyl, cycloalkyl, aryl, heterocyclyl, heteroaryl, cycloalkylalkyl, arylalkyl, heterocyclylalkyl, heteroarylalkyl, —OH, —$OR^6$, —$(CH_2)nOR^6$, tetrazole and tetrazolylalkyl, wherein each of alkyl, cycloalkyl, aryl, heterocyclyl, heteroaryl, cycloalkylalkyl, arylalkyl, heterocyclylalkyl, heteroarylalkyl, —OH, —$OR^6$, —$(CH_2)_nOH$, —$(CH_2)_nOR^6$, tetrazole and tetrazolylalkyl is further substituted with common substituents;

wherein, n=0-4;

$R^6$ is as described herein above;

$R^3$ is selected from a group consisting of hydrogen, alkyl and perfluoroalkyl;

Ring-B is optionally substituted 4-10 membered mono or bicyclic moieties containing at least one nitrogen in the ring, with the proviso that the amide nitrogen of formula (I) is not connected through any heteroatom of ring-B;

$R^4$ and $R^5$ are independently selected from a group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, tetrazole, tetrazolylalkyl, mono, di or tri substituted haloalkyl, nitrile, nitro, oxo, —$NR^6$, —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_n(CO)NR^6R^7$, —$(CR^8R^9)_nS(O)_pNR^6R^7$, —$(CR^8R^9)_nN(R^6)C(O)R^6$, —$(CR^8R^9)_nOR^6$, $C(R^8R^9)_nNR^6R^7$ and $C(R^8R^9)_nCO(R^6)$; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$;

wherein n=0-4;

$R^6$, $R^7$, $R^8$ and $R^9$ are as described herein above;

in addition to $R^4$ and $R^5$, ring-B can be further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$.

The disclosure also relates to the process of preparation of substituted pyrrole-2-carboxamide derivatives of formula (I).

These GKAs are beneficial for the prophylaxis, management, treatment, control of progression, or adjunct treatment of diseases and/or medical conditions such as diabetes, obesity, dyslipidemia, metabolic syndrome and/or diabetes-related complications including retinopathy, nephropathy, neuropathy, ischemic heart disease, arteriosclerosis, β-cell dysfunction, and as therapeutic and/or prophylactic agents for obesity where the activation of glucokinase would be beneficial.

The present disclosure also relates to the compounds of formula (I) that are partial GK activators. Such partial GK activators identified may be useful for the treatment of hyperglycemia, diabetes, obesity, dyslipidemia, metabolic syndrome and the like, in mammals and have minimum hypoglycemic potential.

The present disclosure also relates to the compounds of formula (I) that are liver selective GK activators. Such liver selective GK activators may be useful for the treatment of hyperglycemia, diabetes, obesity, dyslipidemia, metabolic syndrome and the like, in mammals and have minimum hypoglycemic potential.

These and other features, aspects, and advantages of the present subject matter will become better understood with reference to the following description and appended claims. This Summary is provided to introduce a selection of concepts in a simplified form. This Summary is not intended to identify key features or essential features of the claimed subject matter, nor is it intended to be used to limit the scope of the claimed subject matter.

DESCRIPTION OF DRAWINGS

The above and other features, aspects, and advantages of the subject matter will become better understood with regard to the following description, appended claims, and accompanying drawings where:

FIG. 1 describes the dose dependent effect of two typical examples from general formula-I on the % $\Delta S_{0.5}$ of glucokinase for glucose. Graph with filled circle (●) is for a representative full glucokinase activator having $EC_{50}$: 0.2 µM and $E_{max}$: 95%; whereas, the graph with open circle (○) is for a partial glucokinase activator having $EC_{50}$: 0.2 µM and $E_{max}$: 65%.

DETAILED DESCRIPTION OF THE DISCLOSURE

Definitions

In the structural formulae given herein and throughout the present disclosure, the following terms have the indicated meaning:

The term "optionally substituted" as used herein means that the group in question is either unsubstituted or substituted with one or more of the substituents specified. When the group in question is substituted with more than one substituent, the substituent may be same or different.

The term "mono or bicyclic moieties" refers to a carbocycle, an aryl, a heterocycle or a heteroaryl which can be aromatic or non-aromatic, saturated or unsaturated, 3 to 18 ring atoms system including 0 to 5 heteroatoms independently selected from S, N, O; the said rings can be optionally substituted with common substituents.

The term "aryl", alone or in combination with any other term, refers to a monocyclic or a polycyclic aromatic ring system containing carbon-ring atoms, such as phenyl, biphenyl, naphthyl or anthryl which optionally carries one or more substituents, preferably one to three, each independently selected from halogen, trifluoromethyl, trifluoromethoxy, amino, alkyl, alkenyl, alkynyl, alkoxy, alkylcarbonyl, alkoxycarbamoyl, aminocarbonyl, cycloalkyl, cycloalkenyl, acyl, cyano, carbamoyl, methylendioxy, carboxy, alkoxycarbonyl, aryloxy, alkylaminocarbonyl, dialkylaminocarbonyl, hydroxy, heteroaryl, heterocyclyl, nitro, SO$_2$alkyl, SO$_2$cycloalkyl and the like.

"Heteroaryl", alone or in combination with any other term, refers to a monocyclic aromatic ring structure containing 5 or 6 ring atoms, or a bicyclic aromatic group having 8 to 12 atoms, containing one or more heteroatoms independently selected from O, S, and N, and optionally substituted with 1 to 3 groups or substituents such as halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. "Heteroaryl" is also intended to include oxidized S or N, such as sulfinyl, sulfonyl and N-oxide of tertiary ring nitrogen. A carbon or hetero-atom is the point of attachment of the heteroaryl ring structure such that a stable aromatic ring is retained. Examples of heteroaryl groups are azepinyl, benzimidazolyl, benisoxazolyl, benzofurazanyl, benzopyranyl, benzothiazolyl, benzothienyl, benzoxazolyl, cinnolinyl, pyridinyl, pyridazinyl, pyrazinyl, quinazolinyl, purinyl, indolyl, quinolinyl, pyrimidinyl, pyrrolyl, oxazolyl, oxadiazolyl, thiazolyl, thienyl, isooxazolyl, oxathiadiazolyl, isothiazolyl, tetrazolyl, imidazolyl, triazinyl, furanyl, benzofuryl, naphthyridinyl, thiadiazolyl, triazolyl, oxazolopyridinyl, imidazopyridinyl, thiazolopyridinyl, thiazolotraizinyl, thiazolopyrazinyl, quinoxalinyl and the like. A substituted heteroaryl contains a substituent attached at an available carbon or heteroatom to produce a stable compound. "Heteroaryl" is also intended to encompass compounds where a heteroaryl is attached to another non-aromatic cyclyl or heterocyclyl rings. Non-limiting examples include chromanyl, dihydrobenzofuranyl, indalinyl, dihydrobenzothienyl, benzodioxolyl dihydrobenzothienyl, dihydrobenzothiopyranyl, isochromanyl, dihydrobenzothiopyranyl sulfone, 1,3-dioxolanyl, benzofuryl, and the like.

As used herein, "heterocycle" or "heterocyclyl" refers to a stable 4 to 7-membered monocyclic or stable 8 to 12 membered bicyclic heterocyclic non-aromatic ring which is either saturated or unsaturated, and which consists of carbon atoms and from one to five heteroatoms selected from the group consisting of N, O, and S. "Heterocyclyl" is also intended to include oxidized S or N, such as sulfinyl, sulfonyl and N-oxide of tertiary ring nitrogen. The heterocyclic ring may be attached at any heteroatom or carbon atom which results in the creation of a stable structure. Non-limiting examples include imidazolidinyl, imidazolinyl, indolinyl, isoindolinyl, isoquinolinyl, isothiazolidinyl, isothiazolidinyl, morpholinyl, 2-oxopiperazinyl, 2-oxopiperdinyl, 2-oxopyrrolidinyl, piperidyl, piperazinyl, pyrazolidinyl, pyrrolidinyl, quinoxalinyl, dihydroimidazole-one, tetrahydrofuryl, tetrahydroisoquinolinyl, tetrahydroquinolinyl, tetrahydroquinoxalinyl, thiamorpholinyl sulfoxide, thiazolinyl, thiazolidine, benzooxazinone, benzothiazinone, isoxazoline, oxazolidin, dihydropyrazinyl, dihydrobezoxazinyl, dihydrobenzothiazinyl, benzodioxolyl, dihydrobenzodioxolyl, dihydropyridyl and dihydrobenzodiazepinone.

"Alkyl" refers to straight or branched chain having 1 to 10 carbon atoms which is/are further substituted with one or more common substituents. Examples of alkyl groups include, but are not limited to methyl, ethyl, propyl, isopropyl, butyl, t-butyl and the like.

"Cycloalkyl" refers to a cyclic or polycyclic alkyl group containing 3 to 15 carbon atoms which are further substituted with one or more common substituents. Examples of cycloalkyl groups include, but are not limited to cyclopropyl, cyclobutyl, cyclopentyl, bicyclo[4.4.0]decane, adamantanyl, and the like. "Cycloalkyl" is also intended to encompass cyclic alkyl group attached to an aryl group such as 1,2,3,4-tetrahydronaphthalenyl, indanyl and the like.

"Alkenyl", alone or in combination refers to a straight, branched, mono cyclic or polycyclic unsaturated hydrocarbon preferably containing 2 to 10 carbon atoms, and having 1 to 5 double bonds and preferably 1 double bond. Examples of alkenyl groups include, but are not limited to are ethenyl, propenyl, isopropenyl, butenyl, bicycle[2.2.1]heptene and the like.

"Alkynyl", alone or in combination with any other term means a straight or branched hydrocarbon containing 2 to 10 carbon atoms containing 1 to 3 carbon to carbon triple bonds and at least one carbon to carbon triple bond. Examples of alkynyl groups include but are not limited to ethynyl, propynyl, butynyl and the like.

"Halo" or "Halogen", alone or in combination with any other term means halogens such as chloro (Cl), fluoro (F), bromo (Br) and iodo (I).

Common substitution or common substituents are defined as halo, straight chain or branched chain alkyl, alkenyl, alkynyl, cycloalkyl, aryl, heteroaryl, heterocycle, alkylsulphonyl, nitro, cyano, —COOR$^6$, —C(O)NR$^6$R$^7$, —OR$^6$, —SR$^6$, —NR$^6$R$^7$.

The compounds of the present disclosure may have the ability to crystallize in more than one form, a characteristic known as polymorphism, and all such polymorphic forms ("polymorphs") are encompassed within the scope of the disclosure. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as geometric isomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms. In general, compounds may be hydrated, solvated or N-oxides. Certain compounds may exist in multiple crystalline or amorphous forms. Also contemplated within the scope of the disclosure are congeners, analogs, hydrolysis products, metabolites and precursor or prodrugs of the compound. In general, unless otherwise indicated, all physical forms are equivalent for the uses contemplated herein and are intended to be within the scope of the present disclosure.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

The present disclosure relates to novel pyrrole-2-carboxamide derivatives useful as glucokinase activators. Compounds of the present disclosure are described by formula (I)

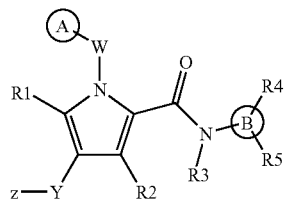

(I)

wherein, Ring A is a mono or a bicyclic ring independently selected from cycloalkyl, aryl, heteroaryl and partially/fully saturated rings thereof;
Ring A is optionally substituted with up to 4 substituents independently selected from alkyl, alkenyl, alkynyl, halogen, mono, di or perhaloalkyl, nitrile, nitro, oxo, —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_nC(O)NR^6R^7$—$(CR^8R^9)_nC(O)R^6$, cycloalkyl, cycloalkylalkyl, heterocyclyl, heterocycloalkyl, aryl, arylalkyl, heteroaryl, heteroarylalkyl, tetrazole, tetrazolylalkyl groups; further, the cycloalkyl, heterocycloalkyl, aryl, heteroaryl groups are optionally substituted with common substituents;
p=0-2; n=0-4;
$R^6$ and $R^7$ are independently selected from a group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, wherein each of alkyl, alkenyl, alkynyl, aryl, arylalkyl, heteroaryl, heteroarylalkyl, cycloalkyl, cycloalkylalkyl, heterocyclyl and heterocyclylalkyl is optionally substituted with common substituents;
$R^8$ and $R^9$ are independently selected from a group consisting of hydrogen, fluorine, chlorine, $OR^6$, straight and branched chain alkyl groups, aryl, arylalkyl, perfluoroalkyl and other common substituents; wherein the aryl group is optionally substituted with common substituents;
W and Y independently represent:
—$(X)_m(CR^8R^9)_n(X)_o$—,
wherein X is selected from C(O), O, S(O)$_p$ and $NR^6$,
$R^6$, $R^8$, $R^9$ are as described herein above,
m and o are independently either 0 or 1,
n is selected from numbers 0-4,
p is selected from numbers 0-2;
Z is other than hydrogen, and is selected from a group consisting of halogen, straight or branched chain alkyl, alkenyl, alkynyl, aryl, aralkyl, heteroaryl, heteroarylalkyl, heterocyclyl, heterocyclylalkyl, cycloalkyl, and cycloalkylalkyl, wherein each of alkyl, alkenyl, alkynyl, aryl, aralkyl, heteroaryl, heteroarylalkyl, heterocyclyl, heterocyclylalkyl, cycloalkyl, cycloalkylalkyl is optionally substituted with up to 4 substituents independently selected from halogen, nitrile, nitro, oxo, —$NR^6R^7$, —$OR^6$, —$S(O)_p$ $R^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_nC(O)NR^6R^7$, —$(CR^8R^9)_nS(O)_p$ $NR^6R^7$, —$(CR^8R^9)_nNC(O)R^6$, —$(CR^8R^9)_nOR^6$, —$(CR^8R^9)_nNR^6R^7$, —$(CR^8R^9)_nC(O)R^6$, tetrazole, and tetrazolylalkyl;
wherein, p=0-2; n=0-4;
$R^6$, $R^7$, $R^8$ and $R^9$ are as described herein above;
$R^1$, $R^2$ are independently selected from hydrogen, alkyl, perfluoroalkyl, cycloalkyl, aryl, heterocyclyl, heteroaryl, cycloalkylalkyl, arylalkyl, heterocyclylalkyl, heteroarylalkyl, —OH, —$OR^6$, —$(CH_2)_nOR^6$, tetrazole and tetrazolylalkyl, wherein each of alkyl, cycloalkyl, aryl, heterocyclyl, heteroaryl, cycloalkylalkyl, arylalkyl, heterocyclylalkyl, heteroarylalkyl, —OH, —$OR^6$, —$(CH_2)_nOH$, —$(CH_2)_nOR^6$, tetrazole and tetrazolylalkyl is further substituted with common substituents;
wherein, n=0-4;
$R^6$ is as described herein above;
$R^3$ is selected from a group consisting of hydrogen, alkyl and perfluoroalkyl;
Ring-B is optionally substituted 4-10 membered mono or bicyclic moieties containing at least one nitrogen in the ring, with the proviso that the amide nitrogen of formula (I) is not connected through any heteroatom of ring-B;
$R^4$ and $R^5$ are independently selected from a group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, tetrazole, tetrazolylalkyl, mono, di or tri substituted haloalkyl, nitrile, nitro, oxo, —$NR^6$, —$NR^6R^7$, —$OR^6$, —$S(O)_pR^6$, —$S(O)_pNR^6R^7$, —$NR^6S(O)_pR^7$, —$NR^6C(O)R^7$, —$OS(O)_pR^7$, —$NR^6C(O)OR^7$, —$(CR^8R^9)_nC(O)OR^6$, —$(CR^8R^9)_n(CO)NR^6R^7$, —$(CR^8R^9)_nS(O)_p$ $NR^6R^7$, —$(CR^8R^9)_nN(R^6)C(O)R^6$, —$(CR^8R^9)_nOR^6$, $C(R^8R^9)_nNR^6R^7$ and $C(R^8R^9)_nCO(R^6)$; wherein each of $R^4$ and $R^5$ is optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —$COOR^6$, —$C(O)NR^6R^7$, —$OR^6$, —$SR^6$ or —$NR^6R^7$;
wherein n=0-4;
$R^6$, $R^7$, $R^8$ and $R^9$ are as described herein above; in addition to R4 and R5, ring-B can be further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR6, —C(O)NR6R7, —OR6, —SR6 or —NR6R7.

According to an embodiment, the present disclosure relates to compounds of formula (I) wherein ring A is selected from

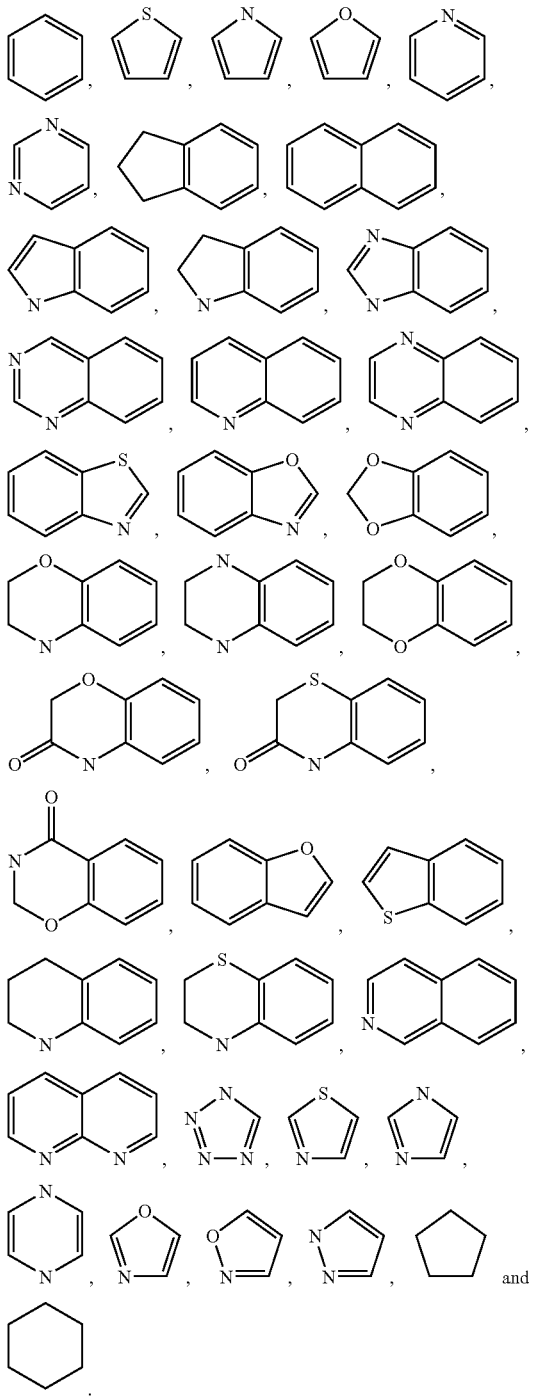

According to another embodiment, the present disclosure relates to compounds of formula (I) wherein ring B is selected from

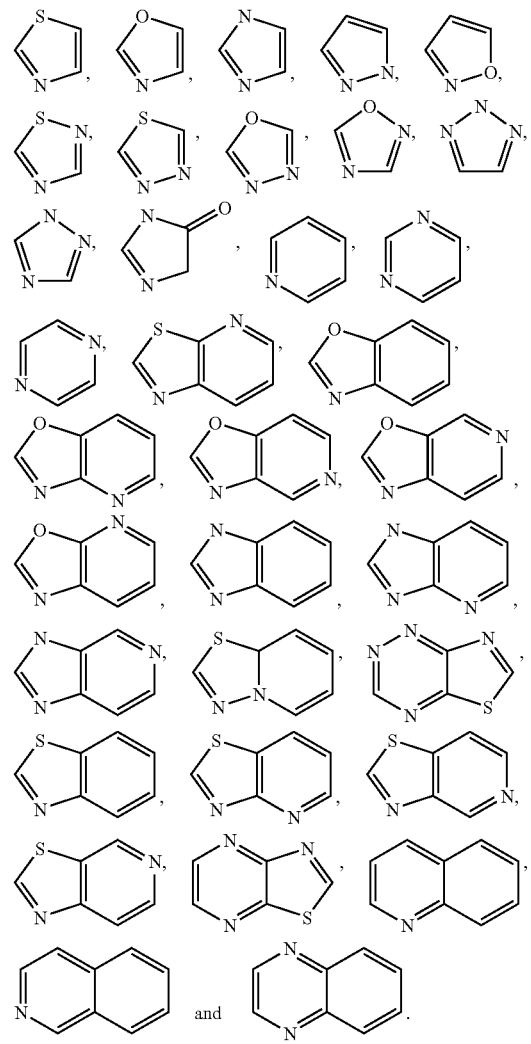

According to a preferred embodiment, the present disclosure relates to compounds of formula (I) wherein
ring A is

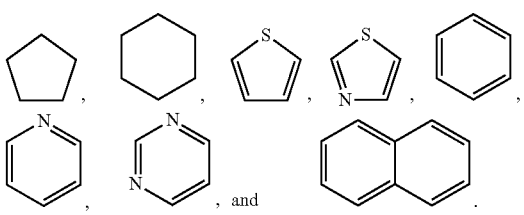

Z is selected from halogen, alkyl, cycloalkyl, heterocyclyl, aryl or heteroaryl.

The present disclosure also relates to the process of preparation of compounds of formula (I).

According to an embodiment, the present disclosure relates to a process for the preparation of a compound of formula (I), or its polymorph, stereoisomer, prodrug, or a solvate thereof, said process comprising:
reacting an acid of formula (II)

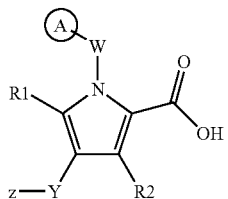

with a compound of formula (III)

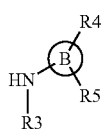

in presence of a suitable amide coupling reagent, optionally hydrolysing and optionally further coupling with an amine of formula NHR6R7 to obtain the compound of formula (I).

According to another embodiment, the present disclosure relates to a process for the preparation of a compound of formula (I), or its polymorph, stereoisomer, prodrug, or a solvate thereof, said process comprising:
converting a compound of formula (Ib)

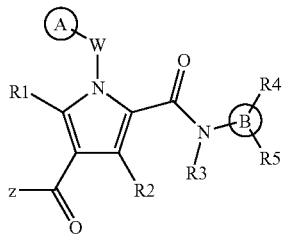

to a compound, of formula (I)

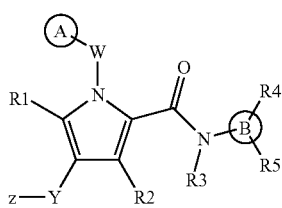

wherein Y is —CH(OH),
by hydrogenating a compound of formula (Ib) using catalyst FeCl2, Pd—C or Raney nickel, or reducing a compound of formula (Ib) using Li, Na, K, NH3, LiH, BH3, LiBH4, SnCl4, NaBH4, NaBH3CN or LiHBEt3 in lower alcohols, THF, acetic acid or water at a temperature in the range of 0-150° C.

Compounds of formula I may be prepared as shown in the following reaction schemes and the description thereof, as well as relevant literature procedures that may be used by one skilled in the art. Exemplary reagents and procedures for these reactions appear hereinafter and in the working examples. Protection and deprotection in the schemes below may be carried out by procedures generally known in the art (see, for example, Greene, T. W. and Wuts, P. G. M., Protecting Groups in Organic Synthesis, 3$^{rd}$ Edition, 1999 [Wiley]). The compounds of formula (I) may be prepared as outlined in the Schemes 1-4:

Scheme 1: General route for the synthesis of compounds formula (I) from compounds of formula (II) and (III) following amide coupling reaction conditions:

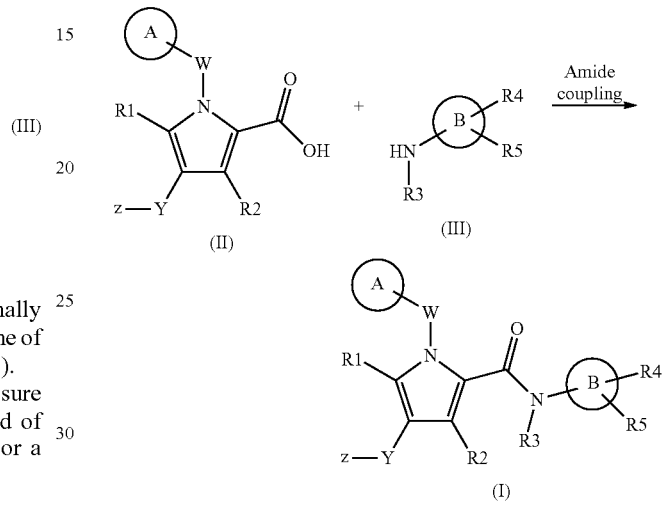

Scheme 2: General route for the synthesis of compounds of formula (Ia) (wherein Y is —CH(OH)— in formula I), from compounds of formula (Ib) following conditions for reduction of carbonyl functional group to alcohol.

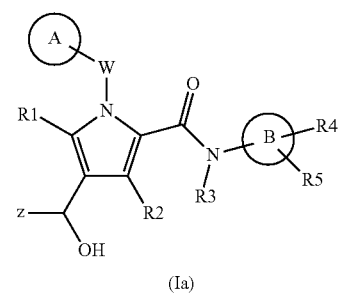

Scheme 3: General route for the synthesis of compounds of formula (Ic) (wherein either of $R^4$ or $R^5$ is $-(CR^8R^9)n(COOH)$ in formula I), from compounds of formula (Id) wherein either of $R^4$ or $R^5$ is $-(CR^8R^9)n(COOR)$ following conditions for ester hydrolysis. R is a suitable alkyl group.

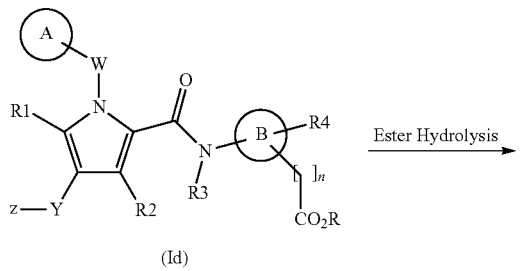

Scheme 4: General route for the synthesis of compounds of formula (Ie) (wherein either of $R^4$ or $R^5$ is $-(CR^8R^9)n(CONR^6R^7)$ in formula I), from compounds of formula (Ic) wherein either of $R^4$ or $R^5$ is $-(CR^8R^9)n(COOH)$ following conditions for amide coupling.

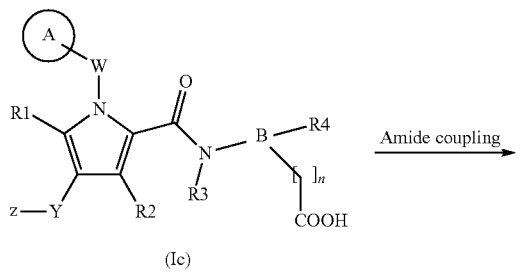

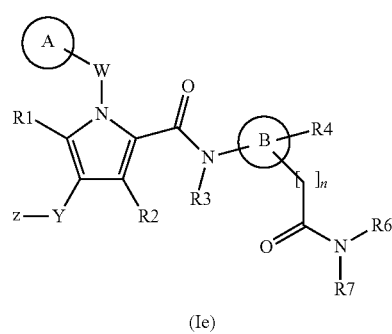

The intermediate compounds of general structure II may be prepared as outlined in scheme 5.

Scheme 5: General route for the synthesis of compounds of formula II, wherein W is $-(X)_m(CR^8R^9)_n(X)_o-$, from compounds of formula (IV) following conditions for ester hydrolysis. Compounds of formula (IV) may be obtained from the compounds of formula (V) and (VI) following conditions for nucleophilic substitution on pyrrole nitrogen. LG is a suitable leaving group like chloro, bromo, iodo, methanesulfonyloxy and trifluoromethanesulfonyloxy groups:

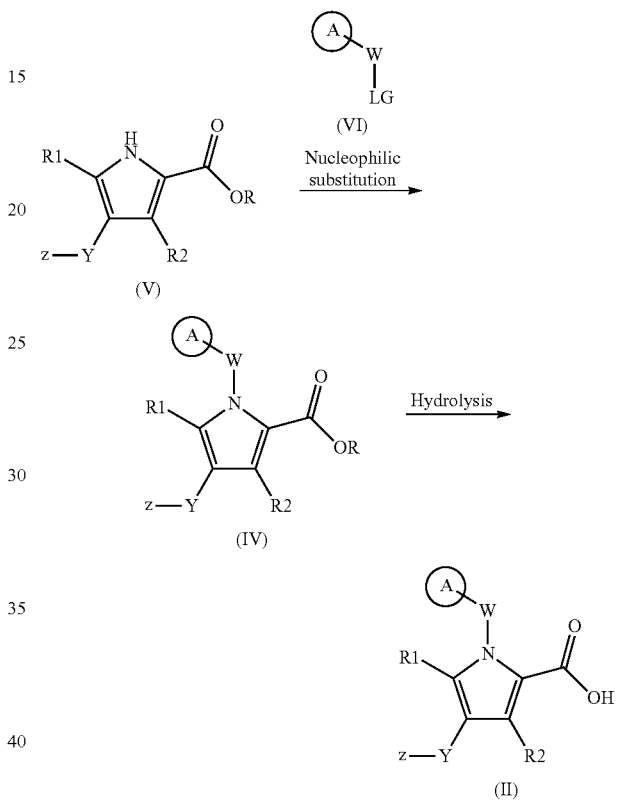

Scheme-6: General route for the synthesis of compounds of formula (V), wherein Y is $-C(O)-$ or $-S(O)_2-$, from ester of substituted pyrrole-2-carboxylic acids (VII) following conditions of Friedel Craft reaction (*Eur. J. Med. Chem* 1993, 28, 481-498).

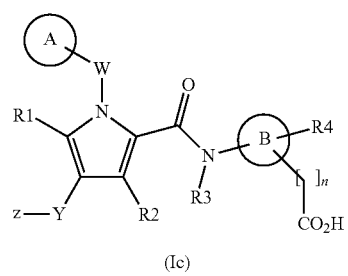

Scheme-7: General route for the synthesis of compounds of formula (Va), from compounds of formula (Vb), following conditions for reduction of arylic carbonyl functional group to arylic methylenes.

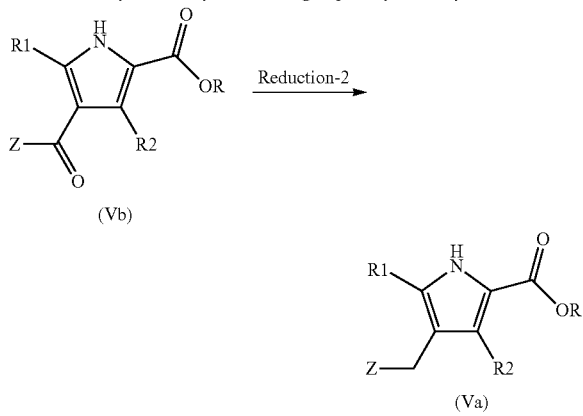

Amide Coupling Conditions: Amide coupling reactions mentioned above may be carried out using any suitable activating reagents like, oxallyl chloride, thionyl chloride, BOP-Cl, DCC, HOBt, EDCI, alkylchloroformate etc. Solvents like dichloromethane, dichloroethane, DMF, dimethylacetamide, THF, acetonitrile or mixture of them may be used. Organic non-nucleophillic bases such as triethyl amine, ethyldiisopropyl amine, pyridine, N-methyl pyrrolidine, N,N-dimethylaminopyridine, DBU, DABCO, other hindered amines and pyridines may be used. The reaction may be carried out at a temperature ranging from −5 to 150° C.

Alternatively, the amide bond may also be formed by reacting carboxylic acid esters (IV) wherein R is alkyl such as methyl or ethyl, with amine of formula (III) in presence of reagents like trialkylaluminium and solvent such as toluene, THF and the like at a temperature in the range of 60-150° C. Such reactions may also be carried out under microwave conditions (Chem. Comm. 2008, 1100-1102).

Conditions for Nucleophilic Substitution: Nucleophilic substitution reactions mentioned above may be carried out using any suitable organic or inorganic bases. Organic bases may be selected from a group consisting of mono, di or trialkyl amines particularly methylamine, ethylamine, dimethylamine, diethylamine or triethylamine. Inorganic bases may be selected from a group consisting of alkali and alkaline earth metal hydrides, hyroxides, carbonates and bicarbonates or mixtures thereof. Solvents used for this reaction may be selected from a group consisting of lower alcohols, acetone, acetonitrile, DMSO, DMF, dimethylacetamide, THF, toluene, or mixtures thereof. The reaction may be carried out at a temperature in the range of 0 to 150° C.

Ester hydrolysis: The hydrolysis reactions mentioned above may be carried out using general saponification conditions employing inorganic bases selected from a group consisting of alkali and alkaline earth metal hyroxides, carbonates and bicarbonates, as for example lithium hydroxide, sodium hydride, sodium carbonate, potassium carbonate and cesium carbonate; in the presence of a solvent selected from a group consisting of water, methanol, ethanol, THF and diethyl ether or a mixture thereof.

Fridel Craft Reaction: The Fridel Craft reaction mentioned above may be carried out using suitable organic acid chloride or alkyl halide in presence of Lewis acid like aluminium chloride, iron (III) chloride, boron trifluoride, niobium pentachloride or lanthanide triflates such as ytterbium (III) triflate.

Reduction-1: Reduction-1 mentioned above may be carried out using hydrogenation in presence of suitable catalyst like $FeCl_2$, Pd—C, Raney nickel or reduction by metal like Li, Na, K and $NH_3$, or by metal hydride like LiH, $BH_3$, $LiBH_4$, $SnCl_4$, $NaBH_4$, $NaBH_3CN$, $LiHBEt_3$ etc. in solvents like lower alcohols, THF, acetic acid or water at temperature in the range of 0-150° C. Such reactions may also be carried out in enantioselective fashion by using appropriate chiral reagents.

Reduction-2: Reduction-2, mentioned above, may be carried out using zinc in presence of HCl or triethylsilyl hydride in presence of TFA, $BF_3$, $AlCl_3$, $BF_3.OEt_2$ etc. Such reactions may also be carried out using molecular Hydrogen or cyclohexene in presence of catalyst like Pd—C, Pt—C, $FeCl_3$ or raney nickel in aqueous alcohol.

Wherever desired or necessary, in any of the above mentioned processes, any of the compounds of formula (I) may be converted into a pharmaceutically acceptable salt or vice versa or converting one salt form into another pharmaceutically acceptable salt form.

According to an embodiment, the present disclosure relates to compounds of formula (I) their polymorphs, stereoisomers, prodrugs, solvates or pharmaceutically acceptable salts and formulations thereof as, which are glucokinase activators, and are beneficial for the prophylaxis, management, treatment, control of progression, or adjunct treatment of diseases and/or medical conditions where the activation of glucokinase would be beneficial, such as diabetes, dyslipidemia, metabolic syndrome, and/or diabetes-related complications including retinopathy, nephropathy, neuropathy, ischemic heart disease, arteriosclerosis, β-cell dysfunction, and as therapeutic and/or prophylactic agents for obesity.

According to another embodiment, the present disclosure relates to compounds of formula (I) their polymorphs, stereoisomers, prodrugs, solvates or pharmaceutically acceptable salts and formulations thereof as, which have partial glucokinase activating effects useful for the treatment of hyperglycemia, diabetes, obesity, dyslipidemia, metabolic syndrome and like, in mammals and have minimum hypoglycemic potential.

The concept of partial glucokinase activation as well as the method for identification of compounds that are partial glucokinase activators has been described in our co-pending application 409/CHE/2007 which is incorporated herein by reference.

The molecular mechanism behind GK activation and blood glucose lowering effect is two fold: (i) more insulin secretion from pancreas, and (ii) effective glycogen deposition in liver. However, excessive glucokinase activation is associated with hypoglycemic potential. Hence, partial GK activators, identified using the present method of the disclosure, will be useful for the treatment of hyperglycemia, diabetes, obesity, dyslipidemia, metabolic syndrome and like, and at the same time will have minimum risk of hypoglycemic potential.

The enzymatic properties of glucokinase can be described in terms of its velocity (i.e. its rate of converting glucose to G6P) and it's $S_{0.5}$ for glucose (i.e. the apparent glucose concentration at which GK converts glucose to G6P at half of its maximal velocity). The $S_{0.5}$ of glucose, in an in vitro assay using recombinant human GK, is approximately 8 mM. GK activators induce increased conversion of glucose to G6P by GK by decreasing the $S_{0.5}$ of GK for glucose.

An important concept for understanding the disclosure is that full and partial activators of glucokinase behave differently in enzyme based glucokinase activation assay, as given under:

Glucokinase activators such as Ro-28-1675, when analyzed for their dose dependent effect on reduction of $S_{0.5}$ of glucokinase for glucose in an enzyme-based in vitro assay, showed a drop in $S_{0.5}$ from approximate 8 mM glucose all the way down to approximately 1.0 mM or less.

Applicants conceptualized that the hypoglycemic potential of a GK activator can be predicted by monitoring the effect of a GK activator on the reduction of $S_{0.5}$ of Glucokinase for glucose ($\Delta S_{0.5}$) in an in vitro assay:
  GK activator that shifts the $S_{0.5}$ of glucokinase by 90% or more is full activator; and
  GK activator that shifts the $S_{0.5}$ of glucokinase ranging between 20% and 90% is classified as partial activator of glucokinase.

Another aspect of this disclosure is to provide a method of identifying partial glucokinase activators of formula (I), said method comprising
  i. determining the dose dependent effect of a glucokinase activator on % $\Delta S_{0.5}$ and obtain $EC_{50}$ and $E_{max}$ values;
  ii. comparing the $E_{max}$ obtained, with a well-characterized full activator of glucokinase known to produce hypoglycemia;
  iii. selecting compounds having $E_{max}$ in the range of 90% to 20% compared to full activators.

$E_{max}$, thus defined, of a partial GK activator should be significantly less than that of the well-characterized full activators. Compounds that shift $S_{0.5}$ of glucokinase more than 90% have been classified here as full activators. Compounds that shift $S_{0.5}$ of glucokinase between 90-20% have been classified as partial activators of glucokinase.

According to yet another embodiment, the present disclosure relates to compounds of formula (I) their polymorphs, stereoisomers, prodrugs, solvates or pharmaceutically acceptable salts and formulations thereof as, which are liver selective Glucokinase activators, useful for the treatment of hyperglycemia, diabetes, obesity, dyslipidemia, metabolic syndrome and like, in mammals and have minimum hypoglycemic potential.

A further embodiment of the disclosure includes a method of treatment of glucokinase activator mediated disease by administering a therapeutically effective amount of a compound of formula (I) to a mammal in need of such treatment.

By "pharmaceutically acceptable salts" as used herein, it covers salts of compounds of formula (I) prepared from pharmaceutically acceptable non-toxic bases or acids including inorganic or organic bases and inorganic or organic acids. Inorganic bases salts include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Salts in the solid form may exist in more than one crystal structure, and may also be in the form of hydrates. When the compound of the present disclosure is basic, salts may be prepared from pharmaceutically acceptable non-toxic acids, including inorganic and organic acids, such as acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are hydrochloric, maleic, phosphoric, citric, hydrobromic, sulfuric, fumaric, and tartaric acids.

By "therapeutically effective amount" in this disclosure, it means an amount of compound of formula (I), its polymorphs, stereoisomers, pharmaceutically acceptable salt, solvate or pro-drug thereof, that is sufficient for effective treatment of obesity and/or type II diabetes. The therapeutically effective amount or dosage of a compound according to this disclosure can vary within wide limits. The dosage will depend on individual requirements in each particular case including the specific compound(s) being administered, the manner of administration, the severity of condition being treated, as well as the patient being treated, which is readily determinable by a person skilled in the art.

In using a compound of formula (I), its polymorphs, stereoisomers, pharmaceutically acceptable salt, solvate or pro-drug thereof, for therapeutic or prophylactic purposes it will generally be administered so that a daily dose in the range, for example, about 0.01 mg to 100 mg per kg body weight is received, given if required in divided doses. In general lower doses will be administered when a parenteral route is employed. Thus, for example, for intravenous administration, a dose in the range, for example, about 0.01 mg to 30 mg per kg body weight will generally be used. Similarly, for administration by inhalation, a dose in the range, for example, about 0.01 mg to 30 mg per kg body weight will be used.

The disclosure also relates to compound of formula (I), or its polymorph, stereoisomer, prodrug, solvate or a pharmaceutically acceptable salt thereof, for treating a disease through Glucokinase activation.

The disclosure also relates to compounds of formula (I), or its polymorph, stereoisomer, prodrug, solvate or a pharmaceutically acceptable salt thereof, for treating a disease through Glucokinase modulation or regulation.

The disclosure also relates to compounds of formula (I), or its polymorph, stereoisomer, prodrug, solvate or a pharmaceutically acceptable salt thereof, for treating a disease through Glucokinase deinhibition.

The disclosure also relates to compounds of formula (I), or its polymorph, stereoisomer, prodrug, solvate or a pharmaceutically acceptable salt thereof, for prophylactic or therapeutic treatment of hyperglycemia or diabetes, particularly type II diabetes.

The disclosure also relates to compounds of formula (I), or its polymorph, stereoisomer, prodrug, solvate or a pharmaceutically acceptable salt thereof, for preventing diabetes, particularly type II diabetes, in a human demonstrating pre-diabetic hyperglycemia or impaired glucose tolerance.

The disclosure also relates to compounds of formula (I), or its polymorph, stereoisomer, prodrug, solvate or a pharmaceutically acceptable salt thereof, for combined treatment or preventing diabetes and obesity.

The disclosure also relates to compounds of formula (I), or its polymorph, stereoisomer, prodrug, solvate or a pharmaceutically acceptable salt thereof, for treating or preventing obesity.

The disclosure also relates to compounds of formula (I), or its polymorph, stereoisomer, prodrug, solvate or a pharmaceutically acceptable salt thereof, for enhancing the secretion of enteroincretins, like GLP-1 and GIP, thereby managing diseases or disorders associated with modulation of secretions of enteroincretins, such as hyperglycemia, insulin resistance, impaired glucose tolerance, obesity, gastric emptying, gastroparesis, satiety, leptin resistance, dyslipidemia, wound healing, diabetic complications, such as nephropathy, retinopathy, neuropathy and cataracts.

The disclosure also relates to the use of compounds of formula (I), or its polymorphs, stereoisomers, pharmaceutically acceptable salt, solvate or pro-drug thereof, in the prophylactic or therapeutic treatment of dyslipidemia.

The disclosure also relates to identifying the compounds of formula (I), its polymorphs, stereoisomers, pharmaceutically acceptable salt, solvate or pro-drug thereof, which are beneficial for the prophylaxis, management, treatment, control of progression, or adjunct treatment of diseases and/or medical conditions where the activation of glucokinase would be beneficial, such as diabetes (both Type-I and Type-II), obesity, dyslipidemia, metabolic syndrome X, and/or diabetes-related complications and as therapeutic and/or prophylactic agents for obesity, metabolic syndrome X incluses Type-II diabetes, obesity, dyslipidemia, hypertension, and atherosclerosis and like.

The disclosure further relates to compounds of formula (I), its polymorphs, stereoisomers, pharmaceutically acceptable salt, solvate or pro-drug thereof, for use in the manufacture of medicament for the treatment of diabetes, obesity, metabolic syndrome X, insulin resistance, impaired glucose tolerance and dyslipidemia.

The disclosure also relates to the use of a compounds of formula (I), its polymorphs, stereoisomers, pharmaceutically acceptable salt, solvate or pro-drug thereof, in the manufacture of a medicament for the activation of Glucokinase.

The disclosure also relates to the use of a compounds of formula (I), its polymorphs, stereoisomers, pharmaceutically acceptable salt, solvate or pro-drug thereof, in the manufacture of a medicament for the prevention of diabetes, particularly type II diabetes, in a human demonstrating pre-diabetic hyperglycemia or impaired glucose tolerance.

The disclosure also relates to a method of prophylactic or therapeutic treatment of hyperglycemia or diabetes, particularly type II diabetes, comprising a step of administering an effective amount of a compound of formula (I), its polymorphs, stereoisomers, pharmaceutically acceptable salt, solvate or pro-drug thereof.

The disclosure also relates to a method for the prevention of diabetes, particularly type II diabetes, in a human demonstrating pre-diabetic hyperglycemia or impaired glucose tolerance comprising a step of administering an effective prophylactic amount of a compound of formula (I), its polymorphs, stereoisomers, pharmaceutically acceptable salt, solvate or pro-drug thereof.

The disclosure also relates to a method of combined treatment of diabetes and obesity by administering an effective amount of a compound of formula (I), its polymorph, stereoisomer, prodrug, solvate or a pharmaceutically acceptable salt thereof, to a mammal in need of such treatment.

The disclosure also relates to the use of a compound of formula (I), its polymorphs, stereoisomers, pharmaceutically acceptable salt, solvate or pro-drug thereof, for the prevention of diabetes, particularly type II diabetes, in a human demonstrating pre-diabetic hyperglycemia or impaired glucose tolerance.

The disclosure also relates to the use of a compound of formula (I), its polymorphs, stereoisomers, pharmaceutically acceptable salt, solvate or pro-drug thereof, for use as medicament, for the prophylactic or therapeutic treatment of hyperglycemia or diabetes, particularly type II diabetes.

The disclosure also relates to the use of a compound of formula (I), its polymorphs, stereoisomers, pharmaceutically acceptable salt, solvate or pro-drug thereof, in the manufacture of a medicament for the prophylactic or therapeutic treatment of hyperglycemia or diabetes, particularly type II diabetes.

The disclosure also relates to the use of a compound of formula (I), its polymorphs, stereoisomers, pharmaceutically acceptable salt, solvate or pro-drug thereof, in the manufacture of a medicament for use in combined treatment or prevention of diabetes and obesity.

The disclosure also relates to the use of a compound of formula (I), its polymorphs, stereoisomers, pharmaceutically acceptable salt, solvate or pro-drug thereof for prophylactic or therapeutic treatment of a disease selected from a group consisting of a disease needing Glucokinase activation, a disease needing Glucokinase deinhibition, hyperglycemia, IGT, Syndrome X, type 2 diabetes, type 1 diabetes, dyslipidemia, hyperlipidemia, hypertension, insulin resistance, impaired glucose tolerance, obesity, gastric emptying, gastroparesis, satiety, leptin resistance, dyslipidemia, wound healing, nephropathy, retinopathy, neuropathy and cataracts.

The disclosure also relates to the use of a compound of formula (I), its polymorphs, stereoisomers, pharmaceutically acceptable salt, solvate or pro-drug thereof for lowering of food intake, for appetite regulation, for regulating feeding behaviour, for enhancing the secretion of enteroincretins like GLP-1 and GIP, and as a partial activator of glucokinase wherein the Emax is in the range of 60-90%.

The disclosure also relates to the use of a compound of formula (I), its polymorphs, stereoisomers, pharmaceutically acceptable salt, solvate or pro-drug thereof for preventing diabetes, particularly type II diabetes, in a human demonstrating pre-diabetic hyperglycemia or impaired glucose tolerance, preventing obesity and preventing dyslipidemia.

The disclosure also relates to the use of a compound of formula (I), its polymorphs, stereoisomers, pharmaceutically acceptable salt, solvate or pro-drug thereof for combined treatment or prevention of diabetes and obesity.

The compounds and compositions of the present disclosure may be optionally employed in combination with one or more, from current or future therapy, other anti-diabetic agents or anti-hyperglycemic agents, which include, for example, (a) insulin secretagogues such as sulfonylureas (e.g. Amaryl, glyburide, glimepiride, glipyride, glipizide, etc.); (b) Insulinotropic sulfonyl urea receptor ligands such as meglitinides (e.g. nateglinide, rapaglinide); (c) biguanides (e.g. metformin, phenformin, buformin, etc.); (d) glucagon antagonists (e.g. a peptide or non-peptide glucagon antagonist); (e) glucosidase inhibitors (e.g. acarbose, miglitol, etc.); (f) glucose sensitive insulinotropic agents (e.g. GLP-1, GLP-1 mimetics e.g Exendin-4); (g) insulin sensitizers (e.g. troglitazone, rosiglitazone, pioglitazone, etc.); (h) Dipeptidyl peptidase-IV inhibitors (e.g. sitagliptin, vildagliptin); and the like. The said additional therapeutic agent is added in a dose range of about 0.01 mg to 100 mg per kg body weight.

The compounds and compositions of the present disclosure may also be optionally employed in combination with one or more, from current or future therapy, anti-obesity agents (e.g. sibutramine, orlistat, rimonabant etc.) and the like.

The compounds and compositions of the present disclosure may also be optionally employed in combination with one or more, from current or future therapy, dyslipidemic agents which include, for example: (a) fibrates (e.g. gemfibrozil, fenofibrate); (b) Niacin; (c) Statins (e.g. rosuvatatin, atorvastatin, simvastatin); (d) cholesterol absorption inhibitors (e.g. Ezetimibe); (e) bile acid sequestrants (e.g. cholestyramine) and the likes.

The compounds and compositions of the present disclosure may also be optionally employed in combination with one or more, from current or future therapy, antihypertensive agents such as: (a) diuretics (e.g hydrochlorothiazides, mannitol, indapamide, furosemide); (b) angiotensin converting enzyme (ACE) inhibitors (e.g. captopril, enalapril); (c) Angiotensin-II receptor type-I blockers (ARB) (e.g. losartan, irbesartan); (d) rennin inhibitors (e.g aliskerin); (e) β-adrenergic receptor blockers (e.g. atenolol, metoprolol); (f) calcium channel blockers (e.g. amlodipine, nifedipine); (g) aldosterone receptor antagonist (e.g. spironolactone); (h) aldosterone synthase inhibitors (e.g. FAD286). The said additional therapeutic agent is added in a dose range of about 0.01 mg to 100 mg per kg body weight.

The compounds and compositions of the present disclosure and the other therapeutic agents such as described above may be administered simultaneously, sequentially or separately.

The pharmaceutical compositions of the present disclosure comprise a compound of formula (I), polymorphs, stereoisomers, pharmaceutically acceptable salt, solvate or pro-drug thereof, as an active ingredient, a pharmaceutically acceptable carrier and optionally other therapeutic active agent in any suitable ratios. Such therapeutic active agents may be selected from antidiabetic agents, antihyperlipidemic agents, antiobesity agents, antihypertensive agents and agents for the treatment of complications resulting from or associated with diabetes.

The pharmaceutical compositions of the present disclosure comprising compounds of formula (I), polymorphs, stereoisomers, pharmaceutically acceptable salt, solvate or prodrugs thereof, may be manufactured in a manner that is known in the art, e.g. by means of conventional mixing, encapsulating, dissolving, granulating, emulsifying, entrapping, dragee making, or lyophilizing processes. These pharmaceutical preparations can be formulated with therapeutically inert, inorganic or organic carriers such as lactose, corn starch or derivatives thereof, talc, steric acid or its salts as carriers for tablets, coated tablets, dragees and hard gelatin capsules. For soft gelatin capsules suitable carriers include vegetable oils, waxes and fats. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semiliquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula (I), its polymorphs, stereoisomers, pharmaceutically acceptable salt, solvate or prodrugs thereof.

The pharmaceutical compositions containing the active ingredient of compound of formula (I), its polymorphs, stereoisomers, pharmaceutically acceptable salt, solvate or prodrugs thereof, maybe in a form suitable for oral use, for example, as tablets, troches, lozenges, aqueous or oily suspensions, dispersible powders or granules, emulsions, hard or soft capsules, or syrups or elixirs; sterile injectable aqueous or oleaginous suspension; suppositories; topical use, for example creams, ointments, jellies, solutions or suspension etc including mouth washes and gargles. These compositions can be manufactured by any method known in the art with the active ingredient combined with non-toxic pharmaceutically acceptable excipients.

While the disclosure has been described and illustrated with reference to certain preferred embodiments thereof, those skilled in the art will appreciate that various changes, modifications and substitutions can be made therein without departing from the spirit and scope of the present disclosure. For example, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present disclosure.

ABBREVIATIONS

The following abbreviations are employed in the examples and elsewhere herein:

BOP-Cl: Bis(2-oxo-3-oxazolidinyl)phosphinic chloride

DABCO: 1,4-Diazabicyclo[2.2.2]octane

DBU: 1,8-Diazabicyclo[5.4.0]undec-7-ene

DCC: N,N-Dicyclohexyl carbodiimide

EDCI: 1-Ethyl-3-(3-dimetylaminopropyl)carbodiimide

HOBT: 1-Hydroxybenzotriazole

EXAMPLES

The disclosure is further illustrated by the following examples which in no way should be construed as being further limiting. One skilled in the art will readily appreciate that the specific methods and results described are merely illustrative. All stereoisomers of the compounds of the instant disclosure are contemplated, either in admixture or in pure or substantially pure form. The compounds of the present disclosure can have asymmetric centers at any of the carbon atoms, consequently, compounds of formula (I) can exist in enantiomeric, or diastereomeric forms, or in mixtures thereof. The processes for preparation can utilize racemates, enantiomers, or diastereomers as starting materials. When diastereomeric or enantiomeric products are obtained as mixtures, they can be separated by conventional methods for example, chromatographic or fractional crystallization.

Structures of the intermediates as well as the final compounds were confirmed by nuclear magnetic resonance spectra for proton (1H NMR) and LCMS.

Example (A1)

4-Cyclopentylmethyl-1-(2,4-difluoro-benzyl)-1H-pyrrole-2-carboxylic acid (5-chloro-thiazol-2-yl)-amide

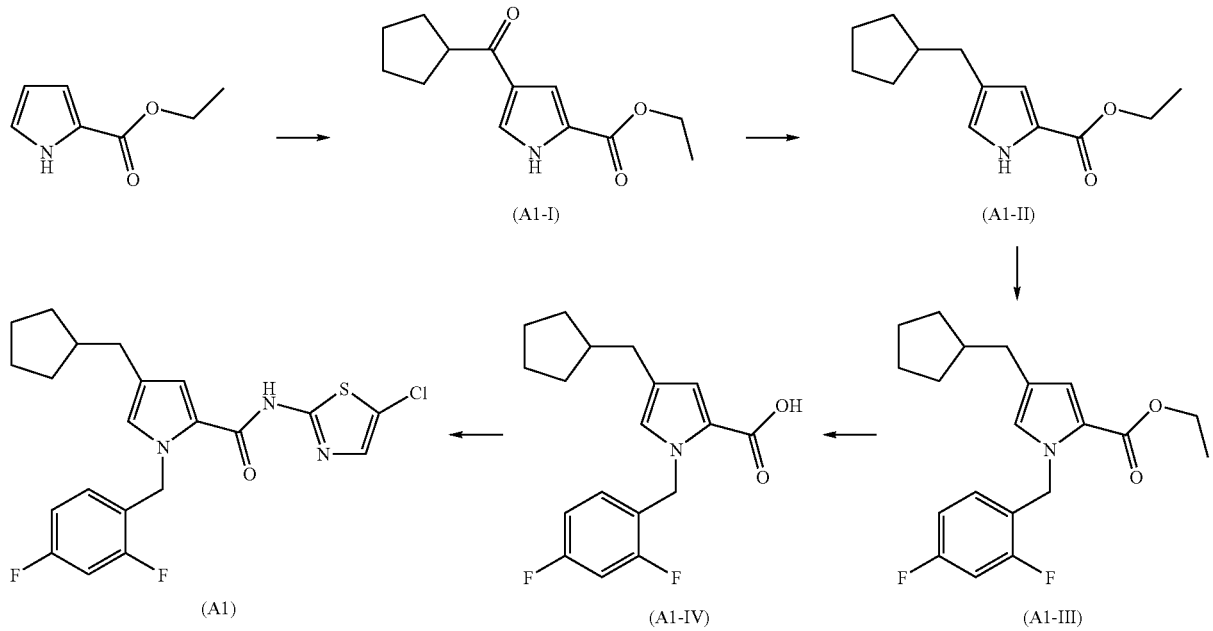

4-Cyclopentanecarbonyl-1-H-pyrrole-2-carboxylic acid ethyl ester (A1-I)

A mixture of cyclopentanecarbonyl chloride and aluminum chloride in dry DCM were stirred in an inert atmosphere at 0-5° C. for 15 minutes. To this, a solution of 1H-pyrrole-2-carboxylic acid ethyl ester in dry DCM was added drop wise under stirring at 0-5° C., stirred further at room temperature for 4 hrs. After completion of reaction, the reaction mixture was poured into ice water and extracted with DCM, DCM layer was washed with 1N NaOH followed by water and brine. The organic layer was dried over anhydrous sodium sulfate and was evaporated to get 4-Cyclopentanecarbonyl-1-H-pyrrole-2-carboxylic acid ethyl ester (A1-I).
$^1$H NMR (400 MHz, CDCl$_3$): δ 1.38 (t, J=7.2 Hz, 3H), 1.64-1.66 (m, 2H), 1.71-1.75 (m, 2H), 1.88-1.93 (m, 4H), 3.40-3.46 (m, 1H), 4.35 (q, J=7.2 Hz, 2H), 7.30-7.31 (m, 1H), 7.54-7.55 (m, 1H).

4-Cyclopentylmethyl-1-H-pyrrole-2-carboxylic acid ethyl ester (A1-II)

To a mixture of 4-cyclopentanecarbonyl-1H-pyrrole-2-carboxylic acid methyl ester (A1-I) and trifluoroacetic acid was added triethylsilylhydride drop wise under stirring at 0-5° C. Stirring was further continued for 20 hours at 0-25° C. Trifluoroacetic acid was removed under reduced pressure and the residue was diluted with diethyl ether, ether layer was separated and washed with 1N NaOH followed by brine, organic layer was dried over anhydrous sodium sulfate and was evaporated to yield 4-cyclopentylmethyl-1-H-pyrrole-2-carboxylic acid ethyl ester (A1-II).
$^1$H NMR (400 MHz, CDCl$_3$): δ 1.13-1.22 (m, 2H), 1.34 (t, J=6.8 Hz, 3H), 1.49-1.54 (m, 2H), 1.55-1.66 (m, 2H), 1.70-1.78 (m, 2H), 1.99-2.07 (m, 1H), 2.45 (d, J=7.6 Hz 2H), 4.30 (q, J=6.8 Hz, 2H), 6.72 (s, 1H), 6.75 (s, 1H), 8.95 (bs, 1H).

MS (EI) m/z: 222 (M+1).

4-Cyclopentylmethyl-1-(2,4-difluorobenzyl)-1H-pyrrole-2-carboxylic acid ethyl ester (A1-III)

A mixture of 4-cyclopentylmethyl-1H-pyrrole-2-carboxylic acid ethyl ester (A1-II) and cesium carbonate were stirred in dry DMF for 10 minutes at 40-50° C. To it 1-bromomethyl-2,4-difluorobenzene was added and the reaction was stirred for 18 hrs. at 50° C. Water was added to the reaction and extracted with ethyl acetate. The organic layer was washed with brine and dried over anhydrous sodium sulfate. The solvent was evaporated to obtain 4-cyclopentylmethyl-1-(2,4-difluorobenzyl)-1H-pyrrole-2-carboxylic acid ethyl ester (A1-III).
$^1$H NMR (400 MHz, CDCl$_3$): δ 1.12-1.21 (m, 2H), 1.30 (t, J=7.2 Hz, 3H), 1.49-1.54 (m, 2H), 1.57-1.65 (m, 2H), 1.70-1.77 (m, 2H), 1.98-2.05 (m, 1H), 2.4 (d, J=7.2 Hz, 2H), 4.22 (q, J=7.2 Hz, 2H), 5.51 (s, 2H), 6.69 (s, 1H), 6.74-6.84 (m, 3H), 6.86-6.93 (m, 1H).

MS (EI) m/z: 348 (M+1).

4-Cyclopentylmethyl-1-(2,4-difluorobenzyl)-1H-pyrrole-2-carboxylic acid (A1-IV)

4-Cyclopentylmethyl-1-(2,4-difluorobenzyl)-1H-pyrrole-2-carboxylic acid ethyl ester (A1-III) was taken in ethanol. To it a solution of potassium hydroxide in water was added and the reaction was refluxed for 18 hrs. Ethanol was evaporated; residue was diluted with water and washed with diethyl ether. The aqueous layer was acidified using dilute HCl and extracted with ethyl acetate. Ethyl acetate layer was washed with brine and dried over anhydrous sodium sulfate. Solvent was evaporated to get 4-cyclopentylmethyl-1-(2,4-difluorobenzyl)-1H-pyrrole-2-carboxylic acid (A1-IV).

¹H NMR (400 MHz, CDCl₃): δ 1.11-1.20 (m, 2H), 1.49-1.53 (m, 2H), 1.57-1.63 (m, 2H), 1.69-1.77 (m, 2H), 1.97-2.05 (m, 1H), 2.41 (d, J=7.2 Hz, 2H), 5.50 (s, 1H), 6.75-6.84 (m, 3H), 6.92-6.98 (m, 2H).

MS (EI) m/z: 320 (M+1).

4-Cyclopentylmethyl-1-(2,4-difluoro-benzyl)-1H-pyrrole-2-carboxylic acid (5-chloro-thiazol-2-yl)-amide (A1)

4-Cyclopentylmethyl-1-(2,4-difluorobenzyl)-1H-pyrrole-2-carboxylic acid (A1-IV) was dissolved in dichloroethane and a drop of DMF was added at 0-5° C. followed by addition of thionyl chloride. Reaction mixture was heated at 70-80° C. for 3-4 hrs. 1,2 dichloroethane was evaporated completely in inert atmosphere. The acid chloride formed was added to a mixture of 4-chloro 2-aminothiazol in 1,2 dichloroethane and pyridine under stirring at 0-5° C. The reaction was further stirred for 4-5 hrs at 40° C. Water was added to the reaction mixture; organic layer was washed with brine and dried over anhydrous sodium sulfate. Solvent was evaporated to provide a residue which was purified by column chromatography to provide the title compound.

¹H NMR (400 MHz, CDCl₃): δ 1.12-1.19 (m, 2H), 1.50-1.55 (m, 2H), 1.58-1.63 (m, 2H) 1.69-1.76 (m, 2H), 1.99-2.01 (m, 1H), 2.41 (d, J=7.2 Hz, 2H), 6.71-6.85 (m, 4H), 7.10-7.14 (m, 1H), 7.21 (s, 1H), 9.95 (bs, 1H).

MS (EI) m/z: 436 (M+1).

Examples A2 to A125 Were Prepared in Analogues Manner of Example (A1) from the Appropriate Intermediate

| Example No. | IUPAC name |
|---|---|
| A2 | 4-Isobutyl-1-(4-trifluoromethyl-benzyl)-1H-pyrrole-2-carboxylic acid thiazol-2-ylamide |
| A3 | 4-Isobutyl-1-(3-trifluoromethyl-benzyl)-1H-pyrrole-2-carboxylic acid thiazol-2-ylamide |
| A4 | 4-Isobutyl-1-(3-nitro-benzyl)-1H-pyrrole-2-carboxylic acid thiazol-2-ylamide |
| A5 | 4-(3-Methyl-butyl)-1-(4-trifluoromethyl-benzyl)-1H-pyrrole-2-carboxylic acid thiazol-2-ylamide |
| A6 | 4-(3-Methyl-butyl)-1-(3-nitro-benzyl)-1H-pyrrole-2-carboxylic acid thiazol-2-ylamide |
| A7 | 4-Isobutyl-1-(4-trifluoromethyl-benzyl)-1H-pyrrole-2-carboxylic acid (5-chloro-thiazol-2-yl)-amide |
| A8 | 4-Isobutyl-1-(3-trifluoromethyl-benzyl)-1H-pyrrole-2-carboxylic acid (5-chloro-thiazol-2-yl)-amide |
| A9 | 4-Isobutyl-1-(3-nitro-benzyl)-1H-pyrrole-2-carboxylic acid (5-chloro-thiazol-2-yl)-amide |
| A10 | 4-(3-Methyl-butyl)-1-(4-trifluoromethylbenzyl)-1H-pyrrole-2-carboxylic acid (5-chloro-thiazol-2-yl)-amide |
| A11 | 4-(3-Methyl-butyl)-1-(3-nitro-benzyl)-1H-pyrrole-2-carboxylic acid (5-chloro-thiazol-2-yl)-amide |
| A12 | 4-(4-Chloro-benzyl)-1-(4-trifluoromethyl-benzyl)-1H-pyrrole-2-carboxylic acid thiazol-2-ylamide |
| A13 | 4-(4-Chloro-benzyl)-1-(4-trifluoromethyl-benzyl)-1H-pyrrole-2-carboxylic acid (5-chloro-thiazol-2-yl)-amide |
| A14 | 4-(4-Chloro-benzyl)-1-(3-trifluoromethyl-benzyl)-1H-pyrrole-2-carboxylic acid thiazol-2-ylamide |
| A15 | 4-(4-Chloro-benzyl)-1-(3-trifluoromethyl-benzyl)-1H-pyrrole-2-carboxylic acid (5-chloro-thiazol-2-yl)-amide |
| A16 | 4-(4-Chloro-benzyl)-1-(3-nitro-benzyl)-1H-pyrrole-2-carboxylic acid thiazol-2-ylamide |
| A17 | 4-(4-Chloro-benzyl)-1-(3-nitro-benzyl)-1H-pyrrole-2-carboxylic acid (5-chloro-thiazol-2-yl)-amide |
| A18 | 4-Isobutyl-1-(4-nitro-benzyl)-1H-pyrrole-2-carboxylic acid thiazol-2-ylamide |
| A19 | 4-(3-Methyl-butyl)-1-(3-trifluoromethylbenzyl)-1H-pyrrole-2-carboxylic acid (5-chloro-thiazol-2-yl)-amide |
| A20 | 1-(2,4-Difluoro-benzyl)-4-isobutyl-1H-pyrrole-2-carboxylic acid (5-chloro-thiazol-2-yl)-amide |
| A21 | 4-(4-Chloro-benzyl)-1-cyclopentylmethyl-1H-pyrrole-2-carboxylic acid thiazol-2-ylamide |
| A22 | 4-(4-Chloro-benzyl)-1-cyclopentylmethyl-1H-pyrrole-2-carboxylic acid (5-chloro-thiazol-2-yl)-amide |
| A23 | 4-(4-Chloro-benzyl)-1-(2-thiophen-3-yl-ethyl)-1H-pyrrole-2-carboxylic acid thiazol-2-ylamide |
| A24 | 4-(4-Chloro-benzyl)-1-(2,4-difluoro-benzyl)-1H-pyrrole-2-carboxylic acid thiazol-2-ylamide |
| A25 | 1-(2,4-Difluoro-benzyl)-4-(3-methyl-butyl)-1H-pyrrole-2-carboxylic acid (5-chloro-thiazol-2-yl)-amide |
| A26 | 4-Isobutyl-1-(3-trifluoromethyl-benzyl)-1H-pyrrole-2-carboxylic acid benzothiazol-2-ylamide |
| A27 | 4-Isobutyl-1-(3-trifluoromethyl-benzyl)-1H-pyrrole-2-carboxylic acid (6-fluorobenzothiazol-2-yl)-amide |
| A28 | 4-Isobutyl-1-(3-trifluoromethyl-benzyl)-1H-pyrrole-2-carboxylic acid (4-phenyl-thiazol-2-yl)-amide |
| A29 | 1-(4-Fluoro-3-trifluoromethyl-benzyl)-4-isobutyl-1H-pyrrole-2-carboxylic acid (6-fluoro-benzothiazol-2-yl)-amide |

| Example No. | IUPAC name |
| --- | --- |
| A30 | 1-(4-Fluoro-3-trifluoromethyl-benzyl)-4-isobutyl-1H-pyrrole-2-carboxylic acid benzothiazol-2-ylamide |
| A31 | 1-(4-Fluoro-3-trifluoromethyl-benzyl)-4-isobutyl-1H-pyrrole-2-carboxylic acid (5-chloro-thiazol-2-yl)-amide |
| A32 | 1-(2-Fluoro-3-trifluoromethyl-benzyl)-4-isobutyl-1H-pyrrole-2-carboxylic acid benzothiazol-2-ylamide |
| A33 | 4-Isobutyl-1-(2-thiophen-3-yl-ethyl)-1H-pyrrole-2-carboxylic acid benzothiazol-2-ylamide |
| A34 | 4-Isobutyl-1-(2-thiophen-3-yl-ethyl)-1H-pyrrole-2-carboxylic acid thiazol-2-ylamide |
| A35 | 1-(4-Fluoro-3-trifluoromethyl-benzyl)-4-isobutyl-1H-pyrrole-2-carboxylic acid thiazol-2-ylamide |
| A36 | 1-(2,4-Difluoro-benzyl)-4-isobutyl-1H-pyrrole-2-carboxylic acid thiazol-2-ylamide |
| A37 | 4-Isobutyl-1-(2-thiophen-2-yl-ethyl)-1H-pyrrole-2-carboxylic acid thiazol-2-ylamide |
| A38 | 1-(2,4-Difluoro-benzyl)-4-isobutyl-1H-pyrrole-2-carboxylic acid (5-fluoro-thiazol-2-yl)-amide |
| A39 | 1-(3,4-Difluoro-benzyl)-4-isobutyl-1H-pyrrole-2-carboxylic acid thiazol-2-ylamide |
| A40 | 1-(3,4-Difluoro-benzyl)-4-isobutyl-1H-pyrrole-2-carboxylic acid (5-chloro-thiazol-2-yl)-amide |
| A41 | 1-(3,4-Dichloro-benzyl)-4-isobutyl-1H-pyrrole-2-carboxylic acid thiazol-2-ylamide |
| A42 | 1-(3,4-Dichloro-benzyl)-4-isobutyl-1H-pyrrole-2-carboxylic acid (5-chloro-thiazol-2-yl)-amide |
| A43 | 1-(3,4-Difluoro-benzyl)-4-isobutyl-1H-pyrrole-2-carboxylic acid (5-fluoro-thiazol-2-yl)-amide |
| A44 | 4-Isobutyl-1-(2-thiophen-3-yl-ethyl)-1H-pyrrole-2-carboxylic acid (5-chloro-thiazol-2-yl)-amide |
| A45 | 4-Cyclopentylmethyl-1-(2,4-difluoro-benzyl)-1H-pyrrole-2-carboxylic acid thiazol-2-ylamide |
| A46 | 4-Cyclopentylmethyl-1-(2,4-difluoro-benzyl)-1H-pyrrole-2-carboxylic acid (5-fluoro-thiazol-2-yl)-amide |
| A47 | 4-Cyclopentylmethyl-1-(3,5-difluoro-benzyl)-1H-pyrrole-2-carboxylic acid thiazol-2-ylamide |
| A48 | 4-Cyclopentylmethyl-1-(3,5-difluoro-benzyl)-1H-pyrrole-2-carboxylic acid (5-chloro-thiazol-2-yl)-amide |
| A49 | 4-Cyclopentylmethyl-1-(3,5-difluoro-benzyl)-1H-pyrrole-2-carboxylic acid (5-fluoro-thiazol-2-yl)-amide |
| A50 | 1-(2,4-Difluoro-benzyl)-4-ethyl-1H-pyrrole-2-carboxylic acid thiazol-2-ylamide |
| A51 | 1-(2,4-Difluoro-benzyl)-4-ethyl-1H-pyrrole--2-carboxylic acid (5-chloro-thiazol-2-yl)-amide |
| A52 | 1-(2,4-Difluoro-benzyl)-4-ethyl-1H-pyrrole-2-carboxylic acid (5-fluoro-thiazol-2-yl)-amide |
| A53 | 1-(4-Fluoro-benzyl)-4-isobutyl-1H-pyrrole-2-carboxylic acid (5-chloro-thiazol-2-yl)-amide |
| A54 | 1-(3,5-Difluoro-benzyl)-4-ethyl-1H-pyrrole-2-carboxylic acid thiazol-2-ylamide |
| A55 | 1-(3,5-Difluoro-benzyl)-4-ethyl-1H-pyrrole-2-carboxylic acid (5-chloro-thiazol-2-yl)-amide |
| A56 | 1-(2,4-Difluoro-benzyl)-4-isobutyl-1H-pyrrole-2-carboxylic acid (4-methyl-thiazol-2-yl)-amide |
| A57 | 1-(2,4-Difluoro-benzyl)-4-isobutyl-1H-pyrrole-2-carboxylic acid (5-methyl-thiazol-2-yl)-amide |
| A58 | 1-(4-Fluoro-3-trifluoromethyl-benzyl)-4-isobutyl-1H-pyrrole-2-carboxylic acid (5-fluoro-thiazol-2-yl)-amide |
| A59 | 1-[2-(3,4-Difluoro-phenoxy)-ethyl]-4-isobutyl-1H-pyrrole-2-carboxylic acid thiazol-2-ylamide |
| A60 | 1-[2-(3,4-Difluoro-phenoxy)-ethyl]-4-isobutyl-1H-pyrrole-2-carboxylic acid (5-chloro-thiazol-2-yl)-amide |
| A61 | 1-[1-(4-Fluoro-phenyl)-ethyl]-4-isobutyl-1H-pyrrole-2-carboxylic acid thiazol-2-ylamide |
| A62 | 1-[1-(4-Fluoro-phenyl)-ethyl]-4-isobutyl-1H-pyrrole-2-carboxylic acid (5-chloro-thiazol-2-yl)-amide |
| A63 | 1-[1-(4-Fluoro-phenyl)-ethyl]-4-isobutyl-1H-pyrrole-2-carboxylic acid (5-fluoro-thiazol-2-yl)-amide |
| A64 | 1-[2-(2,4-Difluoro-phenyl)-ethyl]-4-isobutyl-1H-pyrrole-2-carboxylic acid thiazol-2-ylamide |
| A65 | 4-Isobutyl-1-(2,3,4-trifluoro-benzyl)-1H-pyrrole-2-carboxylic acid thiazol-2-ylamide |
| A66 | 4-Isobutyl-1-(2,3,4-trifluoro-benzyl)-1H-pyrrole-2-carboxylic acid (5-chloro-thiazol-2-yl)-amide |
| A67 | 1-(4-Chloro-3-trifluoromethyl-benzyl)-4-isobutyl-1H-pyrrole-2-carboxylic acid thiazol-2-ylamide |
| A68 | 1-(4-Chloro-3-trifluoromethyl-benzyl)-4-isobutyl-1H-pyrrole-2-carboxylic acid (5-chloro-thiazol-2-yl)-amide |

-continued

| Example No. | IUPAC name |
|---|---|
| A69 | 1-(2,6-Difluoro-benzyl)-4-isobutyl-1H-pyrrole-2-carboxylic acid thiazol-2-ylamide |
| A70 | 1-(2,6-Difluoro-benzyl)-4-isobutyl-1H-pyrrole-2-carboxylic acid (5-chloro-thiazol-2-yl)-amide |
| A71 | 1-(3-Chloro-benzyl)-4-isobutyl-1H-pyrrole-2-carboxylic acid thiazol-2-ylamide |
| A72 | 1-(3-Chloro-benzyl)-4-isobutyl-1H-pyrrole-2-carboxylic acid (5-chloro-thiazol-2-yl)-amide |
| A73 | 1-(3-Fluoro-benzyl)-4-isobutyl-1H-pyrrole-2-carboxylic acid thiazol-2-ylamide |
| A74 | 1-(3-Fluoro-benzyl)-4-isobutyl-1H-pyrrole-2-carboxylic acid (5-chloro-thiazol-2-yl)-amide |
| A75 | 1-(2-Chloro-5-fluoro-benzyl)-4-isobutyl-1H-pyrrole-2-carboxylic acid thiazol-2-ylamide |
| A76 | 1-(2-Chloro-5-fluoro-benzyl)-4-isobutyl-1H-pyrrole-2-carboxylic acid (5-chloro-thiazol-2-yl)-amide |
| A77 | 4-Isobutyl-1-[2-(4-methanesulfonyl-phenyl)-ethyl]-1H-pyrrole-2-carboxylic acid thiazol-2-ylamide |
| A78 | 4-Isobutyl-1-(4-methanesulfonyl-benzyl)-1H-pyrrole-2-carboxylic acid thiazol-2-ylamide |
| A79 | 4-Isobutyl-1-(4-methanesulfonyl-benzyl)-1H-pyrrole-2-carboxylic acid (5-chloro-thiazol-2-yl)-amide |
| A80 | 1-(3-Fluoro-4-trifluoromethyl-benzyl)-4-isobutyl-1H-pyrrole-2-carboxylic acid thiazol-2-ylamide |
| A81 | 1-(3-Fluoro-4-trifluoromethyl-benzyl)-4-isobutyl-1H-pyrrole-2-carboxylic acid (5-chloro-thiazol-2-yl)-amide |
| A82 | 4-Isobutyl-1-(4-methylsulfanyl-benzyl)-1H-pyrrole-2-carboxylic acid thiazol-2-ylamide |
| A83 | 1-(3,4-Difluoro-benzyl)-4-ethyl-1H-pyrrole-2-carboxylic acid thiazol-2-ylamide |
| A84 | 1-(3,4-Difluoro-benzyl)-4-ethyl-1H-pyrrole-2-carboxylic acid (5-chloro-thiazol-2-yl)-amide |
| A85 | 1-(3-Chloro-5-fluoro-benzyl)-4-isobutyl-1H-pyrrole-2-carboxylic acid thiazol-2-ylamide |
| A86 | 1-(3-Chloro-5-fluoro-benzyl)-4-isobutyl-1H-pyrrole-2-carboxylic acid (5-chloro-thiazol-2-yl)-amide |
| A87 | 1-(4-Chloro-benzyl)-4-isobutyl-1H-pyrrole-2-carboxylic acid thiazol-2-ylamide |
| A88 | 1-(4-Chloro-benzyl)-4-isobutyl-1H-pyrrole-2-carboxylic acid (5-chloro-thiazol-2-yl)-amide |
| A89 | 1-(2,3-Difluoro-benzyl)-4-isobutyl-1H-pyrrole-2-carboxylic acid thiazol-2-ylamide |
| A90 | 1-(2,3-Difluoro-benzyl)-4-isobutyl-1H-pyrrole-2-carboxylic acid (5-chloro-thiazol-2-yl)-amide |
| A91 | 1-Benzyl-4-isobutyl-1H-pyrrole-2-carboxylic acid (5-chloro-thiazol-2-yl)-amide |
| A92 | 4-Isobutyl-1-(thiophene-2-sulfonyl)-1H-pyrrole-2-carboxylic acid (5-chloro-thiazol-2-yl)-amide |
| A93 | 4-Isobutyl-1-(2,3,6-trifluoro-benzyl)-1H-pyrrole-2-carboxylic acid (5-chloro-thiazol-2-yl)-amide |
| A94 | 1-(2-Chloro-6-fluoro-benzyl)-4-isobutyl-1H-pyrrole-2-carboxylic acid thiazol-2-ylamide |
| A95 | 1-(2-Chloro-6-fluoro-benzyl)-4-isobutyl-1H-pyrrole-2-carboxylic acid (5-chloro-thiazol-2-yl)-amide |
| A96 | 1-(2,5-Dichloro-benzyl)-4-isobutyl-1H-pyrrole-2-carboxylic acid thiazol-2-ylamide |
| A97 | 1-(2,5-Dichloro-benzyl)-4-isobutyl-1H-pyrrole-2-carboxylic acid (5-chloro-thiazol-2-yl)-amide |
| A98 | 1-(3,4-Difluoro-benzyl)-4-propyl-1H-pyrrole-2-carboxylic acid thiazol-2-ylamide |
| A99 | 1-(3,4-Difluoro-benzyl)-4-propyl-1H-pyrrole-2-carboxylic acid (5-chloro-thiazol-2-yl)-amide |
| A100 | 1-(3-Chloro-4-fluoro-benzyl)-4-isobutyl-1H-pyrrole-2-carboxylic acid (5-chloro-thiazol-2-yl)-amide |
| A101 | 1-(4-Chloro-3-fluoro-benzyl)-4-isobutyl-1H-pyrrole-2-carboxylic acid (5-chlorothiazol-2-yl)-amide |
| A102 | 4-Isobutyl-1-(4-methanesulfonyl-benzyl)-1H-pyrrole-2-carboxylic acid (5-fluorothiazol-2-yl)-amide |
| A103 | 1-(3,4-Difluoro-benzyl)-4-isobutyl-1H-pyrrole-2-carboxylic acid (4-trifluoromethyl-thiazol-2-yl)-amide |
| A104 | 1-(3,4-Difluoro-benzyl)-4-isobutyl-1H-pyrrole-2-carboxylic acid (1-methyl-5-oxo-4,5-dihydro-1H-imidazol-2-yl)-amide |
| A105 | 1-(4-Cyclopropanesulfonyl-benzyl)-4-isobutyl-1H-pyrrole-2-carboxylic acid (5-chloro-thiazol-2-yl)-amide |
| A106 | 1-(4-Cyclopropanesulfonyl-benzyl)-4-isobutyl-1H-pyrrole-2-carboxylic acid (5-fluoro-thiazol-2-yl)-amide |
| A107 | 1-(3,4-Difluoro-benzyl)-4-(4-methanesulfonyl-benzyl)-1H-pyrrole-2-carboxylic acid (5-fluoro-thiazol-2-yl)-amide |

-continued

| Example No. | IUPAC name |
| --- | --- |
| A108 | (5-Chloro-2-{[1-(4-fluoro-3-trifluoromethyl-benzyl)-4-isobutyl-1H-pyrrole-2-carbonyl]-amino}-thiazol-4-yl)-acetic acid ethyl ester |
| A109 | 6-{[1-(4-Fluoro-3-trifluoromethyl-benzyl)-4-isobutyl-1H-pyrrole-2-carbonyl]-amino}-nicotinic acid methyl ester |
| A110 | (2-{[1-(2,4-Difluoro-benzyl)-4-isobutyl-1H-pyrrole-2-carbonyl]-amino}-thiazol-4-yl)-acetic acid ethyl ester |
| A111 | 6-{[1-(2,4-Difluoro-benzyl)-4-isobutyl-1H-pyrrole-2-carbonyl]-amino}-nicotinic acid methyl ester |
| A112 | (2-{[1-(4-Fluoro-3-trifluoromethyl-benzyl)-4-isobutyl-1H-pyrrole-2-carbonyl]-amino}-thiazol-4-yl)-acetic acid ethyl ester |
| A113 | (2-{[4-Isobutyl-1-(2-thiophen-3-yl-ethyl)-1H-pyrrole-2-carbonyl]-amino}-thiazol-4-yl)-acetic acid ethyl ester |
| A114 | (2-{[4-Isobutyl-1-(2-thiophen-2-yl-ethyl)-1H-pyrrole-2-carbonyl]-amino}-thiazol-4-yl)-acetic acid ethyl ester |
| A115 | (5-Chloro-2-{[1-(3,4-dichloro-benzyl)-4-isobutyl-1H-pyrrole-2-carbonyl]-amino}-thiazol-4-yl)-acetic acid ethyl ester |
| A116 | (5-Chloro-2-{[1-(3,4-difluoro-benzyl)-4-isobutyl-1H-pyrrole-2-carbonyl]-amino}-thiazol-4-yl)-acetic acid ethyl ester |
| A117 | 3-(2-{[1-(3,4-Difluoro-benzyl)-4-isobutyl-1H-pyrrole-2-carbonyl]-amino}-thiazol-4-yl)-propionic acid ethyl ester |
| A118 | (5-Chloro-2-{[1-(3-chloro-4-fluoro-benzyl)-4-isobutyl-1H-pyrrole-2-carbonyl]-amino}-thiazol-4-yl)-acetic acid ethyl ester |
| A119 | (5-Chloro-2-{[1-(4-chloro-3-fluoro-benzyl)-4-isobutyl-1H-pyrrole-2-carbonyl]-amino}-thiazol-4-yl)-acetic acid ethyl ester |
| A120 | 6-{[1-(3,4-Difluoro-benzyl)-4-isobutyl-1H-pyrrole-2-carbonyl]-amino}-nicotinic acid methyl ester |
| A121 | (5-Chloro-2-{[4-isobutyl-1-(4-methanesulfonyl-benzyl)-1H-pyrrole-2-carbonyl]-amino}-thiazol-4-yl)-acetic acid ethyl ester |
| A122 | (2-{[4-Isobutyl-1-(4-methanesulfonyl-benzyl)-1H-pyrrole-2-carbonyl]-amino}-thiazol-4-yl)-acetic acid ethyl ester |
| A123 | (5-Chloro-2-{[1-(2,4-difluoro-benzyl)-4-isobutyl-1H-pyrrole-2-carbonyl]-amino}-thiazol-4-yl)-acetic acid ethyl ester |
| A124 | (5-Chloro-2-{[1-(4-cyclopropanesulfonyl-benzyl)-4-isobutyl-1H-pyrrole-2-carbonyl]-amino}-thiazol-4-yl)-acetic acid ethyl ester |
| A125 | (5-Chloro-2-{[1-(3,4-difluoro-benzyl)-4-(4-methanesulfonyl-benzyl)-1H-pyrrole-2-carbonyl]-amino}-thiazol-4-yl)-acetic acid ethyl ester |

Example (B1)

1-(3,4-Difluoro-benzyl)-4-isobutyryl-1H-pyrrole-2-carboxylic acid thiazol-2-ylamide

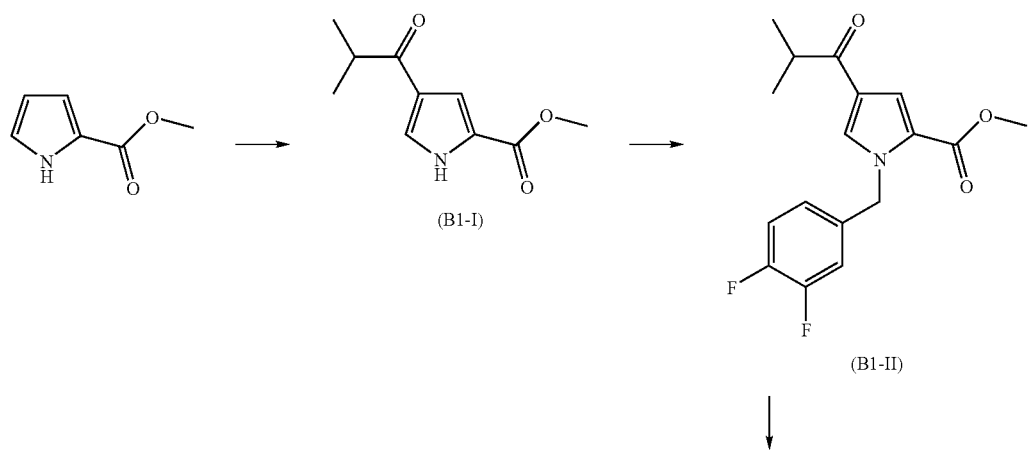

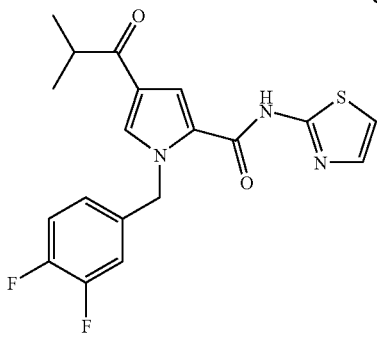

(B1)

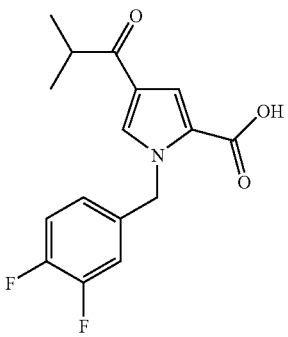

(B1-III)

4-Isobutyryl-1H-pyrrole-2-carboxylic acid methyl ester (B1-I)

A mixture of isobutyryl chloride and aluminum chloride in dry DCM were stirred in an inert atmosphere at 0-5° C. for 15 minutes. To this was added a solution of 1H-pyrrole-2-carboxylic acid methyl ester in dry DCM drop wise under stirring at 0-5° C. and stirred further for 4 hours at room temperature. After completion of reaction, reaction mixture was poured into ice water and extracted with DCM, DCM layer was washed with 1N NaOH followed by water and brine. The organic layer was dried over anhydrous sodium sulfate and was evaporated to get 4-isobutyryl-1H-pyrrole-2-carboxylic acid methyl ester (B1-I)

$^1$H NMR (400 MHz, CDCl$_3$): δ 1.20 (d, J=6.8 Hz, 6H), 3.20-3.23 (m, 1H), 3.90 (s, 3H), 7.31-7.32 (m, 1H), 7.57-7.58 (m, 1H), 9.7 (bs, 1H).

MS (EI) m/z: 196 (M+1).

1-(3,4-Difluoro-benzyl)-4-isobutyryl-1H-pyrrole-2-carboxylic acid methyl ester (B1-II)

A mixture of 4-isobutyryl-1H-pyrrole-2-carboxylic acid methyl ester (B1-I) and cesium carbonate were stirred in dry DMF for 10 minutes at 40-50° C. To it 1-bromomethyl-3,4-difluorobenzene was added and the reaction was stirred for 18 hrs at 50° C. Water was added to the reaction and extracted with ethyl acetate. The organic layer was washed with brine and dried over anhydrous sodium sulfate. The solvent was evaporated to obtain 1-(3,4-difluoro-benzyl)-4-isobutyryl-1H-pyrrole-2-carboxylic acid methyl ester (B1-II).

$^1$H NMR (400 MHz, CDCl$_3$): δ 1.20 (d, J=6.8 Hz, 6H), 3.19-3.22 (m, 1H), 3.82 (s, 3H), 5.52 (s, 2H), 6.89-6.91 (m, 1H), 6.95-7.00 (m, 1H), 7.10-7.14 (m, 1H), 7.40 (d, J=2 Hz, 1H), 7.50 (d, J=2 Hz, 1H)

MS (EI) m/z: 322.1 (M+1).

1-(3,4-difluoro-benzyl)-4-isobutyryl-1H-pyrrole-2-carboxylic acid (B1-III)

1-(3,4-Difluoro-benzyl)-4-isobutyryl-1H-pyrrole-2-carboxylic acid ethyl ester (B1-II) was taken in ethanol. To it a solution of potassium hydroxide in water was added and the reaction was refluxed for 18 hrs. Ethanol was evaporated; residue was diluted with water and washed with diethyl ether. The aqueous layer was acidified using dilute HCl and extracted with ethyl acetate. Ethyl acetate layer was washed with brine and dried over anhydrous sodium sulfate. Solvent was evaporated to get 1-(3,4-difluoro-benzyl)-4-isobutyryl-1H-1-pyrrole-2-carboxylic acid (B1-III).

$^1$H NMR (400 MHz, CDCl$_3$): δ 1.21 (d, J=6.8 Hz, 6H), 3.20-3.23 (m, 1H), 5.52 (s, 2H), 6.90-6.92 (m, 1H), 6.97-7.01 (m, 1H), 7.10-7.17 (m, 1H), 7.52-7.55 (m, 2H).

1-(3,4-Difluoro-benzyl)-4-isobutyryl-1H-pyrrole-2-carboxylic acid thiazol-2-ylamide (B1)

1-(3,4-Difluoro-benzyl)-4-isobutyryl-1H-pyrrole-2-carboxylic acid (B1-III) was dissolved in dichloroethane and a drop of DMF was added at 0-5° C. followed by addition of thionyl chloride. Reaction mixture was heated at 70-80° C. for 3-4 hrs. 1,2 dichloroethane was evaporated in inert atmosphere. The acid chloride formed was added to a mixture of 2-aminothiazol in 1,2 dichloroethane and pyridine under stirring at 0-5° C. The reaction was further stirred for 4-5 hrs at 40° C. Water was added to the reaction mixture; organic layer was washed with brine and dried over anhydrous sodium sulfate. Solvent was evaporated to provide a residue which was purified by column chromatography to provide the title compound (B1)

$^1$H NMR (400 MHz, CDCl$_3$): δ 1.18 (d, J=8.8 Hz, 6H), 3.08-3.16 (m, 1H), 5.63 (s, 2H), 6.98-6.99 (m, 2H), 7.02-7.14 (m, 2H), 7.35 (s, 1H), 7.39 (d, J=3.6 Hz, 1H), 7.51 (s, 1H), 10.6 (bs, 1H).

MS (EI) m/z: 390 (M+1).

Examples B2 to B11 Were Prepared in Analogues Manner of Example (B1) from the Appropriate Intermediate

| Example No. | IUPAC name |
| --- | --- |
| B2 | 4-Cyclopropanecarbonyl-1-(3,4-difluoro-benzyl)-1H-pyrrole-2-carboxylic acid thiazol-2-ylamide |
| B3 | 4-Cyclopropanecarbonyl-1-(3,4-difluorobenzyl)-1H-pyrrole-2-carboxylicacid (5-chloro-thiazol-2-yl)-amide |
| B4 | 1-(3,4-Difluoro-benzyl)-4-isobutyryl-1H-pyrrole-2-carboxylic acid (5-chloro-thiazol-2-yl)-amide |
| B5 | 1-(2,3-Difluoro-benzyl)-4-isobutyryl-1H-pyrrole-2-carboxylic acid (5-chloro-thiazol-2-yl)-amide |
| B6 | (5-Chloro-2-{[1-(3,4-difluoro-benzyl)-4-isobutyryl-1H-pyrrole-2-carbonyl]-amino}-thiazol-4-yl)-acetic acid ethyl ester |
| B7 | (5-Chloro-2-{[1-(4-cyclopropanesulfonyl-benzyl)-4-isobutyryl-1H-pyrrole-2-carbonyl]-amino}-thiazol-4-yl)-acetic acid ethyl ester |

| Example No. | IUPAC name |
| --- | --- |
| B8 | 1-(4-Fluoro-3-trifluoromethyl-benzyl)-4-isobutyryl-1H-pyrrole-2-carboxylic acid thiazol-2-ylamide |
| B9 | 1-(4-Fluoro-3-trifluoromethyl-benzyl)-4-isobutyryl-1H-pyrrole-2-carboxylic acid (5-chloro-thiazol-2-yl)-amide |
| B10 | 1-(4-Fluoro-3-trifluoromethyl-benzyl)-4-isobutyryl-1H-pyrrole-2-carboxylic acid (5-fluoro-thiazol-2-yl)-amide |
| B11 | (5-Chloro-2-{[1-(4-fluoro-3-trifluoromethyl-benzyl)-4-isobutyryl-1H-pyrrole-2-carbonyl]-amino}-thiazol-4-yl)-acetic acid ethyl ester |

Example (C1)

1-(3,4-Difluoro-benzyl)-4-(1-hydroxy-2-methyl-propyl)-1H-pyrrole-2-carboxylic acid thiazol-2-ylamide

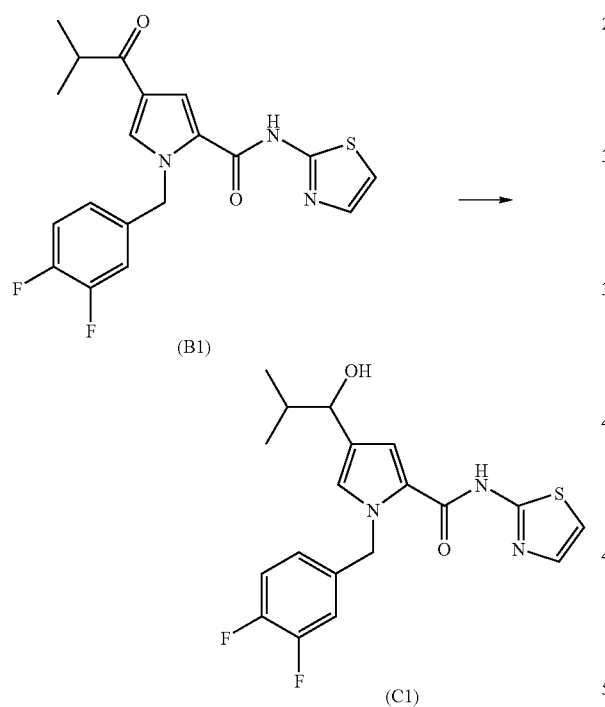

1-(3,4-Difluoro-benzyl)-4-isobutyryl-1H-pyrrole-2-carboxylic acid thiazol-2-amide(B1) was taken in ethanol and to it sodium borohydride was added at 0-5° C. and stirred for 5 hrs. On completion of reaction, saturated ammonium chloride solution was added to the reaction mixture. Ethanol was evaporated and the aqueous layer was extracted with ethyl acetate. The organic layer was washed with brine and dried over anhydrous sodium sulfate. The solvent was evaporated to provide crude product which was purified by preparative TLC to provide 1-(3,4-Difluoro-benzyl)-4-(1-hydroxy-2-methyl-propyl)-1H-pyrrole-2-carboxylic acid thiazol-2-ylamide (C1).

$^1$H NMR (400 MHz, CDCl$_3$): δ 0.88 ((d, J=6.4 Hz, 2H), 0.98 (d, J=6.8 Hz, 2H), 1.92-1.94 (m, 1H), 4.41 (d, J=6.0 Hz, 1H), 5.59 (s, 2H), 6.89-6.91 (m, 3H), 6.95-6.99 (m, 2H), 7.09-7.11 (m, 1H), 7.41-7.42 (m, 1H), 10.2 (bs, 1H). MS (EI) m/z: 392 (M+1).

Examples C2 to C16 Were Prepared in Analogues Manner of Example (C1) from the Appropriate Intermediate

| Example No. | IUPAC name |
| --- | --- |
| C2 | 1-(3,4-Difluoro-benzyl)-4-(1-hydroxy-2-methyl-propyl)-1H-pyrrole-2-carboxylic acid (5-chloro-thiazol-2-yl)-amide |
| C3 | 1-(2,3-Difluoro-benzyl)-4-(1-hydroxy-2-methyl-propyl)-1H-pyrrole-2-carboxylic acid (5-chloro-thiazol-2-yl)-amide |
| C4 | (5-Chloro-2-{[1-(3,4-difluoro-benzyl)-4-(1-hydroxy-2-methyl-propyl)-1H-pyrrole-2-carbonyl]-amino}-thiazol-4-yl)-acetic acid ethyl ester |
| C5 | (5-Chloro-2-{[1-(4-cyclopropanesulfonyl-benzyl)-4-(1-hydroxy-2-methyl-propyl)-1H-pyrrole-2-carbonyl]-amino}-thiazol-4-yl)-acetic acid ethyl ester |
| C6 | 4-(1-Hydroxy-2-methyl-propyl)-1-(4-methanesulfonyl-benzyl)-1H-pyrrole-2-carboxylic acid thiazol-2-ylamide |
| C7 | 4-(1-Hydroxy-2-methyl-propyl)-1-(4-methanesulfonyl-benzyl)-1H-pyrrole-2-carboxylic acid (5-chloro-thiazol-2-yl)-amide |
| C8 | 4-(1-Hydroxy-2-methyl-propyl)-1-(4-methanesulfonyl-benzyl)-1H-pyrrole-2-carboxylic acid (5-fluoro-thiazol-2-yl)-amide |
| C9 | 1-(2,4-Difluoro-benzyl)-4-(1-hydroxy-2-methyl-propyl)-1H-pyrrole-2-carboxylic acid (5-fluoro-thiazol-2-yl)-amide |
| C10 | 1-(4-Cyclopropanesulfonyl-benzyl)-4-(1-hydroxy-2-methyl-propyl)-1H-pyrrole-2-carboxylic acid (5-fluoro-thiazol-2-yl)-amide |
| C11 | 1-(4-Cyclopropanesulfonyl-benzyl)-4-(1-hydroxy-2-methyl-propyl)-1H-pyrrole-2-carboxylic acid (5-chloro-thiazol-2-yl)-amide |
| C12 | 1-(4-Fluoro-3-trifluoromethyl-benzyl)-4-(1-hydroxy-2-methyl-propyl)-1H-pyrrole-2-carboxylic acid thiazol-2-ylamide |
| C13 | 1-(4-Fluoro-3-trifluoromethyl-benzyl)-4-(1-hydroxy-2-methyl-propyl)-1H-pyrrole-2-carboxylic acid (5-chloro-thiazol-2-yl)-amide |
| C14 | 1-(4-Fluoro-3-trifluoromethyl-benzyl)-4-(1-hydroxy-2-methyl-propyl)-1H-pyrrole-2-carboxylic acid (5-fluoro-thiazol-2-yl)-amide |
| C15 | (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester |
| C16 | (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester |

Example (D1)

1-(3,4-Difluoro-benzyl)-4-(thiophene-2-sulfonyl)-1H-pyrrole-2-carboxylic acid (5-chloro-thiazol-2-yl)-amide

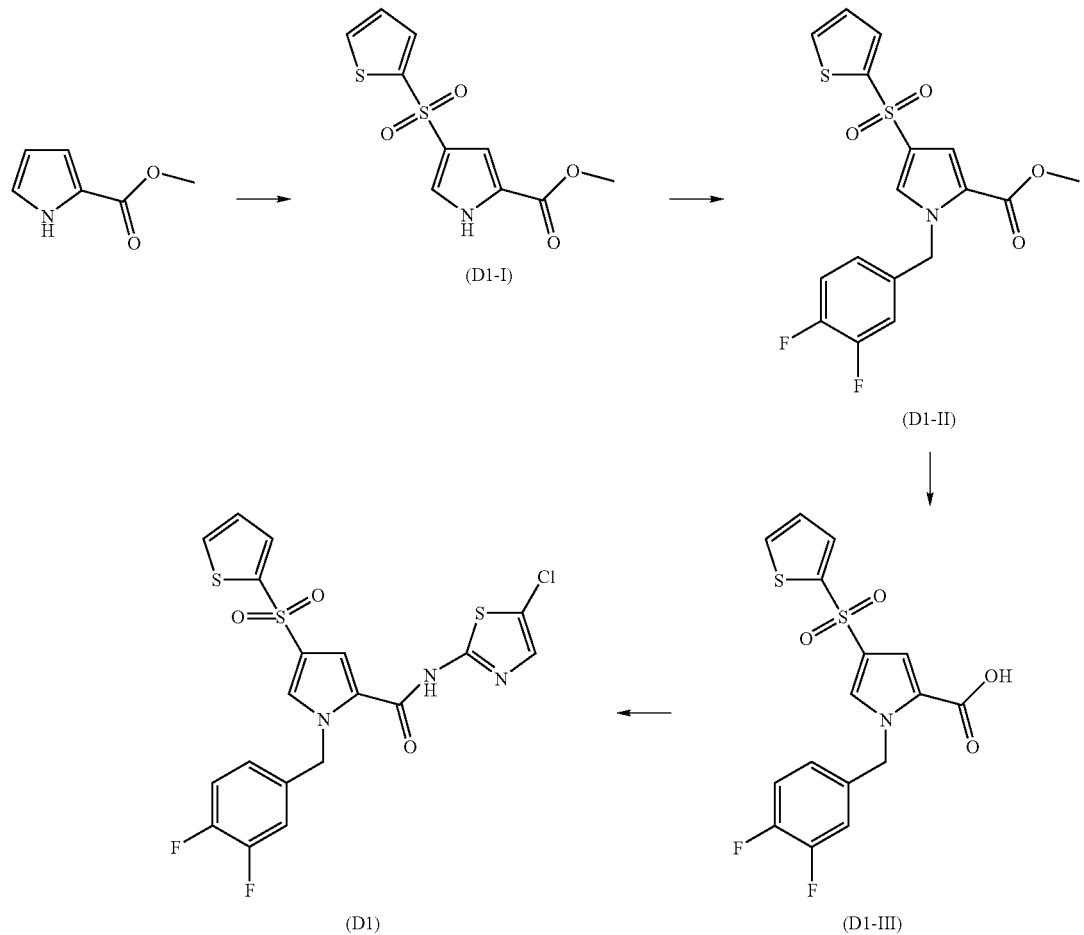

4-(Thiophene-2-sulfonyl)-1H-pyrrole-2-carboxylic acid methyl ester (D1-I)

To a solution of thiophene-2-sulfonyl chloride in dichloromethane was added aluminum chloride at 0-5° C., 1H-pyrrole-2-carboxylic acid methyl ester in dichloromethane was added slowly. Reaction mixture was stirred from room temperature to 60° C. for 24 hrs. On completion of reaction; reaction mixture was poured over crushed ice and extracted with dichloromethane, organic layer was washed with 1 N NaOH solution and brine, dried over anhydrous sodium sulfate, filtered and concentrated to afford 4-(thiophene-2-sulfonyl)-1H-pyrrole-2-carboxylic acid methyl ester (D1-I).

$^1$H NMR (400 MHz, CDCl$_3$): δ 3.85 (s, 3H), 7.06-7.08 (m, 1H), 7.18 (bs, 1H), 7.54-7.55 (m, 1H), 7.61-7.62 (m, 1H), 7.68-7.69 (m, 1H), 9.65 (bs, 1H).

MS (EI) m/z: 271.9 (M+1).

1-(3,4-Difluoro-benzyl)-4-(thiophene-2-sulfonyl)-1H-pyrrole-2-carboxylic acid methyl ester (D1-II)

To a solution of 4-(thiophene-2-sulfonyl)-1H-pyrrole-2-carboxylic acid methyl ester (D1-I) in dry dimethylformamide, cesium carbonate was added at 40-50° C. To this was added 3,4-difluro benzyl bromide and stirred overnight at 40-50° C. Reaction mixture was taken in to water and extracted with ethyl acetate, organic layer was washed with water and brine, dried over anhydrous sodium sulfate, filtered and concentrated to afford 1-(3,4-difluoro-benzyl)-4-(thiophene-2-sulfonyl)-1H-pyrrole-2-carboxylic acid methyl ester (D1-II).

MS (EI) m/z 397.9 (M+1).

1-(3,4-Difluoro-benzyl)-4-(thiophene-2-sulfonyl)-1H-pyrrole-2-carboxylic acid (D1-III)

To a solution of 1-(3,4-difluoro-benzyl)-4-(thiophene-2-sulfonyl)-1H-pyrrole-2-carboxylic acid methyl ester (D1-II) in ethanol was added potassium hydroxide in water and stirred overnight at room temperature. Solvent was removed under reduced pressure; the residue was taken in water and washed with diethyl ether. The aqueous layer was acidified with dilute HCl and precipitate was extracted with ethyl acetate. The organic layer was washed with water and brine, dried over anhydrous sodium sulphate, filtered and concentrated to afford 1-(3,4-difluoro-benzyl)-4-(thiophene-2-sulfonyl)-1H-pyrrole-2-carboxylic acid (D1-III).

$^1$H NMR (400 MHz, CDCl$_3$): δ 5.48 (s, 2H), 6.92 (bs, 1H), 7.06-7.37 (m, 3H), 7.72 (bs, 1H), 7.95-7.96 (m, 1H), 8.05 (bs, 1H), 13.0 (bs, 1H)

MS (EI) m/z: 383.9 (M+1). .

1-(3,4-Difluoro-benzyl)-4-(thiophene-2-sulfonyl)-1H-pyrrole-2-carboxylic acid (5-chloro-thiazol-2-yl)-amide (D1)

To a solution of 1-(3,4-difluoro-benzyl)-4-(thiophene-2-sulfonyl)-1H-pyrrole-2-carboxylic acid (D1-3) in dichloroethane was added catalytic amount of dimethylformamide and thionyl chloride at 0-5° C. Reaction mixture was heated at 80° C. for 6 hrs and concentrated in inert atmosphere, resulting residue was dissolved in dichloromethane and was added drop wise to mixture of pyridine (1 ml) and 5-chloro-thiazol-2-ylamine hydrochloride at 0° C. The reaction was maintained at 40-50° C. overnight. Water was added to reaction mixture and extracted with dichloromethane. The organic layer was washed with water and brine, dried over anhydrous sodium sulphate, filtered and concentrated to afford 1-(3,4-difluoro-benzyl)-4-(thiophene-2-sulfonyl)-1H-pyrrole-2-carboxylic acid (5-chloro-thiazol-2-yl)-amide (D1).

$^1$H NMR (400 MHz, CDCl$_3$): δ 5.53 (s, 2H), 6.85-7.07 (m, 3H), 7.44 (s, 1H), 7.54 (d, J=1.6 Hz, 1H), 7.58-7.61 (m, 2H), 7.76 (d, J=1.2 Hz, 1H), 12.2 (bs, 1H). MS (EI) m/z: 499.8 (M+1).

Examples D2 to D7 Were Prepared in Analogues Manner of Example (D1) from the Appropriate Intermediate

| Example No. | IUPAC name |
| --- | --- |
| D2 | 1-(3,4-Difluoro-benzyl)-4-(thiophene-2sulfonyl)-1H-pyrrole-2-carboxylic acid (5-chloro-thiazol-2-yl)-amide |
| D3 | 1-(3,4-Difluoro-benzyl)-4-(thiophene-2-sulfonyl)-1H-pyrrole-2-carboxylic acid (5-fluoro-thiazol-2-yl)-amide |
| D4 | 1-(4-Chloro-3-fluoro-benzyl)-4-(thiophene-2-sulfonyl)-1H-pyrrole-2-carboxylic acid (5-chloro-thiazol-2-yl)-amide |
| D5 | 1-(4-Chloro-3-fluoro-benzyl)-4-(thiophene-2-sulfonyl)-1H-pyrrole-2-carboxylic acid (5-fluoro-thiazol-2-yl)-amide |
| D6 | (5-Chloro-2-{[1-(3,4-difluoro-benzyl)-4-(thiophene-2-sulfonyl)-1H-pyrrole-2-carbonyl]-amino}-thiazol-4-yl)-acetic acid ethyl ester |
| D7 | (5-Chloro-2-{[1-(4-chloro-3-fluoro-benzyl)-4-(thiophene-2-sulfonyl)-1H-pyrrole-2-carbonyl-amino}-thiazol-4-yl)-acetic acid ethyl ester |

Example (E1)

(5-Chloro-2-{[1-(2,4-difluoro-benzyl)-4-isobutyl-1H-pyrrole-2-carbonyl]-amino}-thiazol-4-yl)-acetic acid

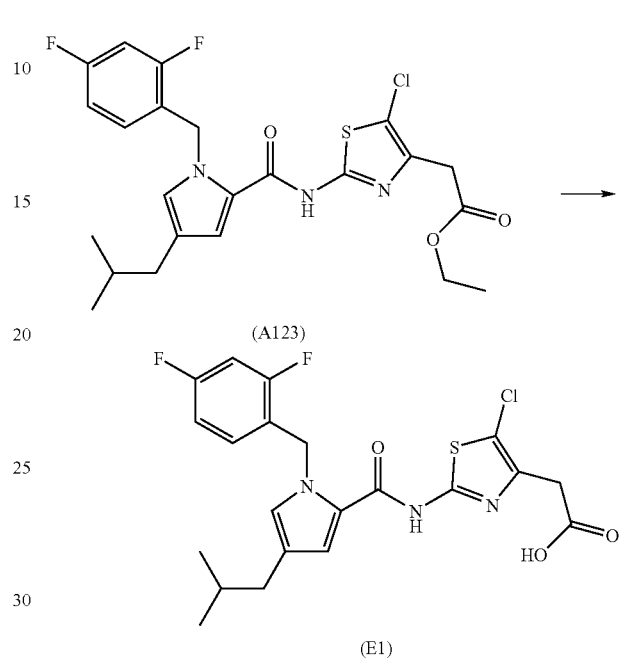

(A123)

(E1)

(5-Chloro-2-{[1-(2,4-difluoro-benzyl)-4-isobutyl-1H-pyrrole-2-carbonyl]-amino}-thiazol-4-yl)-acetic acid ethyl ester was taken in THF and methanol and to it lithium hydroxide monohydrate in water was added and stirred for 16-18 hrs. at room temperature. After completion of the reaction, the solvent was evaporated; the residue was diluted with water and was washed with diethyl ether. The aqueous layer was acidified with 1N HCl and extracted with ethyl acetate. The organic layer was washed with brine, dried over anhydrous sodium sulfate and evaporated the solvent to get the title compound (5-Chloro-2-{[1-(2,4-difluoro-benzyl)-4-isobutyl-1H-pyrrole-2-carbonyl]amino}-thiazol-4-yl)-acetic acid (E1).

$^1$H NMR (400 MHz, CDCl$_3$): δ 0.83 ((d, J=6.4 Hz, 6H), 1.66-1.70 (m, 1H), 2.23 (d, J=6.8 Hz, 2H), 3.62 (s, 2H), 5.55 (s, 2H), 6.66 (bs, 1H), 6.68-6.76 (m, 2H), 6.91-6.92 (m, 1H), 6.96-7.02 (m, 1H).

MS (EI) m/z: 467.9 (M+1).

Examples E2 to E48 Were Prepared in Analogues Manner of Example (E1) from the Appropriate Intermediate

| Example No. | IUPAC name |
| --- | --- |
| E2 | (5-Chloro-2-{[1-(4-fluoro-3-trifluoromethyl-benzyl)-4-isobutyl-1H-pyrrole-2-carbonyl]-amino}-thiazol-4-yl)-acetic acid |
| E3 | 6-{[1-(4-Fluoro-3-trifluoromethyl-benzyl)-4-isobutyl-1H-pyrrole-2-carbonyl]-amino}-nicotinic acid |

| Example No. | IUPAC name |
|---|---|
| E4 | (2-{[1-(2,4-Difluoro-benzyl)-4-isobutyl-1H-pyrrole-2-carbonyl]-amino}-thiazol-4-yl)-acetic acid |
| E5 | 6-{[1-(2,4-Difluoro-benzyl)-4-isobutyl-1H-pyrrole-2-carbonyl]-amino}-nicotinic acid |
| E6 | (2-{[1-(4-Fluoro-3-trifluoromethyl-benzyl)-4-isobutyl-1H-pyrrole-2-carbonyl]-amino}-thiazol-4-yl)-acetic acid |
| E7 | (2-{[4-Isobutyl-1-(2-thiophen-3-yl-ethyl)-1H-pyrrole-2-carbonyl]-amino}-thiazol-4-yl)-acetic acid |
| E8 | (2-{[4-Isobutyl-1-(2-thiophen-2-yl-ethyl)-1H-pyrrole-2-carbonyl]-amino}-thiazol-4-yl)-acetic acid |
| E9 | (5-Chloro-2-{[1-(3,4-dichloro-benzyl)-4-isobutyl-1H-pyrrole-2-carbonyl]-amino}-thiazol-4-yl)-acetic acid |
| E10 | (5-Chloro-2-{[1-(3,4-difluoro-benzyl)-4-isobutyl-1H-pyrrole-2-carbonyl]-amino}-thiazol-4-yl)-acetic acid |
| E11 | 3-(2-{[1-(3,4-Difluoro-benzyl)-4-isobutyl-1H-pyrrole-2-carbonyl]-amino}-thiazol-4-yl)-propionic acid |
| E12 | (5-Chloro-2-{[1-(3-chloro-4-fluoro-benzyl)-4-isobutyl-1H-pyrrole-2-carbonyl]-amino}-thiazol-4-yl)-acetic acid |
| E13 | (5-Chloro-2-{[1-(4-chloro-3-fluoro-benzyl)-4-isobutyl-1H-pyrrole-2-carbonyl]-amino}-thiazol-4-yl)-acetic acid |
| E14 | (5-Chloro-2-{[1-(3,4-difluoro-benzyl)-4-(1-hydroxy-2-methyl-propyl)-1H-pyrrole-2-carbonyl]-amino}-thiazol-4-yl)-acetic acid |
| E15 | 6-{[1-(3,4-Difluoro-benzyl)-4-isobutyl-1H-pyrrole-2-carbonyl]-amino}-nicotinic acid |
| E16 | (5-Chloro-2-{[4-isobutyl-1-(4-methanesulfonyl-benzyl)-1H-pyrrole-2-carbonyl]-amino}-thiazol-4-yl)-acetic acid |
| E17 | (5-Chloro-2-{[1-(3,4-difluoro-benzyl)-4-(thiophene-2-sulfonyl)-1H-pyrrole-2-carbonyl]-amino}-thiazol-4-yl)-acetic acid |
| E18 | (5-Chloro-2-{[1-(4-chloro-3-fluoro-benzyl)-4-(thiophene-2-sulfonyl)-1H-pyrrole-2-carbonyl]-amino}-thiazol-4-yl)-acetic acid |
| E19 | (2-{[4-Isobutyl-1-(4-methanesulfonyl-benzyl)-1H-pyrrole-2-carbonyl]-amino}-thiazol-4-yl)-acetic acid |
| E20 | (5-Chloro-2-{[4-(1-hydroxy-2-methyl-propyl)-1-(4-methanesulfonyl-benzyl)-1H-pyrrole-2-carbonyl]-amino}-thiazol-4-yl)-acetic acid |
| E21 | (5-Chloro-2-{[1-(4-cyclopropanesulfonyl-benzyl)-4-isobutyl-1H-pyrrole-2-carbonyl]-amino}-thiazol-4-yl)-acetic acid |
| E22 | (5-Chloro-2-{[1-(4-cyclopropanesulfonyl-benzyl)-4-(1-hydroxy-2-methyl-propyl)-1H-pyrrole-2-carbonyl]-amino}-thiazol-4-yl)-acetic acid |
| E23 | (5-Chloro-2-{[1-(3,4-difluoro-benzyl)-4-(4-methanesulfonyl-benzyl)-1H-pyrrole-2-carbonyl]-amino}-thiazol-4-yl)-acetic acid |
| E24 | (5-Chloro-2-{[1-(4-fluoro-3-trifluoromethyl-benzyl)-4-isobutyryl-1H-pyrrole-2-carbonyl]-amino}-thiazol-4-yl)-acetic acid |
| E25 | (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid |
| E26 | (5-Chloro-2-{[1-(3,4-difluoro-benzyl)-4-isobutyryl-1H-pyrrole-2-carbonyl]-amino}-thiazol-4-yl)-acetic acid |
| E27 | (5-Chloro-2-{[1-(4-chloro-3-fluoro-benzyl)-4-(1-hydroxy-2-methyl-propyl)-1H-pyrrole-2-carbonyl]-amino}-thiazol-4-yl)-acetic acid |
| E28 | (2-{[1-(4-Chloro-3-fluoro-benzyl)-4-(1-hydroxy-2-methyl-propyl)-1H-pyrrole-2-carbonyl]-amino}-thiazol-4-yl)-acetic acid |
| E29 | (5-Chloro-2-{[1-(3-fluoro-4-trifluoromethyl-benzyl)-4-(1-hydroxy-2-methyl-propyl)-1H-pyrrole-2-carbonyl]-amino}-thiazol-4-yl)-acetic acid |
| E30 | (2-{[1-(3-Fluoro-4-trifluoromethyl-benzyl)-4-(1-hydroxy-2-methyl-propyl)-1H-pyrrole-2-carbonyl]-amino}-thiazol-4-yl)-acetic acid |
| E31 | (5-Chloro-2-{[1-(4-chloro-3-trifluoromethyl-benzyl)-4-(1-hydroxy-2-methyl-propyl)-1H-pyrrole-2-carbonyl]-amino}-thiazol-4-yl)-acetic acid |
| E32 | (2-{[1-(4-Chloro-3-trifluoromethyl-benzyl)-4-(1-hydroxy-2-methyl-propyl)-1H-pyrrole-2-carbonyl]-amino}-thiazol-4-yl)-acetic acid |
| E33 | (5-Chloro-2-{[1-(3-fluoro-benzyl)-4-(1-hydroxy-2-methyl-propyl)-1H-pyrrole-2-carbonyl]-amino}-thiazol-4-yl)-acetic acid |
| E34 | (2-{[1-(3-Fluoro-benzyl)-4-(1-hydroxy-2-methyl-propyl)-1H-pyrrole-2-carbonyl]-amino}-thiazol-4-yl)-acetic acid |
| E35 | (5-Chloro-2-{[1-(2,4-difluoro-benzyl)-4-(1-hydroxy-2-methyl-propyl)-1H-pyrrole-2-carbonyl]-amino}-thiazol-4-yl)-acetic acid |
| E36 | (2-{[1-(2,4-Difluoro-benzyl)-4-(1-hydroxy-2-methyl-propyl)-1H-pyrrole-2-carbonyl]-amino}-thiazol-4-yl)-acetic acid |
| E37 | (5-Chloro-2-{[1-(2,4-dichloro-benzyl)-4-(1-hydroxy-2-methyl-propyl)-1H-pyrrole-2-carbonyl]-amino}-thiazol-4-yl)-acetic acid |
| E38 | (2-{[1-(2,4-Dichloro-benzyl)-4-(1-hydroxy-2-methyl-propyl)-1H-pyrrole-2-carbonyl]-amino}-thiazol-4-yl)-acetic acid |
| E39 | (5-Chloro-2-{[4-(1-hydroxy-2-methyl-propyl)-1-(4-trifluoromethyl-benzyl)-1H-pyrrole-2-carbonyl]-amino}-thiazol-4-yl)-acetic acid |
| E40 | (2-{[4-(1-Hydroxy-2-methyl-propyl)-1-(4-trifluoromethyl-benzyl)-1H-pyrrole-2-carbonyl]-amino}-thiazol-4-yl)-acetic acid |
| E41 | (5-Chloro-2-{[4-(1-hydroxy-2-methyl-propyl)-1-(3-trifluoromethyl-benzyl)-1H-pyrrole-2-carbonyl]-amino}-thiazol-4-yl)-acetic acid |
| E42 | (2-{[4-(1-Hydroxy-2-methyl-propyl)-1-(3-trifluoromethyl-benzyl)-1H-pyrrole-2-carbonyl]-amino}-thiazol-4-yl)-acetic acid |
| E43 | (5-Chloro-2-{[1-(4-chloro-benzyl)-4-(1-hydroxy-2-methyl-propyl)-1H-pyrrole-2-carbonyl]-amino}-thiazol-4-yl)-acetic acid |
| E44 | (2-{[1-(4-Chloro-benzyl)-4-(1-hydroxy-2-methyl-propyl)-1H-pyrrole-2-carbonyl]-amino}-thiazol-4-yl)-acetic acid |
| E45 | (5-Chloro-2-{[1-(3,4-dichloro-benzyl)-4-(1-hydroxy-2-methyl-propyl)-1H-pyrrole-2-carbonyl]-amino}-thiazol-4-yl)-acetic acid |
| E46 | (2-{[1-(3,4-Dichloro-benzyl)-4-(1-hydroxy-2-methyl-propyl)-1H-pyrrole-2-carbonyl]-amino}-thiazol-4-yl)-acetic acid |
| E47 | (5-Chloro-2-{[1-(4-fluoro-benzyl)-4-(1-hydroxy-2-methyl-propyl)-1H-pyrrole-2-carbonyl]-amino}-thiazol-4-yl)-acetic acid |
| E48 | (2-{[1-(4-Fluoro-benzyl)-4-(1-hydroxy-2-methyl-propyl)-1H-pyrrole-2-carbonyl]-amino}-thiazol-4-yl)-acetic acid |

Chiral separation: Compounds with chiral centre were separated using chiral HPLC. The conditions used and the compounds separated are given below:

| Example | IUPAC | Separation Conditions |
|---|---|---|
| F1 | (+) (5-Chloro-2-{[1-(3,4-difluoro-benzyl)-4-(1-hydroxy-2-methyl-propyl)-1H-pyrrole-2-carbonyl]-amino}-thiazol-4-yl)-acetic acid | Column: Daicel Chiralcel OJRH 21 × 250 mm with guard |
| | (−) (5-Chloro-2-{[1-(3,4-difluoro-benzyl)-4-(1-hydroxy-2-methyl-propyl)-1H-pyrrole-2-carbonyl]-amino}-thiazol-4-yl)-acetic acid | Solvent 90:10 Methanol, 0.1% Formic Acid in water |
| F2 | (+) 1-(3,4-Difluoro-benzyl)-4-(1-hydroxy-2-methyl-propyl)-1H-pyrrole-2-carboxylic acid thiazol-2-ylamide | Column: Daicel Chiralcel OJRH 21 × 250 mm with guard (5u) |
| | (−) 1-(3,4-Difluoro-benzyl)-4-(1-hydroxy-2-methyl-propyl)-1H-pyrrole-2-carboxylic acid thiazol-2-ylamide | Solvent: 40:60 Water, Acetonitrile |
| F3 | (+) 1-(3,4-Difluoro-benzyl)-4-(1-hydroxy-2-methyl-propyl)-1H-pyrrole-2-carboxylic acid (5-chloro-thiazol-2-yl)-amide | Column: Daicel Chiralcel OJRH 21 × 250 mm with guard (5u) |
| | (−) 1-(3,4-Difluoro-benzyl)-4-(1-hydroxy-2-methyl-propyl)-1H-pyrrole-2-carboxylic acid (5-chloro-thiazol-2-yl)-amide | Solvent: 40:60 Water, Acetonitrile |

Measurement of Glucokinase Activity:

Glucokinase (GK) activity, in vitro, has been measured using a coupled enzymatic assay (Ref: Hariharan et al (1997) Diabetes 46: 11-16). GK catalyzes the first step, the conversion of glucose to glucose-6-phosphate (G6P) in the presence of ATP. G6P in turn is converted by glucose-6-phosphate dehydrogenase (G6PD) to 6-phosphogluconate, a process that requires NAD, resulting in NADH formation. Since the GK-catalyzed step is the rate-limiting step of this coupled enzymatic process, the rate of accumulation of 6-phosphogluconate and NADH is directly proportional to the rate of glucose phosphorylation by GK. The rate of the GK-catalyzed reaction can therefore be measured by monitoring the increase in NADH absorbance at 340 nm.

The assay is carried out according to the protocol outlined in Hariharan et al (1997), Diabetes 46: 11-16. Briefly, the test compounds are incubated in a reaction mix containing 25 mM HEPES (pH 7.2), 10 mM MgCl$_2$, 100 mM KCl, 5 mM ATP, 2 mM DTT, 0.5 mM NAD, 1 U/ml *Leuconostoc mesenteroides* G6PD, 0.3 U/ml of purified human recombinant GK, and different concentrations of glucose. Enzymatic activity is calculated from the initial reaction velocity, measured from the change in NADH absorbance as a function of time.

Compounds described in formula (I), in concentration ranges from 1.0 nM to 500 µM, are tested in the purified human recombinant glucokinase assay described above.

A compound is considered to be a glucokinase activator if it, in its testable range of concentrations, yields a higher rate of glucose phosphorylation than in its absence at a particular glucose concentration, for example at 5 mM glucose.

The glucokinase activation data of some representative compounds of the present disclosure, which are illustrative but not to be construed as limiting the scope or spirit of the disclosure, are given in the table 1 below.

TABLE I

Glucokinase activation data (EC$_{50}$ values for GK activation at 5 mM glucose):

| Example | EC$_{50}$ (µM) |
|---------|----------------|
| C6      | 0.6            |
| C8      | 0.43           |
| C2      | 0.63           |
| E23     | 0.3            |

Characterization of Partial Glucokinase Activators from the In Vitro Glucokinase Assay:

Compounds of interest from the general formula (I) are tested in the in vitro GK enzymatic assay to monitor dose-dependent effect on glucokinase activation (in kinetic mode), as described above, at various glucose concentrations. The maximum efficacy (E$_{max}$) and potency (EC$_{50}$) for the assessment of partial glucokinase activation have been defined in our co-pending application 409/CHE/2007. The same definitions have also been used here. The S$_{0.5}$ of glucokinase for glucose at different concentration of each compound of interest is calculated from the following modified version of the Michaelis-Menten equation, $V=V_{max}[S]^n/(S_{0.5}{}^n+[S]^n)$, where [S] is the glucose concentration and n is the Hill coefficient (taken as 1.7 to account for the sigmoidal kinetics of glucokinase with respect to glucose). The S$_{0.5}$ is plotted against the log of the compound concentration. The change in the S$_{0.5}$ of glucokinase (ΔS$_{0.5}$) for glucose is calculated by subtracting the S$_{0.5}$ at each concentration of the compound from the S$_{0.5}$ in the vehicle control. The ΔS$_{0.5}$ is then normalized to a percent scale, where the S$_{0.5}$ in the vehicle control is set to 0% and 0 mM glucose is set to 100%. The % ΔS$_{0.5}$ is then plotted against the log of the compound concentration. The EC$_{50}$ of % change in S$_{0.5}$ is obtained from the sigmoidal fit of the data.

Typical graphs of % ΔS$_{0.5}$ plotted against the log of the concentration of one partial and one full glucokinase activator from the general formula (I) are shown in FIG. 1. In the case of the full activator (filled circle), the ΔS$_{0.5}$ changes by 95% at saturating concentrations of the compound. This means that at saturating concentrations of the full activator, GK requires only 5% of the glucose required in the absence of the compound for half-maximal enzyme activity. In the case of the partial activator (open circle example), the ΔS$_{0.5}$ changes by 65% at saturating concentrations of the compound. In other words, at saturating concentrations of the partial activator, the glucose requirement of GK for half-maximal enzyme activity goes down to 35% of the requirement in the absence of the compound. In both cases, the potencies of S$_{0.5}$ reduction, as calculated from the sigmoidal fit of the ΔS$_{0.5}$ curves, are the same (0.2 µM).

Characterization data of some representative partial glucokinase activators of the present disclosure, which are illustrative but not limiting, are given in table 2.

TABLE II

E$_{max}$ and EC$_{50}$ of partial GK activators (with respect to % ΔS$_{0.5}$)

| Example | EC$_{50}$ (µM) | % E$_{max}$ |
|---------|----------------|-------------|
| A116    | 0.3            | 70          |
| A40     | 0.2            | 65          |
| A31     | 0.22           | 40          |

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A compound of formula (I)

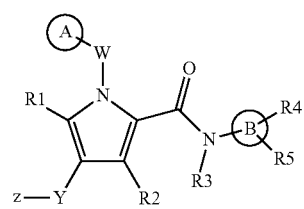

(I)

or its stereoisomer, or a pharmaceutically acceptable salt thereof, wherein,

Ring A is a mono or a bicyclic ring independently selected from cycloalkyl, aryl, heteroaryl and partially/fully saturated rings thereof;

Ring A is optionally substituted with up to 4 substituents independently selected from alkyl, alkenyl, alkynyl, halogen, mono, di or perhaloalkyl, nitrile, nitro, oxo, —NR$^6$R$^7$, —OR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —(CR$^8$R$^9$)$_p$C(O)OR$^6$, —(CR$^8$R$^9$)$_n$C(O)NR$^6$R$^7$—(CR$^8$R$^9$)$_n$C(O)R$^6$, cycloalkyl, cycloalkylalkyl, heterocyclyl, heterocycloalkyl, aryl, arylalkyl, heteroaryl, heteroarylalkyl, tetrazole, tetrazolylalkyl groups; further, the cycloalkyl, heterocycloalkyl, aryl, heteroaryl groups are optionally substituted with halo, straight chain or branched chain alkyl, alkenyl, alkynyl, cycloalkyl, aryl, heteroaryl, heterocycle, alkylsulphonyl, nitro, cyano, —COOR$^6$, —C(O)NR$^6$R$^7$, —OR$^6$, —SR$^6$ or —NR$^6$R$^7$;

p=0-2; n=0-4;

R$^6$ and R$^7$ are independently selected from a group consisting of hydrogen, alkyl, alkenyl, alkynyl, aryl, arylalkyl, heteroaryl, heteroarylalkyl, cycloalkyl, cycloalkylalkyl, heterocyclyl and heterocyclylalkyl, wherein each of alkyl, alkenyl, alkynyl, aryl, arylalkyl, heteroaryl, heteroarylalkyl, cycloalkyl, cycloalkylalkyl, heterocyclyl and heterocylylalkyl is optionally substituted with halo, straight chain or branched chain alkyl, alkenyl, alkynyl, cycloalkyl, aryl, heteroaryl, heterocycle, alkylsulphonyl, nitro, cyano, —COOR$^6$, —C(O)NR$^6$R$^7$—OR$^6$, —SR$^6$ or —NR$^6$R$^7$;

R$^8$ and R$^9$ are independently selected from a group consisting of hydrogen, fluorine, chlorine, OR$^6$, straight and branched chain alkyl groups, aryl, arylalkyl, perfluoroalkyl, halo, straight chain or branched chain alkyl, alkenyl, alkynyl, cycloalkyl, aryl, heteroaryl, heterocycle, alkylsulphonyl, nitro, cyano, —COOR$^6$, —C(O)NR$^6$R$^7$, —OR$^6$, —SR$^6$ and —NR$^6$R$^7$; wherein the aryl group is optionally substituted with halo, straight chain or branched chain alkyl, alkenyl, alkynyl, cycloalkyl, aryl, heteroaryl, heterocycle, alkylsulphonyl, nitro, cyano, —COOR$^6$, —C(O)NR$^6$R$^7$, —OR$^6$, —SR$^6$ or —NR$^6$R$^7$, W and Y independently represents:

—(X)$_m$(CR$^8$R$^9$)$_n$(X)$_o$—, wherein X is selected from C(O), O, S(O)$_p$ and NR$^6$, R$^6$, R$^8$, R$^9$ are as described herein above, m and o are independently either 0 or 1, n is selected from numbers 0-4, p is selected from numbers 0-2;

Z is other than hydrogen, and is selected from a group consisting of halogen, straight or branched chain alkyl, alkenyl, alkynyl, aryl, aralkyl, heteroaryl, heteroarylalkyl, heterocyclyl, heterocyclylalkyl, cycloalkyl, and cycloalkylalkyl, wherein each of alkyl, alkenyl, alkynyl, aryl, aralkyl, heteroaryl, heteroarylalkyl, heterocyclyl, heterocyclylalkyl, cycloalkyl, cycloalkylalkyl is optionally substituted with up to 4 substituents independently selected from halogen, nitrile, nitro, oxo, —NR$^6$R$^7$, —OR$^6$, —S(O)$_p$ R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —(CR$^8$R$^9$)$_n$C(O)OR$^6$, —(CR$^8$R$^9$)$_n$C(O)NR$^6$R$^7$, —(CR$^8$R$^9$)$_n$S(O)$_p$ NR$^6$R$^7$, —(CR$^8$R$^9$)$_n$NC(O)R$^6$, —(CR$^8$R$^9$)$_n$OR$^6$, —(CR$^8$R$^9$)$_n$NR$^6$R$^7$, —(CR$^8$R$^9$)$_n$C(O)R$^6$, tetrazole, and tetrazolylalkyl;

wherein, p=0-2; n=0-4;

R$^6$, R$^7$, R$^8$ and R$^9$ are as described herein above;

R$^1$, R$^2$ are independently selected from hydrogen, perfluoroalkyl, cycloalkyl, aryl, heterocyclyl, heteroaryl, cycloalkylalkyl, arylalkyl, heterocyclylalkyl, heteroarylalkyl, —OH, —OR$^6$, —(CH$_2$)$_n$OR$^6$, tetrazole and tetrazolylalkyl, wherein each of cycloalkyl, aryl, heterocyclyl, heteroaryl, cycloalkylalkyl, arylalkyl, heterocyclylalkyl, heteroarylalkyl, —OH, —OR$^6$, —(CH$_2$)$_n$OH, —(CH$_2$)$_n$OR$^6$, tetrazole and tetrazolylalkyl is further substituted with halo, straight chain or branched chain alkyl, alkenyl, alkynyl, cycloalkyl, aryl, heteroaryl, heterocycle, alkylsulphonyl, nitro, cyano, —COOR$^6$, —C(O)NR$^6$R$^7$, —SR$^6$ or —NR$^6$R$^7$;

wherein, n=0-4;

R$^6$ is as described herein above;

R$^3$ is selected from a group consisting of hydrogen, alkyl and perfluoroalkyl;

Ring B is an optionally substituted moiety selected from the group consisting of:

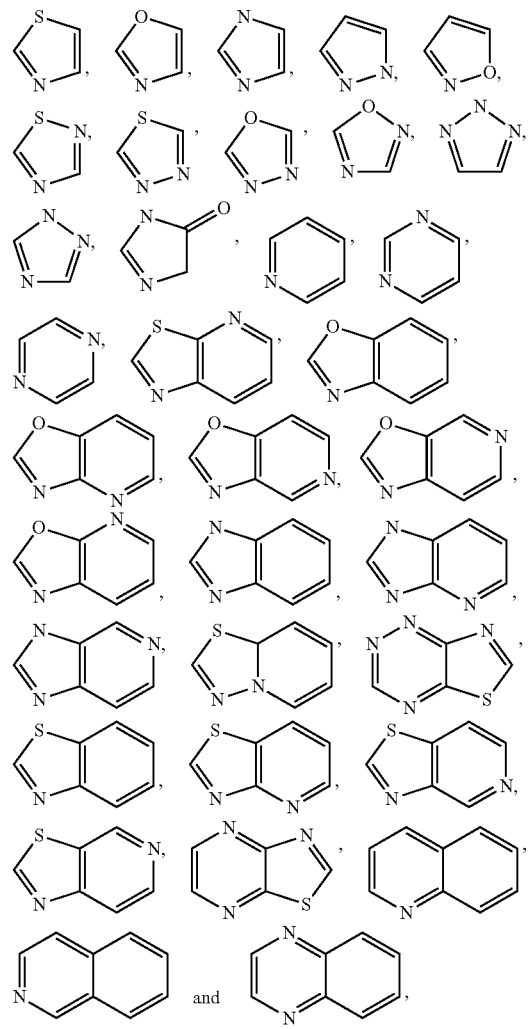

with the proviso that the amide nitrogen of formula (I) is not connected through any heteroatom of ring-B;

R$^4$ and R$^5$ are independently selected from a group consisting of hydrogen, halogen, alkyl, alkenyl, alkynyl, cycloalkyl, cycloalkylalkyl, heterocyclyl, heterocycloalkyl, aryl, arylalkyl, heteroaryl, heteroarylalkyl, tetrazole, tetrazolylalkyl, mono, di or tri substituted haloalkyl, nitrile, nitro, oxo, —NR$^6$, —NR$^6$R$^7$, —OR$^6$, —S(O)$_p$R$^6$, —S(O)$_p$NR$^6$R$^7$, —NR$^6$S(O)$_p$R$^7$, —NR$^6$C(O)R$^7$, —OS(O)$_p$R$^7$, —NR$^6$C(O)OR$^7$, —(CR$^8$R$^9$)$_n$C(O)OR$^6$, —(CR$^8$R$^9$)$_n$(CO)NR$^6$R$^7$, —(CR$^8$R$^9$)$_n$S(O)$_p$NR$^6$R$^7$, —(CR$^8$R$^9$)$_n$(R$^6$)C(O)R$^6$, —(CR$^8$R$^9$)$_n$OR$^6$, C(R$^8$R$^9$)$_n$NR$^6$R$^7$ and C(R$^8$R$^9$)$_n$CO(R$^6$), wherein each of R$^4$ and R$^5$ is optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR$^6$, —C(O)NR$^6$R$^7$, —OR$^6$, —SR$^6$ or —NR$^6$R$^7$;

wherein n=0-4;

R$^6$, R$^7$, R$^8$ and R$^9$ are as described herein above;

in addition to R$^4$ and R$^5$, ring-B can be further optionally substituted with one or more substituents selected from halo, straight chain or branched chain alkyl, alkenyl, alkynyl, cycloalkyl, aryl, heteroaryl, heterocycle, alkylsulphonyl, oxo, nitro, cyano, —COOR⁶, —C(O)NR⁶R⁷, —OR⁶, —SR⁶ or —NR⁶R⁷.

2. The compound as claimed in claim 1, or its stereoisomer, or a pharmaceutically acceptable salt thereof, wherein ring-A is selected from

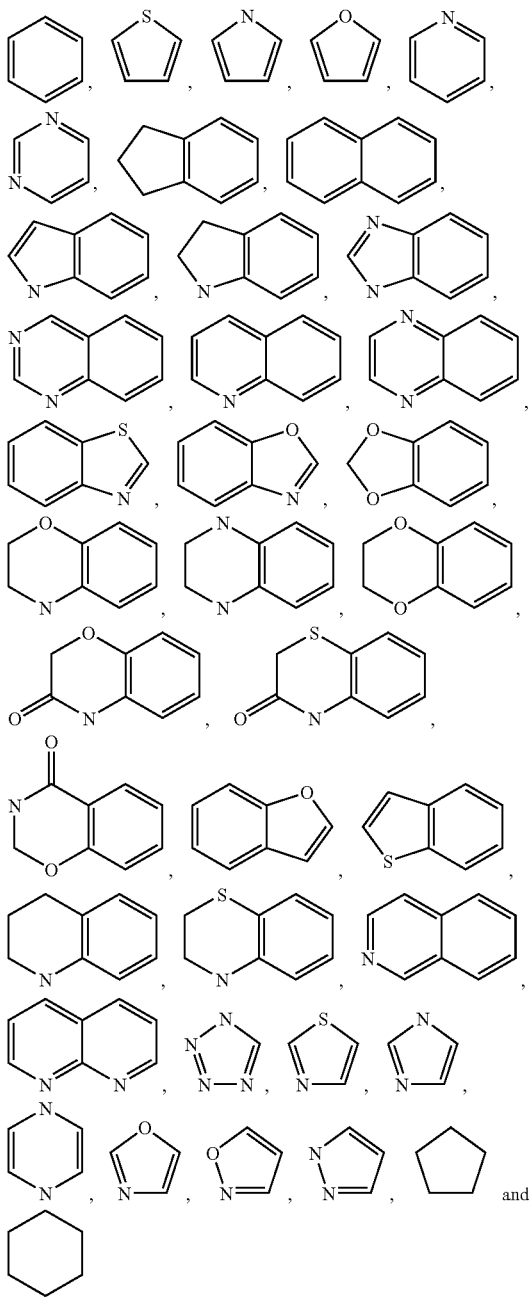

3. The compound as claimed in claim 1, or its stereoisomer, or a pharmaceutically acceptable salt thereof, wherein Ring-A is selected from

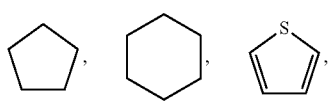

and

Z is selected from halogen, alkyl, cycloalkyl, heterocyclyl, aryl or heteroaryl.

4. A compound as claimed in claim 1 which is
4-Cyclopentylmethyl-1-(2,4-difluoro-benzyl)-1H-pyrrole-2-carboxylic acid (5-chloro-thiazol-2-yl)-amide;
4-Isobutyl-1-(4-trifluoromethyl-benzyl)-1H-pyrrole-2-carboxylic acid thiazol-2-ylamide;
4-Isobutyl-1-(3-trifluoromethyl-benzyl)-1H-pyrrole-2-carboxylic acid thiazol-2-ylamide;
4-Isobutyl-1-(3-nitro-benzyl)-1H-pyrrole-2-carboxylic acid thiazol-2-ylamide;
4-(3-Methyl-butyl)-1-(4-trifluoromethyl-benzyl)-1H-pyrrole-2-carboxylic acid thiazol-2-ylamide;
4-(3-Methyl-butyl)-1-(3-nitro-benzyl)-1H-pyrrole-2-carboxylic acid thiazol-2-ylamide;
4-Isobutyl-1-(4-trifluoromethyl-benzyl)-1H-pyrrole-2-carboxylic acid (5-chloro-thiazol-2-yl)-amide;
4-Isobutyl-1-(3-trifluoromethyl-benzyl)-1H-pyrrole-2-carboxylic acid (5-chloro-thiazol-2-yl)-amide;
4-Isobutyl-1-(3-nitro-benzyl)-1H-pyrrole-2-carboxylic acid (5-chloro-thiazol-2-yl)-amide;
4-(3-Methyl-butyl)-1-(4-trifluoromethylbenzyl)-1H-pyrrole-2-carboxylic acid (5-chloro-thiazol-2-yl)-amide;
4-(3-Methyl-butyl)-1-(3-nitro-benzyl)-1H-pyrrole-2-carboxylic acid (5-chloro-thiazol-2-yl)-amide;
4-(4-Chloro-benzyl)-1-(4-trifluoromethyl-benzyl)-1H-pyrrole-2-carboxylic acid thiazol-2-ylamide;
4-(4-Chloro-benzyl)-1-(4-trifluoromethyl-benzyl)-1H-pyrrole-2-carboxylic acid (5-chloro-thiazol-2-yl)-amide;
4-(4-Chloro-benzyl)-1-(3-trifluoromethyl-benzyl)-1H-pyrrole-2-carboxylic acid thiazol-2-ylamide;
4-(4-Chloro-benzyl)-1-(3-trifluoromethyl-benzyl)-1H-pyrrole-2-carboxylic acid (5-chloro-thiazol-2-yl)-amide;
4-(4-Chloro-benzyl)-1-(3-nitro-benzyl)-1H-pyrrole-2-carboxylic acid thiazol-2-ylamide;
4-(4-Chlorobenzyl)-1-(3-nitro-benzyl)-1H-pyrrole-2-carboxylic acid (5-chloro-thiazol-2-yl)-amide;
4-Isobutyl-1-(4-nitro-benzyl)-1H-pyrrole-2-carboxylic acid thiazol-2-ylamide;
4-(3-Methyl-butyl)-1-(3-trifluoromethylbenzyl)-1H-pyrrole-2-carboxylic acid (5-chloro-thiazol-2-yl)-amide;
1-(2,4-Difluoro-benzyl)-4-isobutyl-1H-pyrrole-2-carboxylic acid (5-chloro-thiazol-2-yl)-amide;
4-(4-Chloro-benzyl)-1-cyclopentylmethyl-1H-pyrrole-2-carboxylic acid thiazol-2-ylamide;
4-(4-Chloro-benzyl)-1-cyclopentylmethyl-1H-pyrrole-2-carboxylic acid (5-chloro-thiazol-2-yl)-amide;
4-(4-Chloro-benzyl)-1-(2-thiophen-3-yl-ethyl)-1H-pyrrole-2-carboxylic acid thiazol-2-ylamide;
4-(4-Chloro-benzyl)-1-(2,4-difluoro-benzyl)-1H-pyrrole-2-carboxylic acid thiazol-2-ylamide;
1-(2,4-Difluoro-benzyl)-4-(3-methyl-butyl)-1H-pyrrole-2-carboxylic acid (5-chloro-thiazol-2-yl)-amide;

4-Isobutyl-1-(3-trifluoromethyl-benzyl)-1H-pyrrole-2-carboxylic acid benzothiazol-2-ylamide;
4-Isobutyl-1-(3-trifluoromethyl-benzyl)-1H-pyrrole-2-carboxylic acid (6-fluorobenzothiazol-2-yl)-amide;
4-Isobutyl-1-(3-trifluoromethyl-benzyl)-1H-pyrrole-2-carboxylic acid (4-phenyl-thiazol-2-yl)-amide;
1-(4-Fluoro-3-trifluoromethyl-benzyl)-4-isobutyl-1H-pyrrole-2-carboxylic acid (6-fluoro-benzothiazol-2-yl)-amide;
1-(4-Fluoro-3-trifluoromethyl-benzyl)-4-isobutyl-1H-pyrrole-2-carboxylic acid benzothiazol-2-ylamide;
1-(4-Fluoro-3-trifluoromethyl-benzyl)-4-isobutyl-1H-pyrrole-2-carboxylic acid (5-chloro-thiazol-2-yl)-amide;
1-(2-Fluoro-3-trifluoromethyl-benzyl)-4-isobutyl-1H-pyrrole-2-carboxylic acid benzothiazol-2-ylamide;
4-Isobutyl-1-(2-thiophen-3-yl-ethyl)-1H-pyrrole-2-carboxylic acid benzothiazol-2-ylamide;
4-Isobutyl-1-(2-thiophen-3-yl-ethyl)-1H-pyrrole-2-carboxylic acid thiazol-2-ylamide;
1-(4-Fluoro-3-trifluoromethyl-benzyl)-4-isobutyl-1H-pyrrole-2-carboxylic acid thiazol-2-ylamide;
1-(2,4-Difluoro-benzyl)-4-isobutyl-1H-pyrrole-2-carboxylic acid thiazol-2-ylamide;
4-Isobutyl-1-(2-thiophen-2-yl-ethyl)-1H-pyrrole-2-carboxylic acid thiazol-2-ylamide;
1-(2,4-Difluoro-benzyl)-4-isobutyl-1H-pyrrole-2-carboxylic acid (5-fluoro-thiazol-2-yl)-amide;
1-(3,4-Difluoro-benzyl)-4-isobutyl-1H-pyrrole-2-carboxylic acid thiazol-2-ylamide;
1-(3,4-Difluoro-benzyl)-4-isobutyl-1H-pyrrole-2-carboxylic acid (5-chloro-thiazol-2-yl)-amide;
1-(3,4-Dichloro-benzyl)-4-isobutyl-1H-pyrrole-2-carboxylic acid thiazol-2-ylamide;
1-(3,4-Dichloro-benzyl)-4-isobutyl-1H-pyrrole-2-carboxylic acid (5-chloro-thiazol-2-yl)-amide;
1-(3,4-Difluoro-benzyl)-4-isobutyl-1H-pyrrole-2-carboxylic acid (5-fluoro-thiazol-2-yl)-amide;
4-Isobutyl-1-(2-thiophen-3-yl-ethyl)-1H-pyrrole-2-carboxylic acid (5-chloro-thiazol-2-yl)-amide;
4-Cyclopentylmethyl-1-(2,4-difluoro-benzyl)-1H-pyrrole-2-carboxylic acid thiazol-2-ylamide;
4-Cyclopentylmethyl-1-(2,4-difluoro-benzyl)-1H-pyrrole-2-carboxylic acid (5-fluoro-thiazol-2-yl)-amide;
4-Cyclopentylmethyl-1-(3,5-difluoro-benzyl)-1H-pyrrole-2-carboxylic acid thiazol-2-ylamide;
4-Cyclopentylmethyl-1-(3,5-difluoro-benzyl)-1H-pyrrole-2-carboxylic acid (5-chloro-thiazol-2-yl)-amide;
4-Cyclopentylmethyl-1-(3,5-difluoro-benzyl)-1H-pyrrole-2-carboxylic acid (5-fluoro-thiazol-2-yl)-amide;
1-(2,4-Difluoro-benzyl)-4-ethyl-1H-pyrrole-2-carboxylic acid thiazol-2-ylamide;
1-(2,4-Difluoro-benzyl)-4-ethyl-1H-pyrrole-2-carboxylic acid (5-chloro-thiazol-2-yl)-amide;
1-(2,4-Difluoro-benzyl)-4-ethyl-1H-pyrrole-2-carboxylic acid (5-fluoro-thiazol-2-yl)-amide;
1-(4-Fluoro-benzyl)-4-isobutyl-1H-pyrrole-2-carboxylic acid (5-chloro-thiazol-2-yl)-amide;
1-(3,5-Difluoro-benzyl)-4-ethyl-1H-pyrrole-2-carboxylic acid thiazol-2-ylamide;
1-(3,5-Difluoro-benzyl)-4-ethyl-1H-pyrrole-2-carboxylic acid (5-chloro-thiazol-2-yl)-amide;
1-(2,4-Difluoro-benzyl)-4-isobutyl-1H-pyrrole-2-carboxylic acid (4-methyl-thiazol-2-yl)-amide;
1-(2,4-Difluoro-benzyl)-4-isobutyl-1H-pyrrole-2-carboxylic acid (5-methyl-thiazol-2-yl)-amide;
1-(4-Fluoro-3-trifluoromethyl-benzyl)-4-isobutyl-1H-pyrrole-2-carboxylic acid (5-fluoro-thiazol-2-yl)-amide;
1-[2-(3,4-Difluoro-phenoxy)-ethyl]-4-isobutyl-1H-pyrrole-2-carboxylic acid thiazol-2-ylamide;
1-[2-(3,4-Difluoro-phenoxy)-ethyl]-4-isobutyl-1H-pyrrole-2-carboxylic acid (5-chloro-thiazol-2-yl)-amide;
1-[1-(4-Fluoro-phenyl)-ethyl]-4-isobutyl-1H-pyrrole-2-carboxylic acid thiazol-2-ylamide;
(+) 1-[1-(4-Fluoro-phenyl)-ethyl]-4-isobutyl-1H-pyrrole-2-carboxylic acid thiazol-2-ylamide
(−) 1-[1-(4-Fluoro-phenyl)-ethyl]-4-isobutyl-1H-pyrrole-2-carboxylic acid thiazol-2-ylamide;
1-[1-(4-Fluoro-phenyl)-ethyl]-4-isobutyl-1H-pyrrole-2-carboxylic acid (5-chloro-thiazol-2-yl)-amide;
(+) 1-[1-(4-Fluoro-phenyl)-ethyl]-4-isobutyl-1H-pyrrole-2-carboxylic acid (5-chloro-thiazol-2-yl)-amide;
(−) 1-[1-(4-Fluoro-phenyl)-ethyl]-4-isobutyl-1H-pyrrole-2-carboxylic acid (5-chloro-thiazol-2-yl)-amide;
1-[1-(4-Fluoro-phenyl)-ethyl]-4-isobutyl-1H-pyrrole-2-carboxylic acid (5-fluoro-thiazol-2-yl)-amide;
(+) 1-[1-(4-Fluoro-phenyl)-ethyl]-4-isobutyl-1H-pyrrole-2-carboxylic acid (5-fluoro-thiazol-2-yl)-amide;
(−) 1-[1-(4-Fluoro-phenyl)-ethyl]-4-isobutyl-1H-pyrrole-2-carboxylic acid (5-fluoro-thiazol-2-yl)-amide;
1-[2-(2,4-Difluoro-phenyl)-ethyl]-4-isobutyl-1H-pyrrole-2-carboxylic acid thiazol-2-ylamide;
4-Isobutyl-1-(2,3,4-trifluoro-benzyl)-1H-pyrrole-2-carboxylic acid thiazol-2-ylamide;
4-Isobutyl-1-(2,3,4-trifluoro-benzyl)-1H-pyrrole-2-carboxylic acid (5-chloro-thiazol-2-yl)-amide;
1-(4-Chloro-3-trifluoromethyl-benzyl)-4-isobutyl-1H-pyrrole-2-carboxylic acid thiazol-2-ylamide;
1-(4-Chloro-3-trifluoromethyl-benzyl)-4-isobutyl-1H-pyrrole-2-carboxylic acid (5-chloro-thiazol-2-yl)-amide;
1-(2,6-Difluoro-benzyl)-4-isobutyl-1H-pyrrole-2-carboxylic acid thiazol-2-ylamide;
1-(2,6-Difluoro-benzyl)-4-isobutyl-1H-pyrrole-2-carboxylic acid (5-chloro-thiazol-2-yl)-amide;
1-(3-Chloro-benzyl)-4-isobutyl-1H-pyrrole-2-carboxylic acid thiazol-2-ylamide;
1-(3-Chloro-benzyl)-4-isobutyl-1H-pyrrole-2-carboxylic acid (5-chloro-thiazol-2-yl)-amide;
1-(3-Fluoro-benzyl)-4-isobutyl-1H-pyrrole-2-carboxylic acid thiazol-2-ylamide;
1-(3-Fluoro-benzyl)-4-isobutyl-1H-pyrrole-2-carboxylic acid (5-chloro-thiazol-2-yl)-amide;
1-(2-Chloro-5-fluoro-benzyl)-4-isobutyl-1H-pyrrole-2-carboxylic acid thiazol-2-ylamide;
1-(2-Chloro-5-fluoro-benzyl)-4-isobutyl-1H-pyrrole-2-carboxylic acid (5-chloro-thiazol-2-yl)-amide;
4-Isobutyl-1-[2-(4-methanesulfonyl-phenyl)-ethyl]-1H-pyrrole-2-carboxylic acid thiazol-2-ylamide;
4-Isobutyl-1-(4-methanesulfonyl-benzyl)-1H-pyrrole-2-carboxylic acid thiazol-2-ylamide;
4-Isobutyl-1-(4-methanesulfonyl-benzyl)-1H-pyrrole-2-carboxylic acid (5-chloro-thiazol-2-yl)-amide;
1-(3-Fluoro-4-trifluoromethyl-benzyl)-4-isobutyl-1H-pyrrole-2-carboxylic acid thiazol-2-ylamide;
1-(3-Fluoro-4-trifluoromethyl-benzyl)-4-isobutyl-1H-pyrrole-2-carboxylic acid (5-chloro-thiazol-2-yl)-amide;
4-Isobutyl-1-(4-methylsulfanyl-benzyl)-1H-pyrrole-2-carboxylic acid thiazol-2-ylamide;
1-(3,4-Difluoro-benzyl)-4-ethyl-1H-pyrrole-2-carboxylic acid thiazol-2-ylamide;

1-(3,4-Difluoro-benzyl)-4-ethyl-1H-pyrrole-2-carboxylic acid (5-chloro-thiazol-2-yl)-amide;
1-(3-Chloro-5-fluoro-benzyl)-4-isobutyl-1H-pyrrole-2-carboxylic acid thiazol-2-ylamide;
1-(3-Chloro-5-fluoro-benzyl)-4-isobutyl-1H-pyrrole-2-carboxylic acid (5-chloro-thiazol-2-yl)-amide;
1-(4-Chloro-benzyl)-4-isobutyl-1H-pyrrole-2-carboxylic acid thiazol-2-ylamide;
1-(4-Chloro-benzyl)-4-isobutyl-1H-pyrrole-2-carboxylic acid (5-chloro-thiazol-2-yl)-amide;
1-(2,3-Difluoro-benzyl)-4-isobutyl-1H-pyrrole-2-carboxylic acid thiazol-2-ylamide;
1-(2,3-Difluoro-benzyl)-4-isobutyl-1H-pyrrole-2-carboxylic acid (5-chloro-thiazol-2-yl)-amide;
1-Benzyl-4-isobutyl-1H-pyrrole-2-carboxylic acid (5-chloro-thiazol-2-yl)-amide;
4-Isobutyl-1-(thiophene-2-sulfonyl)-1H-pyrrole-2-carboxylic acid (5-chloro-thiazol-2-yl)-amide;
4-Isobutyl-1-(2,3,6-trifluoro-benzyl)-1H-pyrrole-2-carboxylic acid (5-chloro-thiazol-2-yl)-amide;
1-(2-Chloro-6-fluoro-benzyl)-4-isobutyl-1H-pyrrole-2-carboxylic acid thiazol-2-ylamide;
1-(2-Chloro-6-fluoro-benzyl)-4-isobutyl-1H-pyrrole-2-carboxylic acid (5-chloro-thiazol-2-yl)-amide;
1-(2,5-Dichloro-benzyl)-4-isobutyl-1H-pyrrole-2-carboxylic acid thiazol-2-ylamide;
1-(2,5-Dichloro-benzyl)-4-isobutyl-1H-pyrrole-2-carboxylic acid (5-chloro-thiazol-2-yl)-amide;
1-(3,4-Difluoro-benzyl)-4-propyl-1H-pyrrole-2-carboxylic acid thiazol-2-ylamide;
1-(3,4-Difluoro-benzyl)-4-propyl-1H-pyrrole-2-carboxylic acid (5-chloro-thiazol-2-yl)-amide;
1-(3-Chloro-4-fluoro-benzyl)-4-isobutyl-1H-pyrrole-2-carboxylic acid (5-chloro-thiazol-2-yl)-amide;
1-(4-Chloro-3-fluoro-benzyl)-4-isobutyl-1H-pyrrole-2-carboxylic acid (5-chlorothiazol-2-yl)-amide;
4-Isobutyl-1-(4-methanesulfonyl-benzyl)-1H-pyrrole-2-carboxylic acid (5-fluorothiazol-2-yl)-amide;
1-(3,4-Difluoro-benzyl)-4-isobutyl-1H-pyrrole-2-carboxylic acid (4-trifluoromethyl-thiazol-2-yl)-amide;
1-(3,4-Difluoro-benzyl)-4-isobutyl-1H-pyrrole-2-carboxylic acid (1-methyl-5-oxo-4,5-dihydro-1H-imidazol-2-yl)-amide;
1-(4-Cyclopropanesulfonyl-benzyl)-4-isobutyl-1H-pyrrole-2-carboxylic acid (5-chloro-thiazol-2-yl)-amide;
1-(4-Cyclopropanesulfonyl-benzyl)-4-isobutyl-1H-pyrrole-2-carboxylic acid (5-fluoro-thiazol-2-yl)-amide;
1-(3,4-Difluoro-benzyl)-4-(4-methanesulfonyl-benzyl)-1H-pyrrole-2-carboxylic acid (5-fluoro-thiazol-2-yl)-amide;
(5-Chloro-2-{[1-(4-fluoro-3-trifluoromethyl-benzyl)-4-isobutyl-1H-pyrrole-2-carbonyl]-amino}-thiazol-4-yl)-acetic acid ethyl ester;
6-{[1-(4-Fluoro-3-trifluoromethyl-benzyl)-4-isobutyl-1H-pyrrole-2-carbonyl]-amino}-nicotinic acid methyl ester;
(2-{[1-(2,4-Difluoro-benzyl)-4-isobutyl-1H-pyrrole-2-carbonyl]-amino}-thiazol-4-yl)-acetic acid ethyl ester;
6-{[1-(2,4-Difluoro-benzyl)-4-isobutyl-1H-pyrrole-2-carbonyl]-amino}-nicotinic acid methyl ester;
(2-{[1-(4-Fluoro-3-trifluoromethyl-benzyl)-4-isobutyl-1H-pyrrole-2-carbonyl]-amino}-thiazol-4-yl)-acetic acid ethyl ester;
(2-{[4-Isobutyl-1-(2-thiophen-3-yl-ethyl)-1H-pyrrole-2-carbonyl]-amino}-thiazol-4-yl)-acetic acid ethyl ester;
(2-{[4-Isobutyl-1-(2-thiophen-2-yl-ethyl)-1H-pyrrole-2-carbonyl]-amino}-thiazol-4-yl)-acetic acid ethyl ester;
(5-Chloro-2-[1-(3,4-dichloro-benzyl)-4-isobutyl-1H-pyrrole-2-carbonyl)amino]-thiazol-4-yl)-acetic acid ethyl ester;
(5-Chloro-2-{[1-(3,4-difluoro-benzyl)-4-isobutyl-1H-pyrrole-2-carbonyl]-amino}-thiazol-4-yl)-acetic acid ethyl ester;
3-(2-{[1-(3,4-Difluoro-benzyl)-4-isobutyl-1H-pyrrole-2-carbonyl]-amino}-thiazol-4-yl)-propionic acid ethyl ester;
(5-Chloro-2-{[1-(3-chloro-4-fluoro-benzyl)-4-isobutyl-1H-pyrrole-2-carbonyl]-amino}-thiazol-4-yl)-acetic acid ethyl ester;
(5-Chloro-2-{[1-(4-chloro-3-fluoro-benzyl)-4-isobutyl-1H-pyrrole-2-carbonyl]-amino}-thiazol-4-yl)-acetic acid ethyl ester;
6-{[1-(3,4-Difluoro-benzyl)-4-isobutyl-1H-pyrrole-2-carbonyl]-amino}-nicotinic acid methyl ester;
(5-Chloro-2-{[4-isobutyl-1-(4-methanesulfonyl-benzyl)-1H-pyrrole-2-carbonyl]-amino}-thiazol-4-yl)-acetic acid ethyl ester;
(2-{[4-Isobutyl-1-(4-methanesulfonyl-benzyl)-1H-pyrrole-2-carbonyl]-amino}-thiazol-4-yl)-acetic acid ethyl ester;
(5-Chloro-2-{[1-(2,4-difluoro-benzyl)-4-isobutyl-1H-pyrrole-2-carbonyl]-amino}-thiazol-4-yl)-acetic acid ethyl ester;
(5-Chloro-2-{[1-(4-cyclopropanesulfonyl-benzyl)-4-isobutyl-1H-pyrrole-2-carbonyl]-amino}-thiazol-4-yl)-acetic acid ethyl ester;
(5-Chloro-2-{[1-(3,4-difluoro-benzyl)-4-(4-methanesulfonyl-benzyl)-1H-pyrrole-2-carbonyl]-amino}-thiazol-4-yl)-acetic acid ethyl ester;
1-(3,4-Difluoro-benzyl)-4-isobutyryl-1H-pyrrole-2-carboxylic acid thiazol-2-ylamide;
4-Cyclopropanecarbonyl-1-(3,4-difluoro-benzyl)-1H-pyrrole-2-carboxylic acid thiazol-2-ylamide;
4-Cyclopropanecarbonyl-1-(3,4-difluorobenzyl)-1H-pyrrole-2-carboxylicacid (5-chloro-thiazol-2-yl)-amide;
1-(3,4-Difluoro-benzyl)-4-isobutyryl-1H-pyrrole-2-carboxylic acid (5-chloro-thiazol-2-yl)-amide;
1-(2,3-Difluoro-benzyl)-4-isobutyryl-1H-pyrrole-2-carboxylic acid (5-chloro-thiazol-2-yl)-amide;
(5-Chloro-2-{[1-(3,4-difluoro-benzyl)-4-isobutyryl-1H-pyrrole-2-carbonyl]-amino}-thiazol-4-yl)-acetic acid ethyl ester;
(5-Chloro-2-{[1-(4-cyclopropanesulfonyl-benzyl)-4-isobutyryl-1H-pyrrole-2-carbonyl]-amino}-thiazol-4-yl)-acetic acid ethyl ester;
1-(4-Fluoro-3-trifluoromethyl-benzyl)-4-isobutyryl-1H-pyrrole-2-carboxylic acid thiazol-2-ylamide;
1-(4-Fluoro-3-trifluoromethyl-benzyl)-4-isobutyryl-1H-pyrrole-2-carboxylic acid (5-chloro-thiazol-2-yl)-amide;
1-(4-Fluoro-3-trifluoromethyl-benzyl)-4-isobutyryl-1H-pyrrole-2-carboxylic acid (5-fluoro-thiazol-2-yl)-amide;
(5-Chloro-2-{[1-(4-fluoro-3-trifluoromethyl-benzyl)-4-isobutyryl-1H-pyrrole-2-carbonyl]-amino}-thiazol-4-yl)-acetic acid ethyl ester;
1-(3,4-Difluoro-benzyl)-4-(1-hydroxy-2-methyl-propyl)-1H-pyrrole-2-carboxylic acid thiazol-2-ylamide;
(+) 1-(3,4-Difluoro-benzyl)-4-(1-hydroxy-2-methyl-propyl)-1H-pyrrole-2-carboxylic acid thiazol-2-ylamide;
(−) 1-(3,4-Difluoro-benzyl)-4-(1-hydroxy-2-methyl-propyl)-1H-pyrrole-2-carboxylic acid thiazol-2-ylamide;

1-(3,4-Difluoro-benzyl)-4-(1-hydroxy-2-methyl-propyl)-1H-pyrrole-2-carboxylic acid (5-chloro-thiazol-2-yl)-amide;

(+) 1-(3,4-Difluoro-benzyl)-4-(1-hydroxy-2-methyl-propyl)-1H-pyrrole-2-carboxylic acid (5-chloro-thiazol-2-yl)-amide;

(−) 1-(3,4-Difluoro-benzyl)-4-(1-hydroxy-2-methyl-propyl)-1H-pyrrole-2-carboxylic acid (5-chloro-thiazol-2-yl)-amide;

1-(2,3-Difluoro-benzyl)-4-(1-hydroxy-2-methyl-propyl)-1H-pyrrole-2-carboxylic acid (5-chloro-thiazol-2-yl)-amide;

(+) 1-(2,3-Difluoro-benzyl)-4-(1-hydroxy-2-methyl-propyl)-1H-pyrrole-2-carboxylic acid (5-chloro-thiazol-2-yl)-amide;

(−) 1-(2,3-Difluoro-benzyl)-4-(1-hydroxy-2-methyl-propyl)-1H-pyrrole-2-carboxylic acid (5-chloro-thiazol-2-yl)-amide;

(5-Chloro-2-{[1-(4-cyclopropanesulfonyl-benzyl)-4-(1-hydroxy-2-methyl-propyl)-1H-pyrrole-2-carbonyl]-amino}-thiazol-4-yl)-acetic acid ethyl ester;

(+) (5-Chloro-2-{[1-(4-cyclopropanesulfonyl-benzyl)-4-(1-hydroxy-2-methyl-propyl)-1H-pyrrole-2-carbonyl]-amino}-thiazol-4-yl)-acetic acid ethyl ester;

(−) (5-Chloro-2-{[1-(4-cyclopropanesulfonyl-benzyl)-4-(1-hydroxy-2-methyl-propyl)-1H-pyrrole-2-carbonyl]-amino}-thiazol-4-yl)-acetic acid ethyl ester;

4-(1-Hydroxy-2-methyl-propyl)-1-(4-methanesulfonyl-benzyl)-1H-pyrrole-2-carboxylic acid thiazol-2-ylamide;

(+)-4-(1-Hydroxy-2-methyl-propyl)-1-(4-methanesulfonyl-benzyl)-1H-pyrrole-2-carboxylic acid thiazol-2-ylamide;

(−) 4-(1-Hydroxy-2-methyl-propyl)-1-(4-methanesulfonyl-benzyl)-1H-pyrrole-2-carboxylic acid thiazol-2-ylamide;

4-(1-Hydroxy-2-methyl-propyl)-1-(4-methanesulfonyl-benzyl)-1H-pyrrole-2-carboxylic acid (5-chloro-thiazol-2-yl)-amide;

(+) 4-(1-Hydroxy-2-methyl-propyl)-1-(4-methanesulfonyl-benzyl)-1H-pyrrole-2-carboxylic acid (5-chloro-thiazol-2-yl)-amide;

(−) 4-(1-Hydroxy-2-methyl-propyl)-1-(4-methanesulfonyl-benzyl)-1H-pyrrole-2-carboxylic acid (5-chloro-thiazol-2-yl)-amide;

4-(1-Hydroxy-2-methyl-propyl)-1-(4-methanesulfonyl-benzyl)-1H-pyrrole-2-carboxylic acid (5-fluoro-thiazol-2-yl)-amide;

(+) 4-(1-Hydroxy-2-methyl-propyl)-1-(4-methanesulfonyl-benzyl)-1H-pyrrole-2-carboxylic acid (5-fluoro-thiazol-2-yl)-amide;

(−) 4-(1-Hydroxy-2-methyl-propyl)-1-(4-methanesulfonyl-benzyl)-1H-pyrrole-2-carboxylic acid (5-fluoro-thiazol-2-yl)-amide;

1-(2,4-Difluoro-benzyl)-4-(1-hydroxy-2-methyl-propyl)-1H-pyrrole-2-carboxylic acid (5-fluoro-thiazol-2-yl)-amide;

(+) 1-(2,4-Difluoro-benzyl)-4-(1-hydroxy-2-methyl-propyl)-1H-pyrrole-2-carboxylic acid (5-fluoro-thiazol-2-yl)-amide;

(−) 1-(2,4-Difluoro-benzyl)-4-(1-hydroxy-2-methyl-propyl)-1H-pyrrole-2-carboxylic acid (5-fluoro-thiazol-2-yl)-amide;

1-(4-Cyclopropanesulfonyl-benzyl)-4-(1-hydroxy-2-methyl-propyl)-1H-pyrrole-2-carboxylic acid (5-fluoro-thiazol-2-yl)-amide;

(+) 1-(4-Cyclopropanesulfonyl-benzyl)-4-(1-hydroxy-2-methyl-propyl)-1H-pyrrole-2-carboxylic acid (5-fluoro-thiazol-2-yl)-amide;

(−) 1-(4-Cyclopropanesulfonyl-benzyl)-4-(1-hydroxy-2-methyl-propyl)-1H-pyrrole-2-carboxylic acid (5-fluoro-thiazol-2-yl)-amide;

1-(4-Cyclopropanesulfonyl-benzyl)-4-(1-hydroxy-2-methyl-propyl)-1H-pyrrole-2-carboxylic acid (5-chloro-thiazol-2-yl)-amide;

(+) 1-(4-Cyclopropanesulfonyl-benzyl)-4-(1-hydroxy-2-methyl-propyl)-1H-pyrrole-2-carboxylic acid (5-chloro-thiazol-2-yl)-amide;

(−) 1-(4-Cyclopropanesulfonyl-benzyl)-4-(1-hydroxy-2-methyl-propyl)-1H-pyrrole-2-carboxylic acid (5-chloro-thiazol-2-yl)-amide;

1-(4-Fluoro-3-trifluoromethyl-benzyl)-4-(1-hydroxy-2-methyl-propyl)-1H-pyrrole-2-carboxylic acid thiazol-2-ylamide;

(+) 1-(4-Fluoro-3-trifluoromethyl-benzyl)-4-(1-hydroxy-2-methyl-propyl)-1H-pyrrole-2-carboxylic acid thiazol-2-ylamide;

(−) 1-(4-Fluoro-3-trifluoromethyl-benzyl)-4-(1-hydroxy-2-methyl-propyl)-1H-pyrrole-2-carboxylic acid thiazol-2-ylamide;

1-(4-Fluoro-3-trifluoromethyl-benzyl)-4-(1-hydroxy-2-methyl-propyl)-1H-pyrrole-2-carboxylic acid (5-chloro-thiazol-2-yl)-amide;

(+) 1-(4-Fluoro-3-trifluoromethyl-benzyl)-4-(1-hydroxy-2-methyl-propyl)-1H-pyrrole-2-carboxylic acid (5-chloro-thiazol-2-yl)-amide;

(−) 1-(4-Fluoro-3-trifluoromethyl-benzyl)-4-(1-hydroxy-2-methyl-propyl)-1H-pyrrole-2-carboxylic acid (5-chloro-thiazol-2-yl)-amide;

1-(4-Fluoro-3-trifluoromethyl-benzyl)-4-(1-hydroxy-2-methyl-propyl)-1H-pyrrole-2-carboxylic acid (5-fluoro-thiazol-2-yl)-amide;

(+) 1-(4-Fluoro-3-trifluoromethyl-benzyl)-4-(1-hydroxy-2-methyl-propyl)-1H-pyrrole-2-carboxylic acid (5-fluoro-thiazol-2-yl)-amide;

(−) 1-(4-Fluoro-3-trifluoromethyl-benzyl)-4-(1-hydroxy-2-methyl-propyl)-1H-pyrrole-2-carboxylic acid (5-fluoro-thiazol-2-yl)-amide;

(5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester;

(+) (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester;

(−) (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester;

(5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester;

(+) (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester;

(−) (5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid ethyl ester;

(5-Chloro-2-{[1-(3,4-difluoro-benzyl)-4-(1-hydroxy-2-methyl-propyl)-1H-pyrrole-2-carbonyl]-amino}-thiazol-4-yl)-acetic acid ethyl ester;

(+) (5-Chloro-2-{[1-(3,4-difluoro-benzyl)-4-(1-hydroxy-2-methyl-propyl)-1H-pyrrole-2-carbonyl]-amino}-thiazol-4-yl)-acetic acid ethyl ester;

(−) (5-Chloro-2-{[1-(3,4-difluoro-benzyl)-4-(1-hydroxy-2-methyl-propyl)-1H-pyrrole-2-carbonyl]-amino}-thiazol-4-yl)-acetic acid ethyl ester;
1-(3,4-Difluoro-benzyl)-4-(thiophene-2-sulfonyl)-1H-pyrrole-2-carboxylic acid (5-chloro-thiazol-2-yl)-amide;
1-(3,4-Difluoro-benzyl)-4-(thiophene-2sulfonyl)-1H-pyrrole-2-carboxylic acid (5-chloro-thiazol-2-yl)-amide;
1-(3,4-Difluoro-benzyl)-4-(thiophene-2-sulfonyl)-1H-pyrrole-2-carboxylic acid (5-fluoro-thiazol-2-yl)-amide;
1-(4-Chloro-3-fluoro-benzyl)-4-(thiophene-2-sulfonyl)-1H-pyrrole-2-carboxylic acid (5-chloro-thiazol-2-yl)-amide;
1-(4-Chloro-3-fluoro-benzyl)-4-(thiophene-2-sulfonyl)-1H-pyrrole-2-carboxylic acid (5-fluoro-thiazol-2-yl)-amide;
(5-Chloro-2-{[1-(3,4-difluoro-benzyl)-4-(thiophene-2-sulfonyl)-1H-pyrrole-2-carbonyl]-amino}-thiazol-4-yl)-acetic acid ethyl ester;
(5-Chloro-2-{[1-(4-chloro-3-fluoro-benzyl)-4-(thiophene-2-sulfonyl)-1H-pyrrole-2-carbonyl]-amino}-thiazol-4-yl)-acetic acid ethyl ester;
(5-Chloro-2-{[1-(2,4-difluoro-benzyl)-4-isobutyl-1H-pyrrole-2-carbonyl]-amino}-thiazol-4-yl)-acetic acid;
(5-Chloro-2-{[1-(4-fluoro-3-trifluoromethyl-benzyl)-4-isobutyl-1H-pyrrole-2-carbonyl]-amino}-thiazol-4-yl)-acetic acid;
6-{[1-(4-Fluoro-3-trifluoromethyl-benzyl)-4-isobutyl-1H-pyrrole-2-carbonyl]-amino}-nicotinic acid;
(2-{[1-(2,4-Difluoro-benzyl)-4-isobutyl-1H-pyrrole-2-carbonyl]-amino}-thiazol-4-yl)-acetic acid;
6-{[1-(2,4-Difluoro-benzyl)-4-isobutyl-1H-pyrrole-2-carbonyl]-amino}-nicotinic acid;
(2-{[1-(4-Fluoro-3-trifluoromethyl-benzyl)-4-isobutyl-1H-pyrrole-2-carbonyl]-amino}-thiazol-4-yl)-acetic acid;
(2-{[4-Isobutyl-1-(2-thiophen-3-yl-ethyl)-1H-pyrrole-2-carbonyl]-amino}-thiazol-4-yl)-acetic acid;
(2-{[4-Isobutyl-1-(2-thiophen-2-yl-ethyl)-1H-pyrrole-2-carbonyl]-amino}-thiazol-4-yl)-acetic acid;
(5-Chloro-2-{[1-(3,4-dichloro-benzyl)-4-isobutyl-1H-pyrrole-2-carbonyl]-amino}-thiazol-4-yl)-acetic acid;
(5-Chloro-2-{[1-(3,4-difluoro-benzyl)-4-isobutyl-1H-pyrrole-2-carbonyl]-amino}-thiazol-4-yl)-acetic acid;
3-(2-{[1-(3,4-Difluoro-benzyl)-4-isobutyl-1H-pyrrole-2-carbonyl]-amino}-thiazol-4-yl)-propionic acid;
(5-Chloro-2-{[1-(3-chloro-4-fluoro-benzyl)-4-isobutyl-1H-pyrrole-2-carbonyl]-amino}-thiazol-4-yl)-acetic acid;
(5-Chloro-2-{[1-(4-chloro-3-fluoro-benzyl)-4-isobutyl-1H-pyrrole-2-carbonyl]-amino}-thiazol-4-yl)-acetic acid;
(5-Chloro-2-{[1-(3,4-difluoro-benzyl)-4-(1-hydroxy-2-methyl-propyl)-1H-pyrrole-2-carbonyl]-amino}-thiazol-4-yl)-acetic acid;
6-{[1-(3,4-Difluoro-benzyl)-4-isobutyl-1H-pyrrole-2-carbonyl]-amino}-nicotinic acid;
(5-Chloro-2-{[4-isobutyl-1-(4-methanesulfonyl-benzyl)-1H-pyrrole-2-carbonyl]-amino}-thiazol-4-yl)-acetic acid;
(5-Chloro-2-{[1-(3,4-difluoro-benzyl)-4-(thiophene-2-sulfonyl)-1H-pyrrole-2-carbonyl]-amino}-thiazol-4-yl)-acetic acid;
(5-Chloro-2-{[1-(4-chloro-3-fluoro-benzyl)-4-(thiophene-2-sulfonyl)-1H-pyrrole-2-carbonyl]-amino}-thiazol-4-yl)-acetic acid;
(2-{[4-Isobutyl-1-(4-methanesulfonyl-benzyl)-1H-pyrrole-2-carbonyl]-amino}-thiazol-4-yl)-acetic acid;
(5-Chloro-2-{[4-(1-hydroxy-2-methyl-propyl)-1-(4-methanesulfonyl-benzyl)-1H-pyrrole-2-carbonyl]-amino}-thiazol-4-yl)-acetic acid;
(5-Chloro-2-{[1-(4-cyclopropanesulfonyl-benzyl)-4-isobutyl-1H-pyrrole-2-carbonyl]-amino}-thiazol-4-yl)-acetic acid;
(5-Chloro-2-{[1-(4-cyclopropanesulfonyl-benzyl)-4-(1-hydroxy-2-methyl-propyl)-1H-pyrrole-2-carbonyl]-amino}-thiazol-4-yl)-acetic acid;
(5-Chloro-2-{[1-(3,4-difluoro-benzyl)-4-(4-methanesulfonyl-benzyl)-1H-pyrrole-2-carbonyl]-amino}-thiazol-4-yl)-acetic acid;
(5-Chloro-2-{[1-(4-fluoro-3-trifluoromethyl-benzyl)-4-isobutyryl-1H-pyrrole-2-carbonyl]-amino}-thiazol-4-yl)-acetic acid;
(5-Chloro-2-{[1-(4-fluoro-3-trifluoromethyl-benzyl)-4-(1-hydroxy-2-methyl-propyl)-1H-pyrrole-2-carbonyl]-amino}-thiazol-4-yl)-acetic acid; and
(5-Chloro-2-{[1-(3,4-difluoro-benzyl)-4-isobutyryl-1H-pyrrole-2-carbonyl]-amino}-thiazol-4-yl)-acetic acid;
(5-Chloro-2-{[1-(4-chloro-3-fluoro-benzyl)-4-(1-hydroxy-2-methyl-propyl)-1H-pyrrole-2-carbonyl]-amino}-thiazol-4-yl)-acetic acid;
(2-{[1-(4-Chloro-3-fluoro-benzyl)-4-(1-hydroxy-2-methyl-propyl)-1H-pyrrole-2-carbonyl]-amino}-thiazol-4-yl)-acetic acid;
(5-Chloro-2-{[1-(3-fluoro-4-trifluoromethyl-benzyl)-4-(1-hydroxy-2-methyl-propyl)-1H-pyrrole-2-carbonyl]-amino}-thiazol-4-yl)-acetic acid;
(2-{[1-(3-Fluoro-4-trifluoromethyl-benzyl)-4-(1-hydroxy-2-methyl-propyl)-1H-pyrrole-2-carbonyl]-amino}-thiazol-4-yl)-acetic acid;
(5-Chloro-2-{[1-(4-chloro-3-trifluoromethyl-benzyl)-4-(1-hydroxy-2-methyl-propyl)-1H-pyrrole-2-carbonyl]-amino}-thiazol-4-yl)-acetic acid;
(2-{[1-(4-Chloro-3-trifluoromethyl-benzyl)-4-(1-hydroxy-2-methyl-propyl)-1H-pyrrole-2-carbonyl]-amino}-thiazol-4-yl)-acetic acid;
(5-Chloro-2-{[1-(3-fluoro-benzyl)-4-(1-hydroxy-2-methyl-propyl)-1H-pyrrole-2-carbonyl]-amino}-thiazol-4-yl)-acetic acid;
(2-{[1-(3-Fluoro-benzyl)-4-(1-hydroxy-2-methyl-propyl)-1H-pyrrole-2-carbonyl]-amino}-thiazol-4-yl)-acetic acid;
(5-Chloro-2-{[1-(2,4-difluoro-benzyl)-4-(1-hydroxy-2-methyl-propyl)-1H-pyrrole-2-carbonyl]-amino}-thiazol-4-yl)-acetic acid;
(2-{[1-(2,4-Difluoro-benzyl)-4-(1-hydroxy-2-methyl-propyl)-1H-pyrrole-2-carbonyl]-amino}-thiazol-4-yl)-acetic acid;
(5-Chloro-2-{[1-(2,4-dichloro-benzyl)-4-(1-hydroxy-2-methyl-propyl)-1H-pyrrole-2-carbonyl]-amino}-thiazol-4-yl)-acetic acid;
(2-{[1-(2,4-Dichloro-benzyl)-4-(1-hydroxy-2-methyl-propyl)-1H-pyrrole-2-carbonyl]-amino}-thiazol-4-yl)-acetic acid;
(5-Chloro-2-{[4-(1-hydroxy-2-methyl-propyl)-1-(4-trifluoromethyl-benzyl)-1H-pyrrole-2-carbonyl]-amino}-thiazol-4-yl)-acetic acid;
(2-{[4-(1-Hydroxy-2-methyl-propyl)-1-(4-trifluoromethyl-benzyl)-1H-pyrrole-2-carbonyl]-amino}-thiazol-4-yl)-acetic acid;
(5-Chloro-2-{[4-(1-hydroxy-2-methyl-propyl)-1-(3-trifluoromethyl-benzyl)-1H-pyrrole-2-carbonyl]-amino}-thiazol-4-yl)-acetic acid;

(2-{[4-(1-Hydroxy-2-methyl-propyl)-1-(3-trifluorom-ethyl-benzyl)-1H-pyrrole-2-carbonyl]-amino}-thiazol-4-yl)-acetic acid;
(5-Chloro-2-{[1-(4-chloro-benzyl)-4-(1-hydroxy-2-methyl-propyl)-1H-pyrrole-2-carbonyl]-amino}-thiazol-4-yl)-acetic acid;
(2-{[1-(4-Chloro-benzyl)-4-(1-hydroxy-2-methyl-propyl)-1H-pyrrole-2-carbonyl]-amino}-thiazol-4-yl)-acetic acid;
(5-Chloro-2-{[1-(3,4-dichloro-benzyl)-4-(1-hydroxy-2-methyl-propyl)-1H-pyrrole-2-carbonyl]-amino}-thiazol-4-yl)-acetic acid;
(2-{[1-(3,4-Dichloro-benzyl)-4-(1-hydroxy-2-methyl-propyl)-1H-pyrrole-2-carbonyl]-amino}-thiazol-4-yl)-acetic acid;
(5-Chloro-2-{[1-(4-fluoro-benzyl)-4-(1-hydroxy-2-methyl-propyl)-1H-pyrrole-2-carbonyl]-amino}-thiazol-4-yl)-acetic acid; and
(2-{[1-(4-Fluoro-benzyl)-4-(1-hydroxy-2-methyl-propyl)-1H-pyrrole-2-carbonyl]-amino}-thiazol-4-yl)-acetic acid.

5. A pharmaceutical composition comprising, as an active ingredient, at least one compound of formula (I), as claimed in any one of the claims 1-2 or 3-4, or its stereoisomer, or a pharmaceutically acceptable salt thereof, together with one or more pharmaceutically acceptable carriers or excipients.

6. A pharmaceutical composition comprising, as an active ingredient, at least one compound of formula (I), as claimed in any one of the claims 1-2 or 3-4, or its stereoisomer, or a pharmaceutically acceptable salt thereof, in combination with one or more pharmaceutically acceptable therapeutically active agents.

7. The pharmaceutical composition as claimed in claim 6 wherein, the pharmaceutically acceptable therapeutically active agent is selected from anti-diabetic agents, anti-hyperglycemic agents, anti-obesity agents, anti-hypertensive agents or anti-dyslipidemic agents.

8. The pharmaceutical composition as claimed in claim 6 or 7 wherein the pharmaceutically acceptable therapeutically active agents is selected from: insulin secretagogues, sulfonylureas, insulinotropic sulfonyl urea receptor ligands, meglitinides, biguanides, glucagon antagonists, peptide glucagon antagonists, non-peptide glucagon antagonists, glucosidase inhibitors, glucose sensitive insulinotropic agents GLP-1 mimetics, insulin sensitizers, dipeptidyl peptidase-IV inhibitors, fibrates, niacin, statins, cholesterol absorption inhibitors, bile acid sequestrants, diuretics, angiotensin converting enzyme (ACE) inhibitors, angiotensin-II receptor type-I blockers (ARB), rennin inhibitors, β-adrenergic receptor blockers, calcium channel blockers, aldosterone receptor antagonists, and aldosterone synthase inhibitors.

9. A process for the preparation of a compound of formula (I) as claimed in any one of the claim 1-2 or 3-4 or its stereoisomer thereof, said process comprising:
reacting an acid of formula (II)

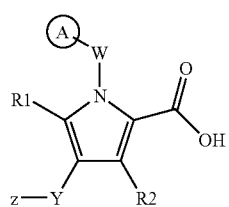

with a compound of formula (III)

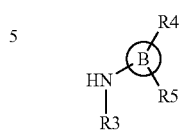

in presence of a suitable amide coupling reagent, optionally hydrolysing and optionally further coupling with an amine of formula $NHR^6R^7$ to obtain the compound of formula (I).

10. A process for the preparation of a compound of formula (I) as claimed in any one of the claim 1-2 or 3-4 or its stereoisomer thereof, said process comprising:
converting a compound of formula (Ib)

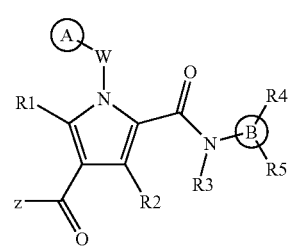

to a compound of formula (I)

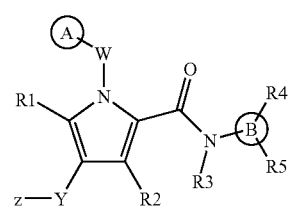

wherein Y is —CH(OH),
by hydrogenating a compound of formula (Ib) using catalyst $FeCl_2$, Pd—C or Raney nickel, or reducing a compound of formula (Ib) using Li, Na, K, $NH_3$, LiH, $BH_3$, $LiBH_4$, $SnCl_4$, $NaBH_4$, $NaBH_3CN$ or $LiHBEt_3$ in lower alcohols, THF, acetic acid or water at a temperature in the range of 0-150° C.

11. A compound of formula (I), as claimed in any one of the claims 1-2 or 3-4, or its stereoisomer, or a pharmaceutically acceptable salt thereof, as a partial activator of glucokinase wherein the $E_{max}$ is in the range of 60-90%.

12. A compound of formula (I), as claimed in any one of the claims 1-2 or 3-4, or its stereoisomer, or a pharmaceutically acceptable salt thereof, as a partial activator of glucokinase wherein the $E_{max}$ is in the range of 40-60%.

13. A compound of formula (I), as claimed in any one of the claims 1-2 or 3-4, or its stereoisomer, or a pharmaceutically acceptable salt thereof, as a partial activator of glucokinase wherein the $E_{max}$ is in the range of 20-40%.

14. The pharmaceutical composition as claimed in claim 6 or 7 wherein the pharmaceutically acceptable therapeutically active agents is selected from: amaryl, glyburide, glimepiride, glipyride, glipizide, nateglinide, rapaglinide, metformin, phenformin, buformin, acarbose, miglitol, GLP-1, exendin-4, troglitazone, rosiglitazone, pioglitazone, sitagliptin, vildagliptin, sibutramine, orlistat, rimonabant, gemfibrozil, fenofibrate, niacin, rosuvatatin, atorvastatin, simvastatin, ezetimibe, cholestyramine, hydrochlorothiazides, mannitol, indapamide, furosemide, captopril, enalapril, losartan, irbesartan, aliskerin, atenolol, metoprolol, amlodipine, nifedipine, spironolactone, and FAD286.

* * * * *